(12) United States Patent
Suka et al.

(10) Patent No.: US 9,040,222 B2
(45) Date of Patent: May 26, 2015

(54) POLYMERIZABLE TERTIARY ESTER COMPOUND, POLYMER, RESIST COMPOSITION, AND PATTERNING PROCESS

(71) Applicant: SHIN-ETSU CHEMICAL CO., LTD., Tokyo (JP)

(72) Inventors: Yuki Suka, Jyoetsu (JP); Jun Hatakeyama, Jyoetsu (JP); Koji Hasegawa, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 34 days.

(21) Appl. No.: 13/743,019

(22) Filed: Jan. 16, 2013

(65) Prior Publication Data

US 2013/0189620 A1   Jul. 25, 2013

(30) Foreign Application Priority Data

Jan. 24, 2012   (JP) .................................. 2012-012450

(51) Int. Cl.
*G03F 7/039* (2006.01)
*G03F 7/30* (2006.01)
*G03F 7/32* (2006.01)
(Continued)

(52) U.S. Cl.
CPC .............. *G03F 7/0392* (2013.01); *G03F 7/039* (2013.01); *C07C 69/653* (2013.01); *C08F 220/26* (2013.01); *G03F 7/0046* (2013.01); *G03F 7/0397* (2013.01); *G03F 7/30* (2013.01); *G03F 7/325* (2013.01); *G03F 7/2041* (2013.01); *G03F 7/11* (2013.01); *C08F 220/28* (2013.01); *C07C 2101/02* (2013.01); *C07C 2101/04* (2013.01); *C07C 2101/08* (2013.01); *C07C 2101/14* (2013.01); *C07C 2102/42* (2013.01); *C08F 220/24* (2013.01)

(58) Field of Classification Search
None
See application file for complete search history.

(56) References Cited

U.S. PATENT DOCUMENTS 6,136,500 A   10/2000   Kobayashi et al.
6,312,867 B1   11/2001   Kinsho et al.
(Continued)

FOREIGN PATENT DOCUMENTS

JP   A-04-039665   2/1992
JP   A-09-090637   4/1997
(Continued)

OTHER PUBLICATIONS

Arimitsu et al., "Effect of Phenolic Hydroxyl Residues on the Improvement of Acid-Proliferation-Type Photoimaging Materials," Journal of Photopolymer Science and Technology, 1996, vol. 9, pp. 29-30.
(Continued)

*Primary Examiner* — Sin Lee
(74) *Attorney, Agent, or Firm* — Oliff PLC

(57) ABSTRACT

The present invention provides a polymerizable tertiary ester compound represented by the following general formula (1a) or (1b). There is provided a polymerizable ester compound useful as a monomer for a base resin of a resist composition having a high resolution and a reduced pattern edge roughness in photolithography using a high-energy beam such as an ArF excimer laser light as a light source, especially in immersion lithography, a polymer containing a polymer of the ester compound, a resist composition containing the polymer as a base resin, and a patterning process using the resist composition.

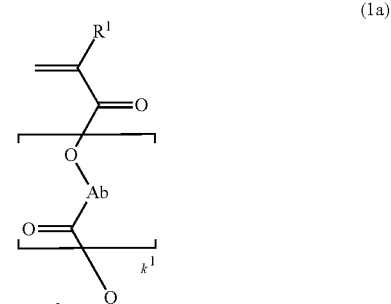

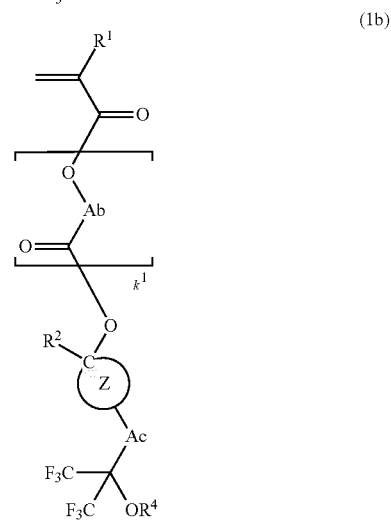

16 Claims, No Drawings

(51) Int. Cl.
*G03F 7/20* (2006.01)
*G03F 7/11* (2006.01)
*C08F 220/24* (2006.01)
*C07C 69/653* (2006.01)
*C08F 220/26* (2006.01)
*G03F 7/004* (2006.01)
*C08F 220/28* (2006.01)

(56) References Cited

U.S. PATENT DOCUMENTS

| | | | |
|---|---|---|---|
| 2002/0115874 A1 | 8/2002 | Kinsho et al. | |
| 2003/0013039 A1 | 1/2003 | Kobayashi et al. | |
| 2003/0078352 A1 | 4/2003 | Miyazawa et al. | |
| 2005/0026074 A1* | 2/2005 | Inabe et al. | 430/270.1 |
| 2005/0208419 A1* | 9/2005 | Inabe et al. | 430/270.1 |
| 2005/0215836 A1 | 9/2005 | Komata et al. | |
| 2008/0026317 A1 | 1/2008 | Breyta et al. | |
| 2008/0090172 A1 | 4/2008 | Hatakeyama et al. | |
| 2008/0102407 A1* | 5/2008 | Ohsawa et al. | 430/286.1 |
| 2008/0153030 A1 | 6/2008 | Kobayashi et al. | |
| 2008/0187860 A1* | 8/2008 | Tsubaki et al. | 430/270.1 |
| 2009/0035699 A1 | 2/2009 | Hasegawa et al. | |
| 2009/0274978 A1 | 11/2009 | Ohashi et al. | |
| 2010/0227274 A1 | 9/2010 | Hatakeyama et al. | |
| 2010/0239985 A1 | 9/2010 | Breyta et al. | |
| 2011/0076622 A1 | 3/2011 | Inabe et al. | |

FOREIGN PATENT DOCUMENTS

| | | |
|---|---|---|
| JP | A-2000-026446 | 1/2000 |
| JP | A-2000-159758 | 6/2000 |
| JP | A-2000-327633 | 11/2000 |
| JP | A-2000-336121 | 12/2000 |
| JP | A-2003-040840 | 2/2003 |
| JP | A-2003-066612 | 3/2003 |
| JP | A-2005-022992 | 1/2005 |
| JP | A-2005-239710 | 9/2005 |
| JP | A-2006-079048 | 3/2006 |
| JP | B2-3991462 | 10/2007 |
| JP | A-2008-122932 | 5/2008 |
| JP | A-2008-158339 | 7/2008 |
| JP | A-2009-029974 | 2/2009 |
| JP | A-2009-269953 | 11/2009 |
| JP | A-2010-237662 | 10/2010 |
| JP | A-2011-039266 | 2/2011 |

OTHER PUBLICATIONS

Arimitsu et al., "Sensitivity Enhancement of Chemical-Amplification-Type Photoimaging Materials by Acetoacetic Acid Derivatives," Journal of Photopolymer Science and Technology, 1995, vol. 8, pp. 43-44.

Kudo et al., "Enhancement of the Senestivity of Chemical-Amplification-Type Photoimaging Materials by β-Tosyloxyketone Acetals," Journal of Photopolymer Science and Technology, 1995, vol. 8, pp. 45-46.

May 27, 2014 Office Action issued in Japanese Patent Application No. 2012-012450 with a partial English translation.

Jul. 8, 2014 Notification of Reasons for Refusal issued in Japanese Application No. 2012-012450 with partial English-language translation.

* cited by examiner

POLYMERIZABLE TERTIARY ESTER COMPOUND, POLYMER, RESIST COMPOSITION, AND PATTERNING PROCESS

BACKGROUND OF THE INVENTION

1. Field of the Invention

The present invention relates to a polymerizable ester compound, particularly useful as a starting material for a functional material. Further, the present invention relates to a polymer having a repeating unit derived from the polymerizable ester compound, a photoresist material containing the polymer, and a patterning process using the photoresist material.

2. Description of the Related Art

In recent years, efforts have been made to achieve a finer pattern rule with increased integration and processing speeds in LSI devices. Deep-ultraviolet lithography has been developed as a technique capable of achieving microfabrication of 0.3 μm or less. In particular, a technique using a KrF excimer laser light has been completely known as an industrially production process.

Chemically amplified resist materials for use in photolithography using an ArF excimer laser light with a wavelength of 193 nm as a light source are, of course, required to have a high transparency in the wavelength. Further, they are required to have a high etching resistance enough to allow for film thickness reduction, a high sensitivity enough to avoid any burden on an expensive optical material, and especially a high resolution enough to form a precise micropattern. In order to meet these requirements, it is necessary to develop a base resin having a high transparency, rigidity, and reactivity. Such a base resin has been actively developed.

As a resin highly transparent to an ArF excimer laser light, a copolymer of acrylic or methacrylic acid derivatives (see Patent Document 1) has been known.

As disclosed in Patent Document 2, a combination of a (meth)acrylic unit having a methyladamantane ester as an acid labile group unit with a (meth)acrylic unit having a lactone ring ester as an adhesion group unit has been proposed as a (meth)acrylic resin. Patent Document 3 has described an acid labile group of exo form. The group has a high deprotection reactivity and a low activation energy for deprotection reaction. For this reason, it can obtain a high resolution and a low dependence on post exposure bake (PEB). Norbornane lactone as disclosed in Patent Documents 4 and 5 has been also proposed as an adhesion group having enhanced etching resistance. Patent Document 6 has described a specific compound having a high fluorine content and a hydroxy group. These studies have achieved significant improvements in the resolution of ArF resists.

However, from the conventional materials, a micropattern having a pitch less than 200 nm is unlikely to be formed, and additionally is not a complete rectangle. Further, the pattern has very rough surfaces and side walls. Therefore, the pattern does not reach a practically acceptable level. Among the problems of the conventional materials, there is the most serious problem of roughness in fine line size (line edge roughness). The problem largely affects the performance of a produced semiconductor device. Therefore, it is necessary to solve the problem. A smooth pattern can be simply formed by using a resin having a lower molecular weight or making an acid generated by a photoacid generator easy to move. Thus, the object can be accomplished to some extent. However, characteristics such as exposure dose dependence, density dependence, and mask fidelity extremely deteriorate, and fine fluctuation of a mask enlarges to make the line size uniform. As a result, line edge roughness does not reduce. In order to cope with a finer pattern of ArF excimer laser lithography and a high resolution by using an immersion lithography process, a fundamental improvement of line edge roughness is required.

PRIOR ART DOCUMENTS

Patent Documents

Patent Document 1: Japanese Patent Laid-Open Publication No. 4-39665

Patent Document 2: Japanese Patent Laid-Open Publication No. 9-90637

Patent Document 3: Japanese Patent Laid-Open Publication No. 2000-327633

Patent Document 4: Japanese Patent Laid-Open Publication No. 2000-26446

Patent Document 5: Japanese Patent Laid-Open Publication No. 2000-159758

Patent Document 6: Japanese Patent Laid-Open Publication No. 2003-040840

SUMMARY OF THE INVENTION

In view of the above situation, an object of the present invention is to provide a polymerizable ester compound useful as a monomer for a base resin of a resist composition having a high resolution and a reduced pattern edge roughness in photolithography using a high-energy beam such as an ArF excimer laser light as a light source, especially in immersion lithography, a polymer containing a polymer of the ester compound, a resist composition containing the polymer as a base resin, and a patterning process using the resist composition.

In order to address the problem, the present invention provides a polymerizable tertiary ester compound represented by the following general formula (1a) or (1b),

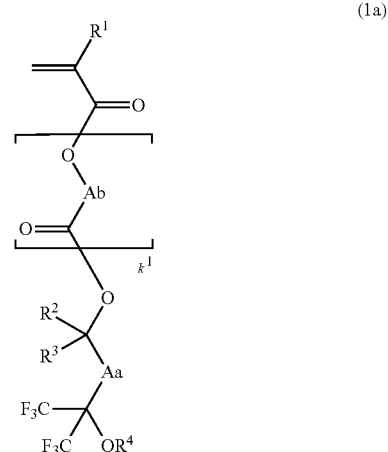

(1a)

-continued

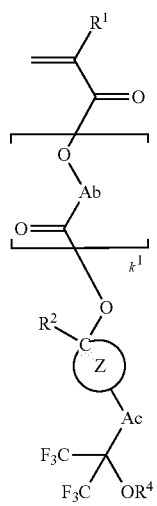

(1b)

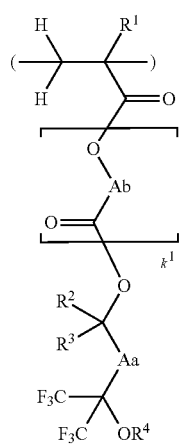

(2a)

wherein $R^1$ represents a hydrogen atom, a fluorine atom, a methyl group, or a trifluoromethyl group; each of $R^2$ and $R^3$ independently represents a linear, a branched, or a cyclic monovalent hydrocarbon group having 1 to 15 carbon atoms, or $R^2$ and $R^3$ may combine with each other to form a non-aromatic ring having 3 to 8 carbon atoms together with the carbon atoms to which they are bonded; Z represents a divalent group forming a substituted or an unsubstituted cyclopropane, cyclobutane, cyclopentane, cyclohexane, or norbornane ring together with the carbon atom to which it is bonded; Aa represents a linear, a branched, or a cyclic divalent hydrocarbon group having 1 to 10 carbon atoms; Ab represents a linear, a branched, or a cyclic divalent hydrocarbon group having 1 to 6 carbon atoms; Ac represents a single bond, or a linear, a branched, or a cyclic divalent hydrocarbon group having 1 to 10 carbon atoms; $R^4$ represents a hydrogen atom, or a linear, a branched, or a cyclic monovalent hydrocarbon group having 1 to 15 carbon atoms, and when $R^4$ is a monovalent hydrocarbon group, —$CH_2$— may be substituted with —O— or —C(=O)—; and $k^1$ is 0 or 1.

Such a polymerizable tertiary ester compound of the present invention is useful since a resist composition having a high resolution and a reduced pattern edge roughness in photolithography using a high-energy beam such as an ArF excimer laser light as a light source, especially in immersion lithography can be provided as a monomer for a base resin.

In this case, $k^1$ in the general formula (1a) or (1b) may be 1.

It is preferable that any one or more of $R^2$, $R^3$, and Aa have a cyclic structure in the formula (1a).

A compound having a cyclic structure in any one or more of $R^2$, $R^3$, and Aa can control acid diffusion and be used as a monomer for a base resin of a resist composition to become more effective in a reduced pattern edge roughness.

The present invention provides a polymer containing one or more kinds of repeating units represented by the following general formulae (2a) and (2b),

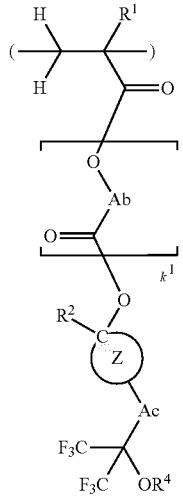

(2b)

wherein $R^1$ represents a hydrogen atom, a fluorine atom, a methyl group, or a trifluoromethyl group; each of $R^2$ and $R^3$ independently represents a linear, a branched, or a cyclic monovalent hydrocarbon group having 1 to 15 carbon atoms, or $R^2$ and $R^3$ may combine with each other to form a non-aromatic ring having 3 to 8 carbon atoms together with the carbon atoms to which they are bonded; Z represents a divalent group forming a substituted or an unsubstituted cyclopropane, cyclobutane, cyclopentane, cyclohexane, or norbornane ring together with the carbon atom to which it is bonded; Aa represents a linear, a branched, or a cyclic divalent hydrocarbon group having 1 to 10 carbon atoms; Ab represents a linear, a branched, or a cyclic divalent hydrocarbon group having 1 to 6 carbon atoms; Ac represents a single bond, or a linear, a branched, or a cyclic divalent hydrocarbon group having 1 to 10 carbon atoms; $R^4$ represents a hydrogen atom, or a linear, a branched, or a cyclic monovalent hydrocarbon group having 1 to 15 carbon atoms, and when $R^4$ is a monovalent hydrocarbon group, —$CH_2$— may be substituted with —O— or —(=O)—; and $k^1$ is 0 or 1.

The polymer of the present invention is useful as a base resin of a resist composition having a high resolution and a reduced pattern edge roughness.

In this case, $k^1$ in the general formula (2a) or (2b) may be 1.

It is preferable that any one or more of $R^2$, $R^3$, and Aa have a cyclic structure in the general formula (2a).

A compound having a cyclic structure in any one or more of $R^2$, $R^3$, and Aa can control acid diffusion and become more effective in a reduced pattern edge roughness.

The polymer further contains one or more kinds of repeating units represented by the following general formulae (3a) to (3d):

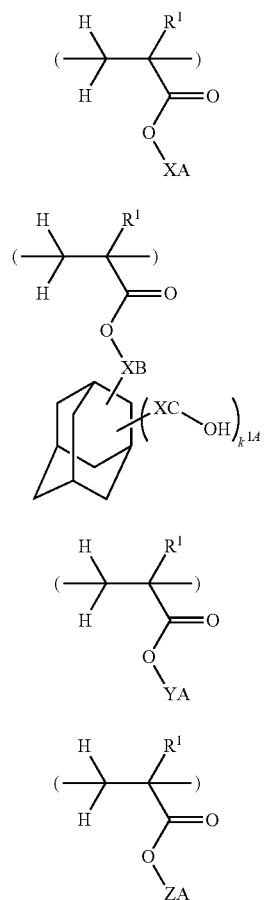

wherein $R^1$ is as defined above; XA represents an acid labile group; each of XB and XC independently represents a single bond, or a linear, or a branched divalent hydrocarbon group having 1 to 4 carbon atoms; YA represents a substituent having a lactone, sultone, hydroxy, carboxyl, ester, ether, carbonyl, amido, or cyano structure; ZA represents a hydrogen atom, or a fluoroalkyl group having 1 to 15 carbon atoms, or a fluoroalcohol-containing substituent having 1 to 15 carbon atoms; and $k^{1A}$ represents an integer of 1 to 3.

The polymer of the present invention containing such a repeating unit is suitable for various applications.

The polymer further contains any one or more kinds of repeating units represented by the following general formulae (d1) to (d3),

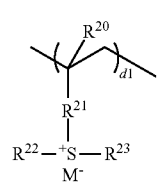

wherein each of $R^{20}$, $R^{24}$, and $R^{28}$ independently represents a hydrogen atom or a methyl group; $R^{21}$ represents a single bond, a phenylene group, —O—$R^{33}$—, or —C(=O)—Y—$R^{33}$—; Y represents an oxygen atom or NH; $R^{33}$ represents a linear, a branched, or a cyclic alkylene group having 1 to 6 carbon atoms, an alkenylene group, or a phenylene group, optionally containing a carbonyl group (—CO—), an ester group (—COO—), an ether group (—O—), or a hydroxy group; $R^{22}$, $R^{23}$, $R^{25}$, $R^{26}$, $R^{27}$, $R^{29}$, $R^{30}$ and $R^{31}$ represent the same or different linear, branched, or cyclic alkyl groups having 1 to 12 carbon atoms, optionally containing a carbonyl group, an ester group, or an ether group, aryl groups having 6 to 12 carbon atoms, aralkyl groups having 7 to 20 carbon atoms, or thiophenyl groups; $Z_0$ represents a single bond, a methylene group, an ethylene group, a phenylene group, a fluorinated phenylene group, —O—$R^{32}$—, or —C(=O)—$Z_1$—$R^{32}$—; $Z_1$ represents an oxygen atom or NH; $R^{32}$ represents a linear, a branched, or a cyclic alkylene group having 1 to 6 carbon atoms, an alkenylene group, or a phenylene group, optionally containing a carbonyl group, an ester group, an ether group, or a hydroxy group; and $M^-$ represents a non-nucleophilic counter ion.

When the polymer containing such a repeating unit is used to prepare a resist composition, the addition of an acid generator may be omitted. However, when such a polymer-type acid generator is contained, a resist composition can be used to form a very high-precision pattern.

The present invention further provides a resist composition containing the polymer as a base resin.

The resist composition can contain any one or more of an organic solvent and an acid generator.

A resist composition containing the polymer of the present invention as a base resin can have a high resolution and a reduced pattern edge roughness, and have a high transparency to an ArF excimer laser light.

Furthermore, a resist composition containing an organic solvent can have an improved coating property on substrates, and a resist composition containing an acid generator can have a higher sensitivity.

The present invention provides a patterning process including the steps of applying the resist composition to a substrate, performing exposure to a high-energy beam or an electron beam through a photomask after heat treatment, and performing development with a developer.

It is obvious that the development may be performed after exposure followed by heat treatment, and that other steps such as etching, resist-removing, and washing steps may also be performed.

In the development step, a non-exposed area of the resist film can be dissolved in a developer containing an organic solvent to form a negative pattern.

Even in the formation of a negative pattern using an organic solvent, the patterning process using the resist composition of the present invention increases the dissolution rate in the non-exposed area to improve contrast. Thus, a resolution power can be enhanced.

In the exposure step, a liquid having a high index of refraction of 1.0 or more can be placed between the resist film and a projection lens to perform immersion lithography.

In the patterning process using the resist composition of the present invention, the immersion lithography can be applied to form a finer pattern.

In the immersion lithography, a top coat can be further applied to the resist film, and a liquid having a high index of refraction of 1.0 or more can be placed between the top coat and a projection lens to perform immersion lithography.

The formed top coat can prevent a substance from eluting from the resist film to increase a water-sliding property of the film surface.

As described above, the polymerizable tertiary ester compound of the present invention has a trifluoromethyl group and a high transparency and contains a tertiary ester moiety represented by $R^2$, $R^3$ and Aa or by $R^2$ and Z. Thus, the tertiary ester moiety is easily eliminated to produce carboxylic acid. Therefore, the ester compound of the present invention can have both a high resolution and a reduced pattern edge roughness. For this reason, the ester compound of the present invention is particularly useful as a starting material for a functional material, and very useful as a monomer for production of a base resin of a radiation-sensitive resist composition having an excellent transparency to radiation having a wavelength of 500 nm or less, and especially 300 nm or less (e.g., KrF laser light, ArF laser light, and $F_2$ laser light) and a good development characteristic. Since the polymerizable tertiary ester compound of the present invention can be simply produced in high yield, it is used as a raw material to reduce the cost, and is efficient.

When a radiation-sensitive resist composition contains the polymer of the present invention, which contains the ester compound as a repeating unit, as a base resin, the resist composition can have excellent characteristics such as exposure dose dependence, density dependence, and mask fidelity, and a reduced pattern edge roughness. Therefore, the polymer is advantageously used in precise micropatterning as a base resin of a resist composition, especially a chemically amplified positive resist composition.

Even in the formation of a negative pattern using an organic solvent, the resist composition of the present invention can have an excellent resolution power by increasing the dissolution rate in the non-exposed area to improve contrast.

DETAILED DESCRIPTION OF THE PREFERRED EMBODIMENTS

Hereinafter, the present invention will be further described in greater detail.

As described above, in order to cope with a finer pattern rule by ArF excimer laser lithography and higher resolution by using an immersion lithography process, a fundamental improvement of line edge roughness is required without decreasing the resolution.

The present inventors have intensively studied to achieve the objects, and as a result, found the followings: A polymerizable tertiary ester compound represented by the following general formula (1a) or (1b) can be simply obtained in high yield; a resist composition using, as a base resin, a polymer having the ester compound as a repeating unit can have excellent characteristics such as exposure dose dependence, density dependence, and mask fidelity. Further, the resist composition can have a reduced pattern edge roughness by decreasing swelling in alkaline developing. Furthermore, the dissolution rate of the non-exposed area is increased in the formation of a negative pattern using an organic solvent to improve contrast, and thus a resolution power can be increased. The polymer is advantageously used in precise micropatterning as a resist composition, especially a chemically amplified resist composition. In addition, they have found that a polymer containing the ester compound as a repeating unit can be used as a resist additive to produce a resist film which can endure high speed scanning without a resist top coat and has a high water repellency and a high water-sliding property.

Accordingly, the present invention provides a polymerizable tertiary ester compound, a polymer, a resist composition, and a patterning process, described below.

Hereinafter, the present invention will be described in detail, but the present invention is not limited thereto.

Most of compounds of the following formulae may be in the form of enantiomer or diastereomer. Unless otherwise noted, each formula typifies all the stereoisomers thereof in all cases. Moreover, the stereoisomers may be used alone or in a mixture.

The polymerizable tertiary ester compound of the present invention is represented by the following general formula (1a) or (1b),

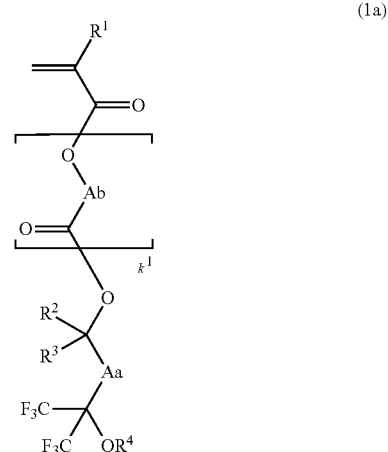

(1a)

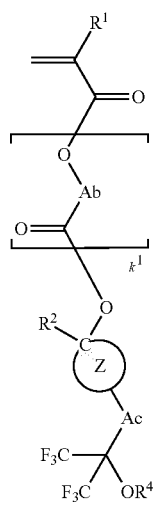

wherein $R^1$ represents a hydrogen atom, a fluorine atom, a methyl group, or a trifluoromethyl group; $R^2$ and $R^3$ represent a linear, a branched, or a cyclic monovalent hydrocarbon group having 1 to 15 carbon atoms, or $R^2$ and $R^3$ may combine with each other to form a non-aromatic ring having 3 to 8 carbon atoms together with the carbon atoms to which they are bonded; Z represents a divalent group forming a substituted or an unsubstituted cyclopropane, cyclobutane, cyclopentane, cyclohexane, or norbornane ring together with the carbon atom to which it is bonded; Aa represents a linear, a branched, or a cyclic divalent hydrocarbon group having 1 to 10 carbon atoms; Ab represents a linear, a branched, or a cyclic divalent hydrocarbon group having 1 to 6 carbon atoms; Ac represents a direct bond or a linear, a branched, or a cyclic divalent hydrocarbon group having 1 to 10 carbon atoms; $R^4$ represents a hydrogen atom, or a linear, a branched, or a cyclic monovalent hydrocarbon group having 1 to 15 carbon atoms, and when $R^4$ is a monovalent hydrocarbon group, —$CH_2$— is substituted with —O— or —C(=O)—; and $k^1$ is 0 or 1.

In the general formulae (1a) and (1b), specific examples of the used linear, branched, or cyclic monovalent hydrocarbon group having 1 to 15 carbon atoms of $R^2$ and $R^3$ may include a methyl group, an ethyl group, a n-propyl group, an isopropyl group, a n-butyl group, a sec-butyl group, a tert-butyl group, a tert-amyl group, a n-pentyl group, a n-hexyl group, a n-heptyl group, a n-octyl group, a n-nonyl group, a n-decyl group, a cyclopentyl group, a cyclohexyl group, a cyclopentylmethyl group, a cyclopentylethyl group, a cyclopentylbutyl group, a cyclohexylmethyl group, a cyclohexylethyl group, a cyclohexylbutyl group, and an adamantyl group. $R^2$ and $R^3$ can combine with each other to form a non-aromatic ring having 3 to 8 carbon atoms. In this case, $R^2$ and $R^3$ are an alkylene group, which is obtained by removing one hydrogen atom from the alkyl group as exemplified above. Specific examples of the ring may include a cyclopentyl group and a cyclohexyl group.

As a monovalent hydrocarbon group of $R^4$, various protecting groups of alcoholic hydroxyl group can be used. Specific examples thereof may include groups represented by the following general formulae (R1-1) and (R1-2), a tertiary alkyl group having 4 to 20 carbon atoms, and preferably 4 to 15 carbon atoms, a trialkylsilyl group of which alkyl groups each have 1 to 5 carbon atoms, an oxoalkyl group having 4 to 15 carbon atoms, and an acyl group having 1 to 10 carbon atoms.

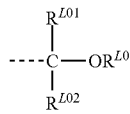

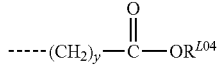

In the formulae, the broken line represents an atomic bonding (hereinafter as the same). y represents an integer of 0 to 6. $R^{L01}$ and $R^{L02}$ represent a hydrogen atom, or a linear, a branched, or a cyclic alkyl group having 1 to 18 carbon atoms, and preferably 1 to 10 carbon atoms. Specific examples thereof may include a methyl group, an ethyl group, a propyl group, an isopropyl group, a n-butyl group, a sec-butyl group, a tert-butyl group, a cyclopentyl group, a cyclohexyl group, a 2-ethylhexyl group, a n-octyl group, a norbornyl group, a tricyclodecanyl group, a tetracyclododecanyl group, and an admantyl group. $R^{L03}$ represents a monovalent hydrocarbon group having 1 to 18 carbon atoms, and preferably 1 to 10 carbon atoms, and optionally having a hetero atom such as an oxygen atom, for example, a linear, a branched, or a cyclic alkyl group, in which some hydrogen atoms are replaced by a hydroxyl group, an alkoxy group, an oxo group, an amino group, or an alkylamino group. Specific examples thereof may include substituted alkyl groups described below.

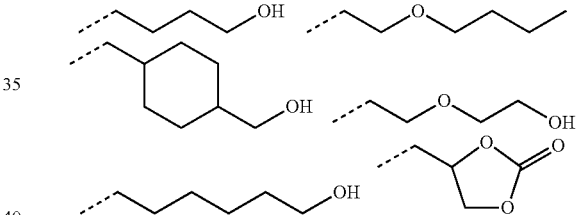

$R^{L01}$ and $R^{L02}$, $R^{L01}$ and $R^{L03}$, $R^{L02}$ and $R^{L03}$ may combine with each other to form a ring with a carbon atom and an oxygen atom to which they are bound. When a ring is formed, each of $R^{L01}$, $R^{L02}$, and $R^{L03}$ involved in the formation of the ring represents a linear or a branched alkylene group having 1 to 18 carbon atoms, and preferably 1 to 10 carbon atoms.

$R^{L04}$ is a tertiary alkyl group having 4 to 20 carbon atoms, and preferably 4 to 15 carbon atoms, a trialkylsilyl group of which each alkyl group has 1 to 5 carbon atoms, an oxoalkyl group having 4 to 15 carbon atoms, or a group represented by the general formula (R1-1).

Specific examples of the tertiary alkyl group in $R^4$ or $R^{L04}$ may include a tert-butyl group, a tert-amyl group, a 1,1-diethylpropyl group, a 2-cyclopentylpropan-2-yl group, a 2-cyclohexylpropan-2-yl group, a 2-(bicyclo[2.2.1]heptan-2-yl)propan-2-yl group, a 2-(adamantan-1-yl)propan-2-yl group, a 1-ethylcyclopentyl group, a 1-butylcyclopentyl group, a 1-ethylcyclohexyl group, a 1-butylcyclohexyl group, a 1-ethyl-2-cyclopentenyl group, a 1-ethyl-2-cyclohexenyl group, a 2-methyl-2-adamantyl group, and a 2-ethyl-2-adamantyl group. Specific examples of the trialkylsilyl group may include a trimethylsilyl group, a triethylsilyl group, and a dimethyl-tert-butylsilyl group. Specific examples of the oxoalkyl group may include a 3-oxocyclohexyl group, a 4-methyl-2-oxooxan-4-yl group, and a 5-methyl-2-oxooxolan-5-yl group. Specific examples of the acyl group may include a formyl group, an acetyl group, an ethylcarbonyl group, a pivaloyl group, a methoxycarbonyl group, an ethoxycarbonyl group, a tert-buthoxycarbonyl group, a trifluoroacetyl group, and a trichloroacetyl group.
Of the protecting groups represented by the formula (R1-1), linear and branched groups are specifically as follows.
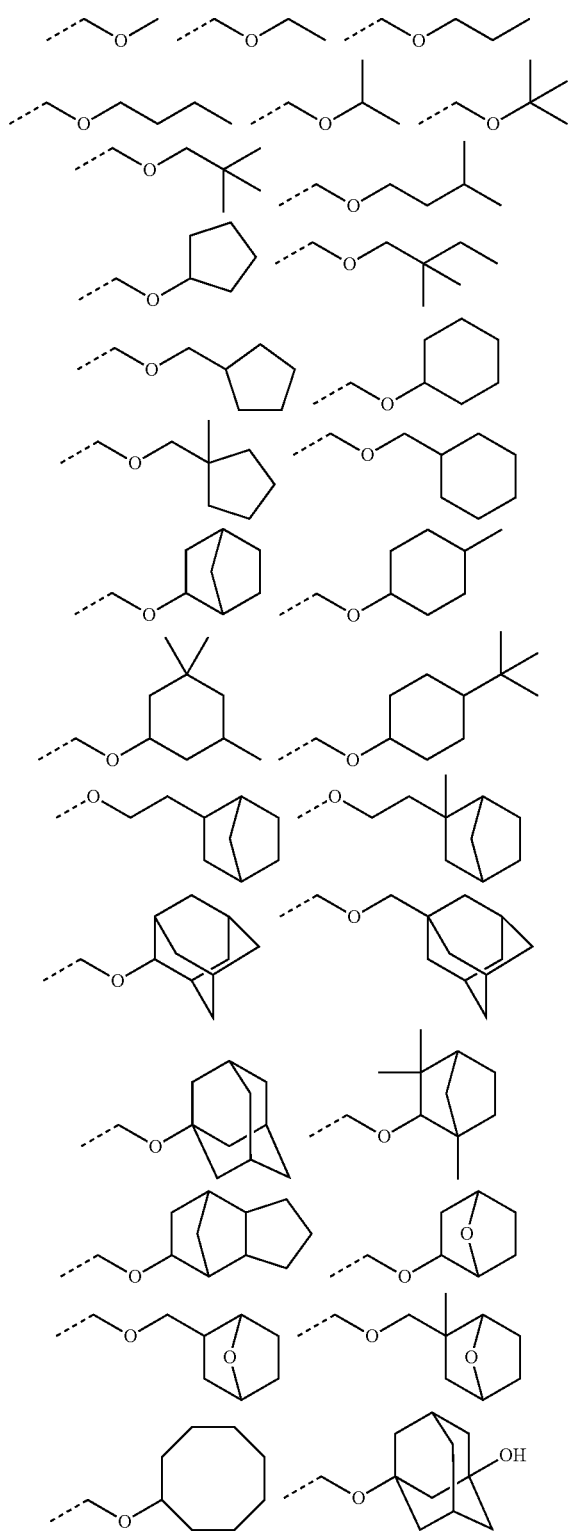
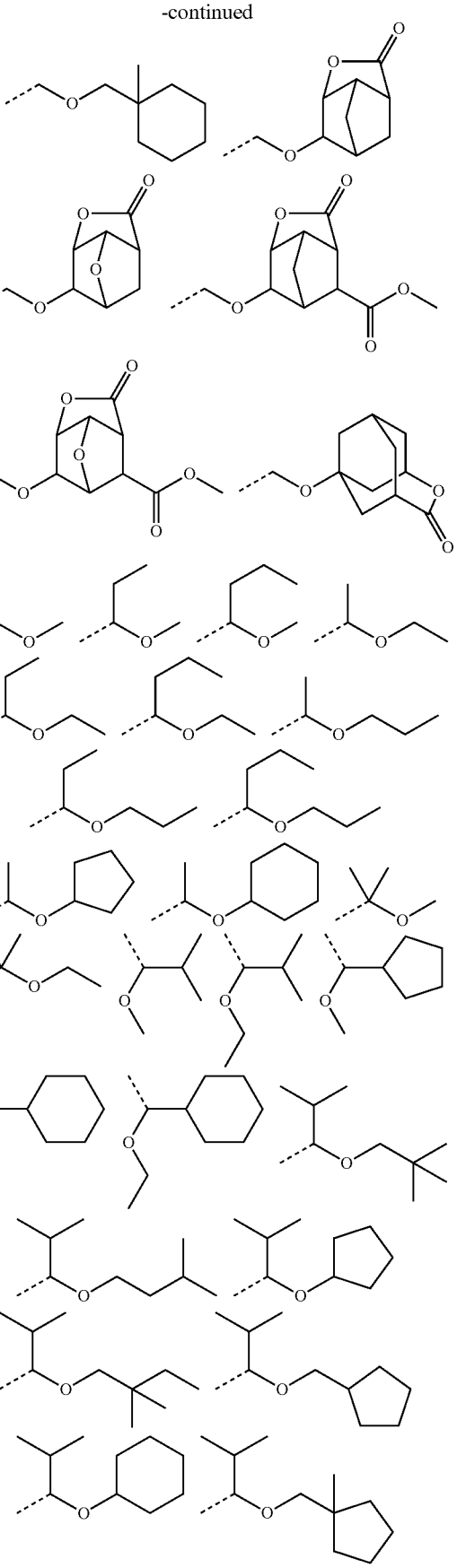

-continued

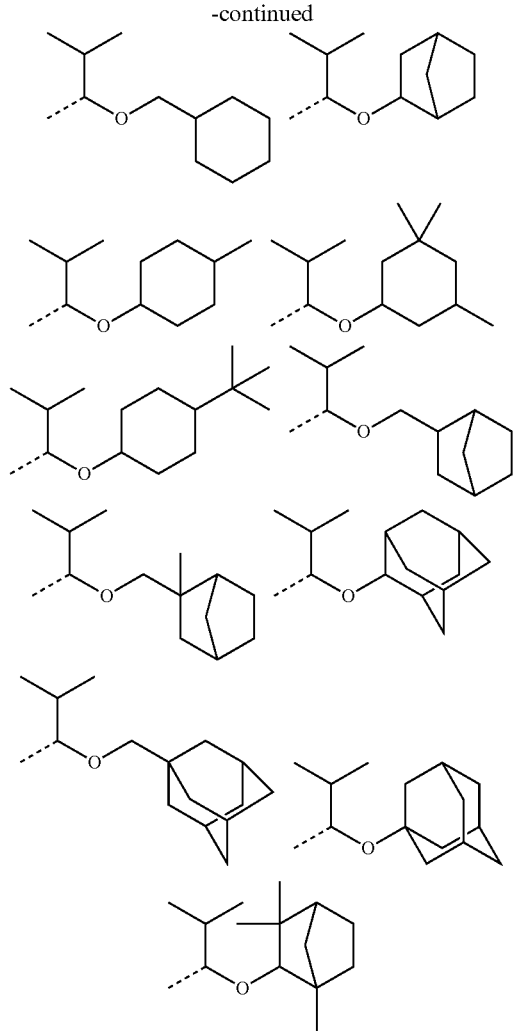

Examples of cyclic groups of the protecting groups of the formula (R1-1) may include a tetrahydrofuran-2-yl group, a 2-methyltetrahydrofuran-2-yl group, a tetrahydropyran-2-yl group, and a 2-methyltetrahydropyran-2-yl group.

Specific examples of the protecting groups of the formula (R1-2) may include a tert-buthoxycarbonyl group, a tert-buthoxycarbonylmethyl group, a tert-amyloxycarbonyl group, a tert-amyloxycarbonylmethyl group, a 1,1-diethylpropyloxycarbonyl group, a 1,1-diethylpropyloxycarbonylmethyl group, a 1-ethylcyclopentyloxycarbonyl group, a 1-ethylcyclopentyloxycarbonylmethyl group, a 1-ethyl-2-cyclopentenyloxycarbonyl group, a 1-ethyl-2-cyclopentenyloxycarbonylmethyl group, a 1-ethoxyethoxycarbonylmethyl group, a 2-tetrahydropyranyloxycarbonylmethyl group, and a 2-tetrahydrofuranyloxycarbonylmethyl group.

Specific examples of the linear, branched, or cyclic divalent hydrocarbon group having 1 to 10 carbon atoms of Aa and Ac may be the following groups.

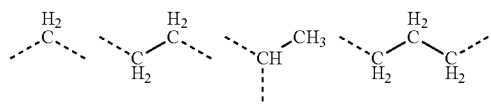

-continued

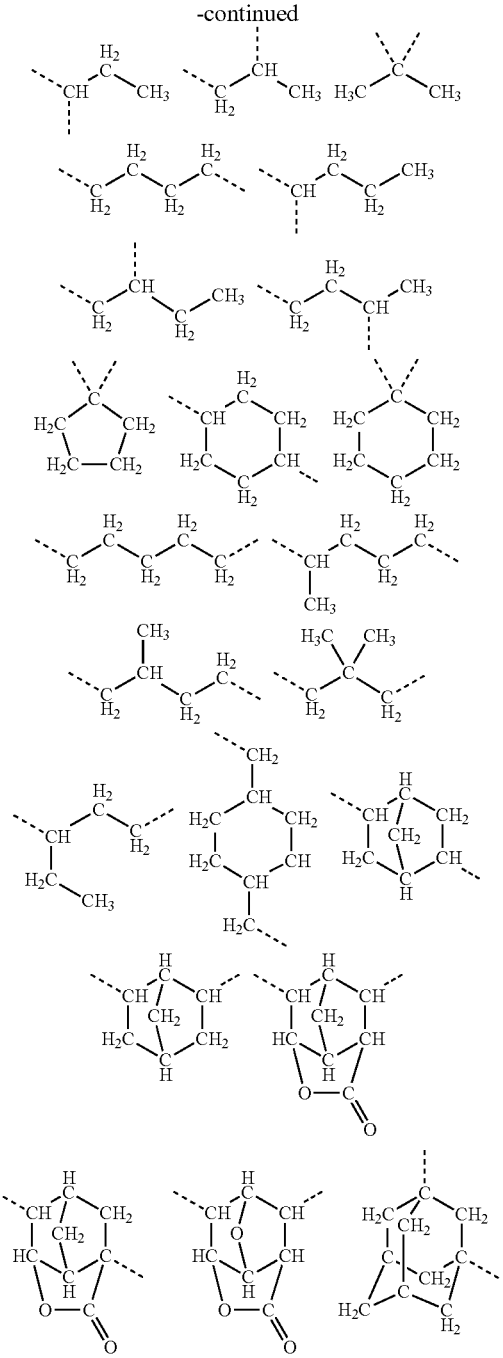

Examples of the linear, branched, or cyclic divalent hydrocarbon group having 1 to 6 carbon atoms of Ab may include an alkylene group, and specifically the following groups.

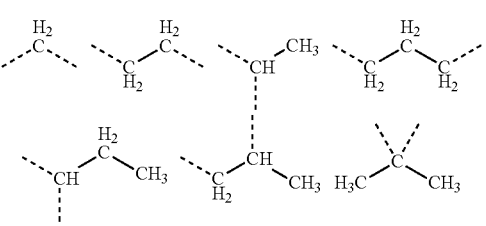

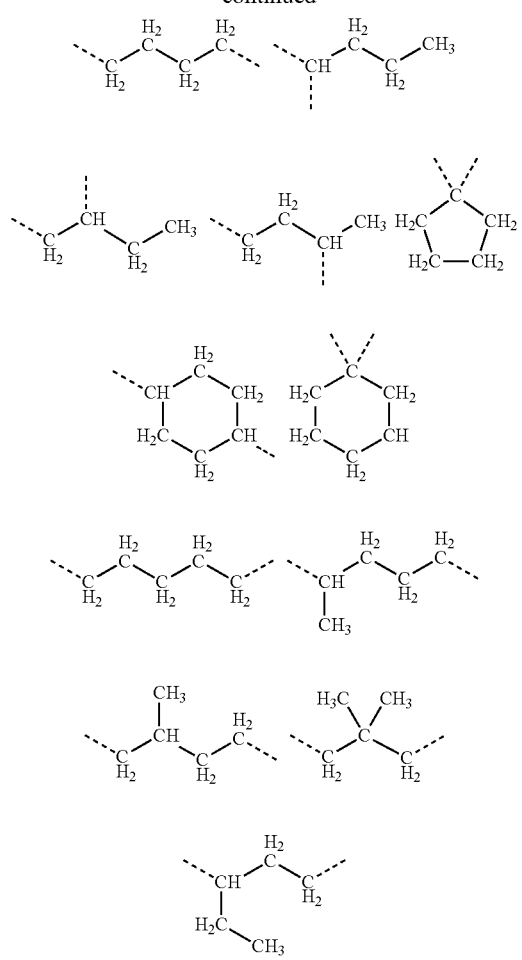
Specific examples of the compounds represented by the general formulae (1a) and (1b) may be as follows,
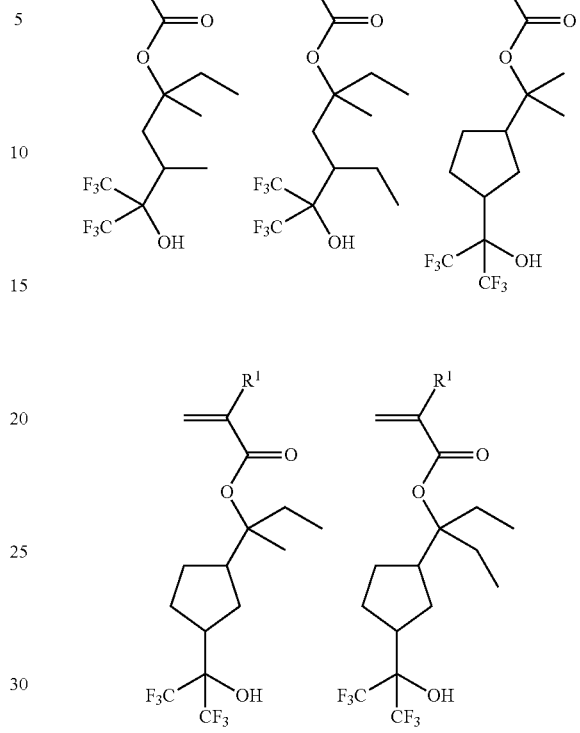
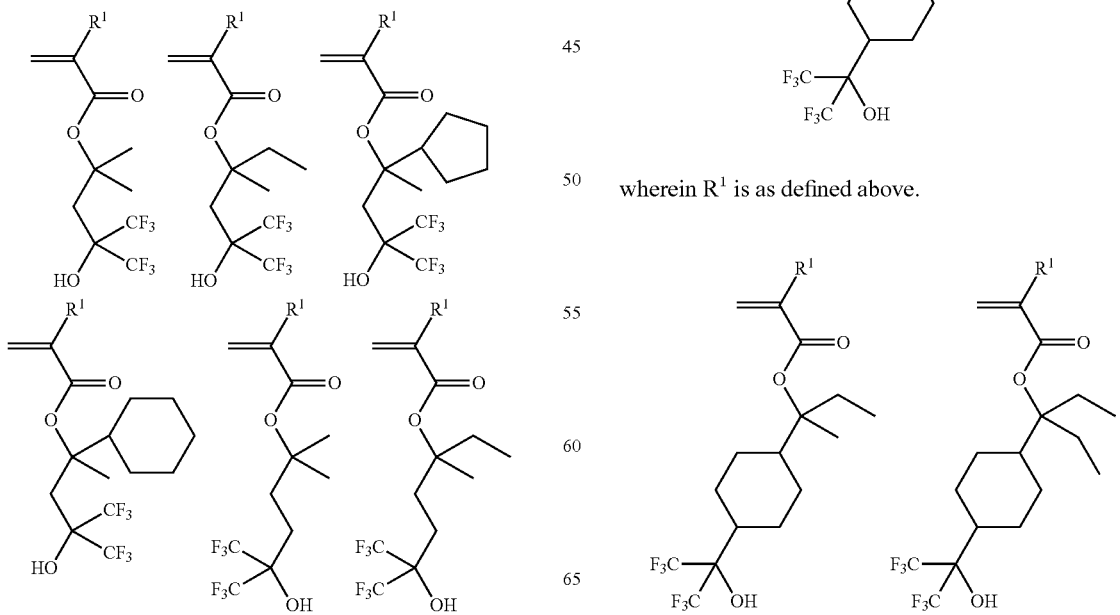
wherein $R^1$ is as defined above.

-continued
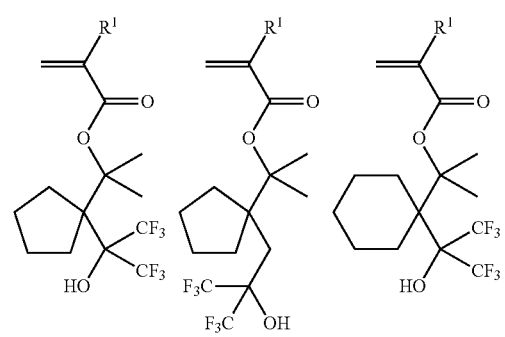
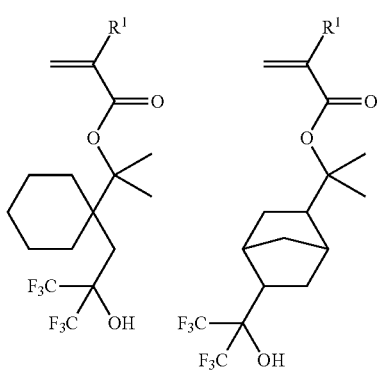
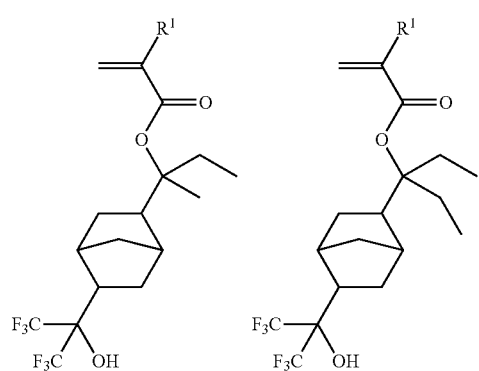
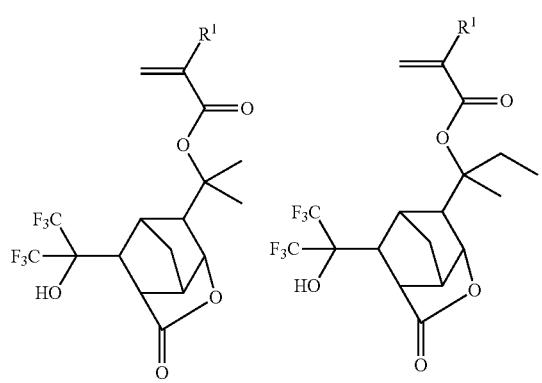
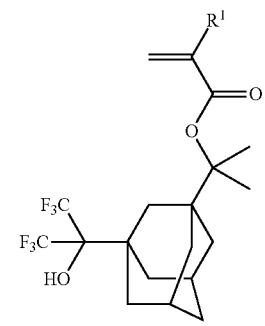
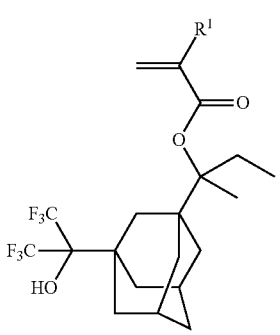
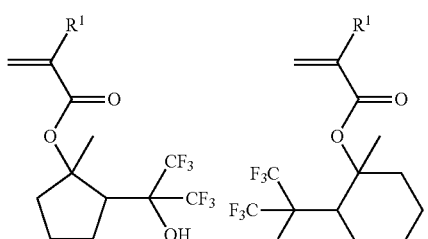
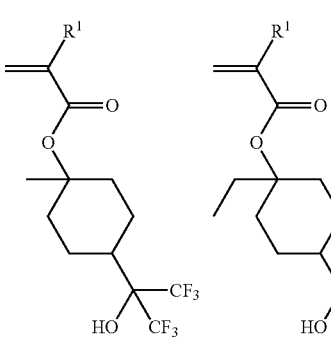
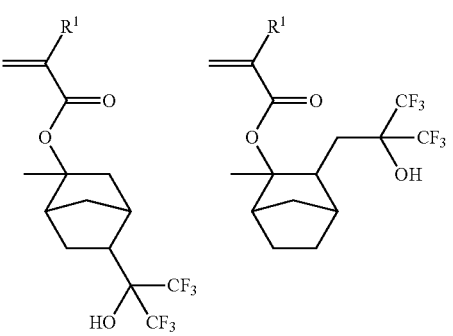
wherein R¹ is as defined above.

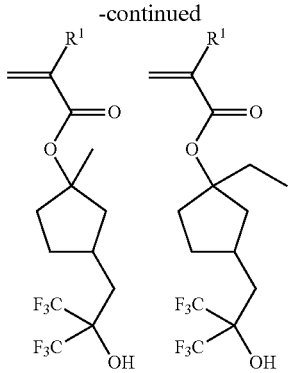
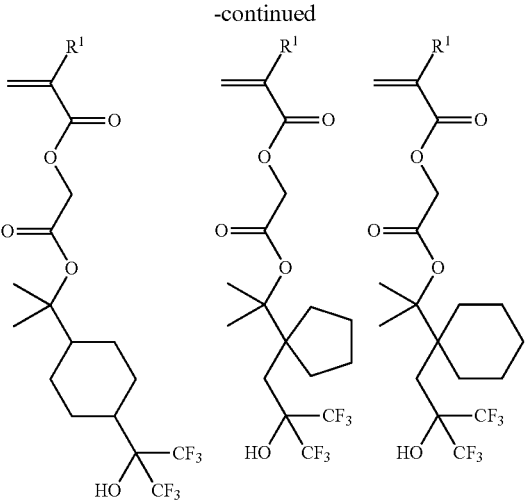
wherein R¹ is as defined above.
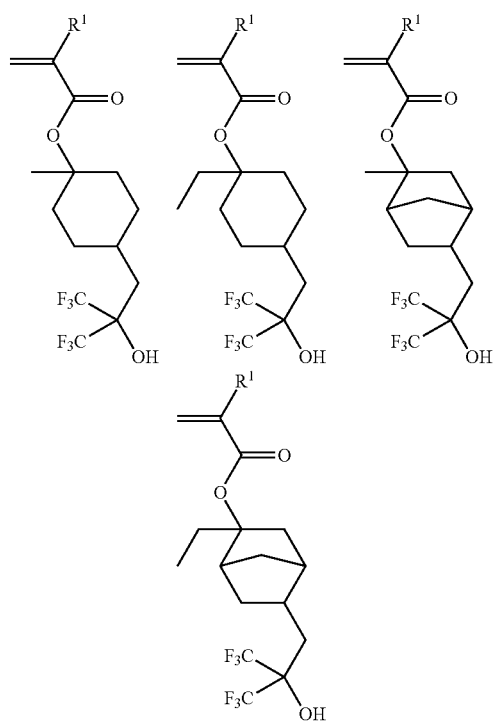
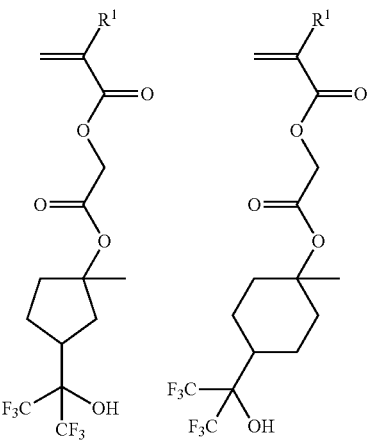
wherein R¹ is as defined above.
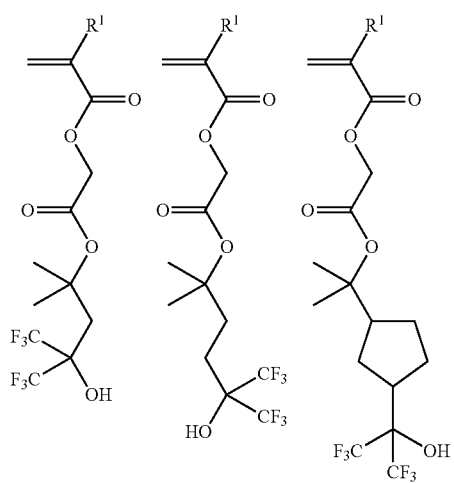

-continued
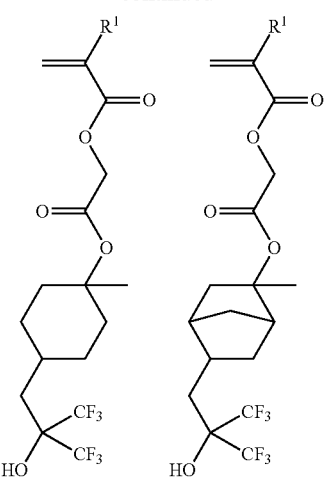
wherein R¹ is as defined above.
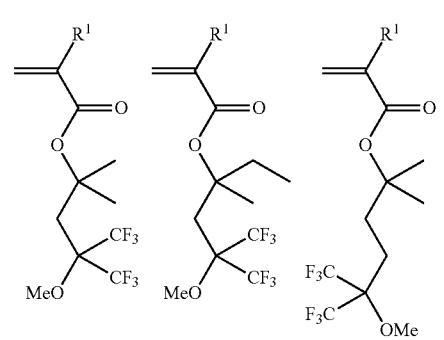
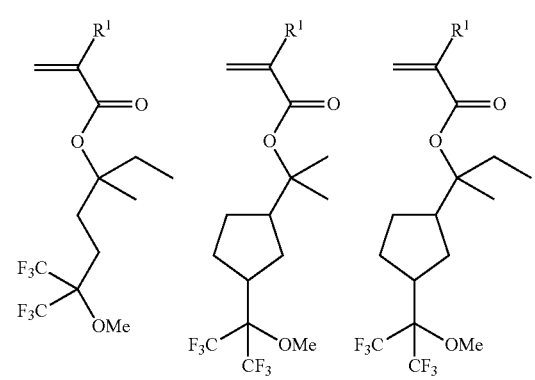
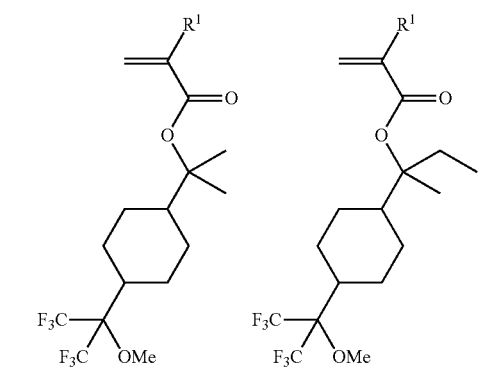
-continued
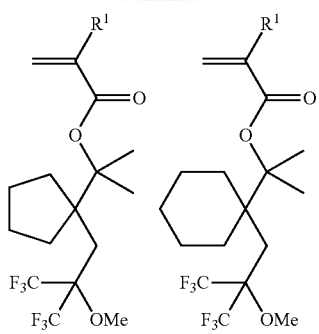
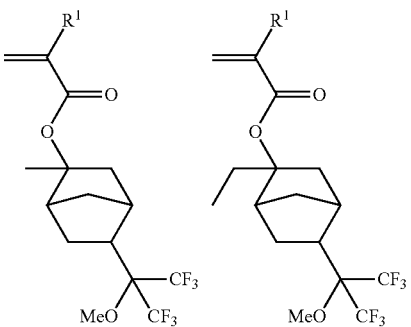
wherein R¹ is as defined above.
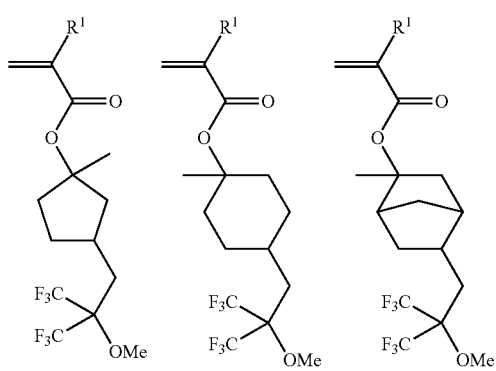

-continued
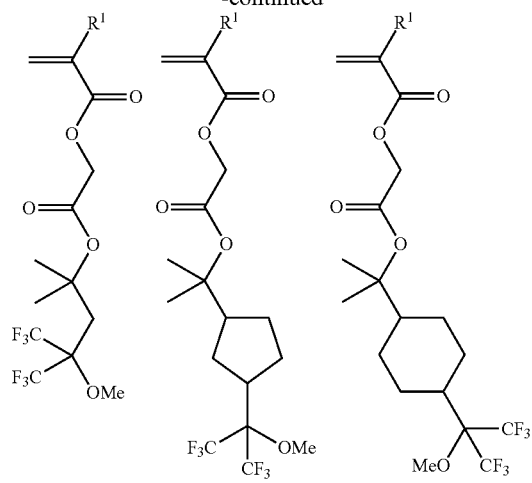
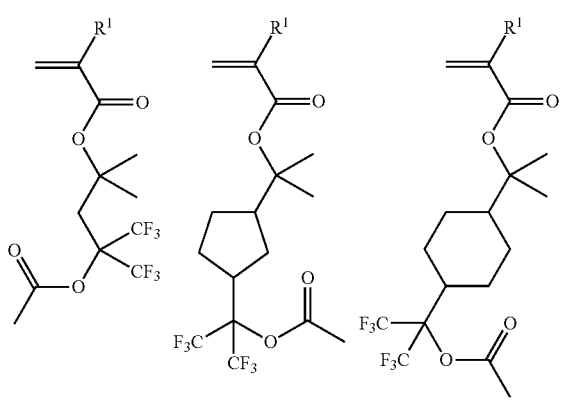
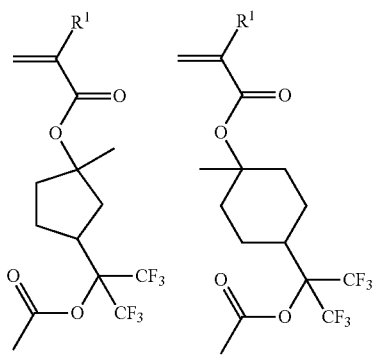
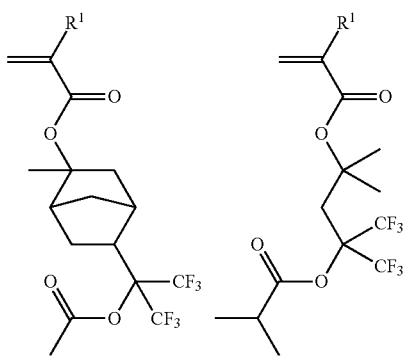
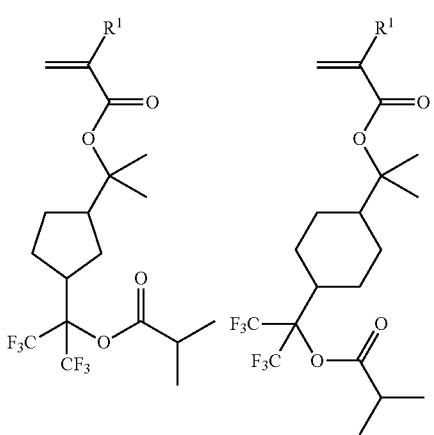
wherein R¹ is as defined above.

-continued
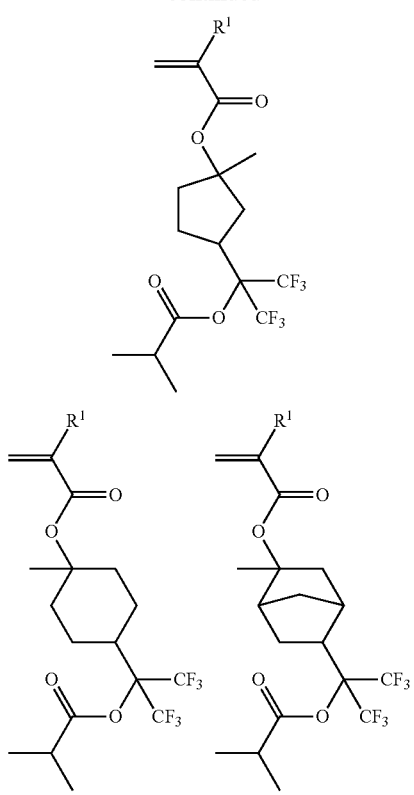
wherein R¹ is as defined above.
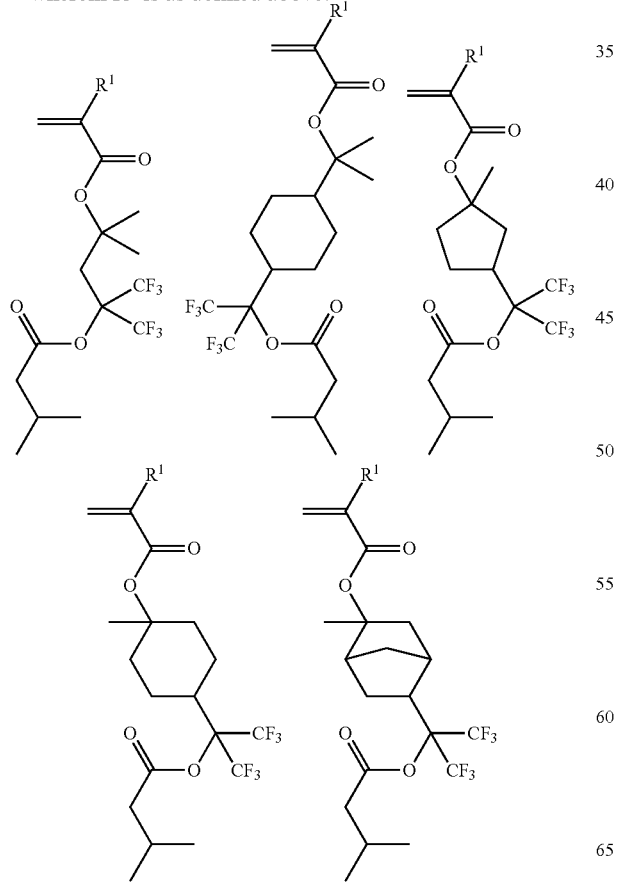
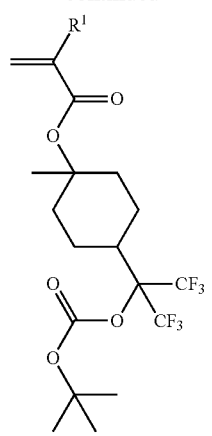
wherein R¹ is as defined above.
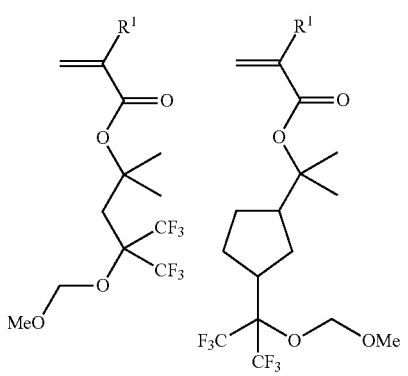
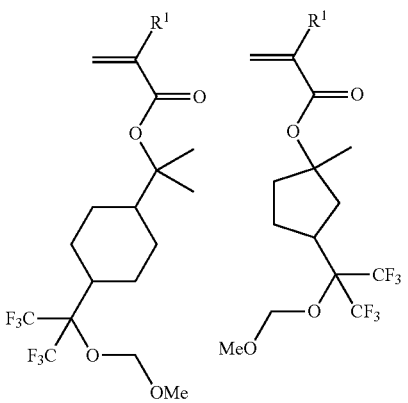
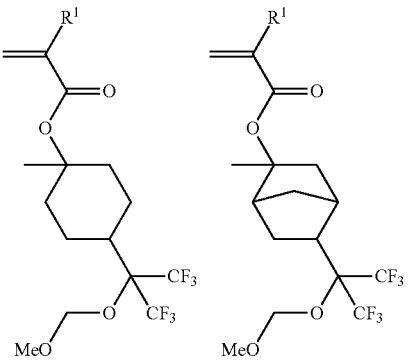

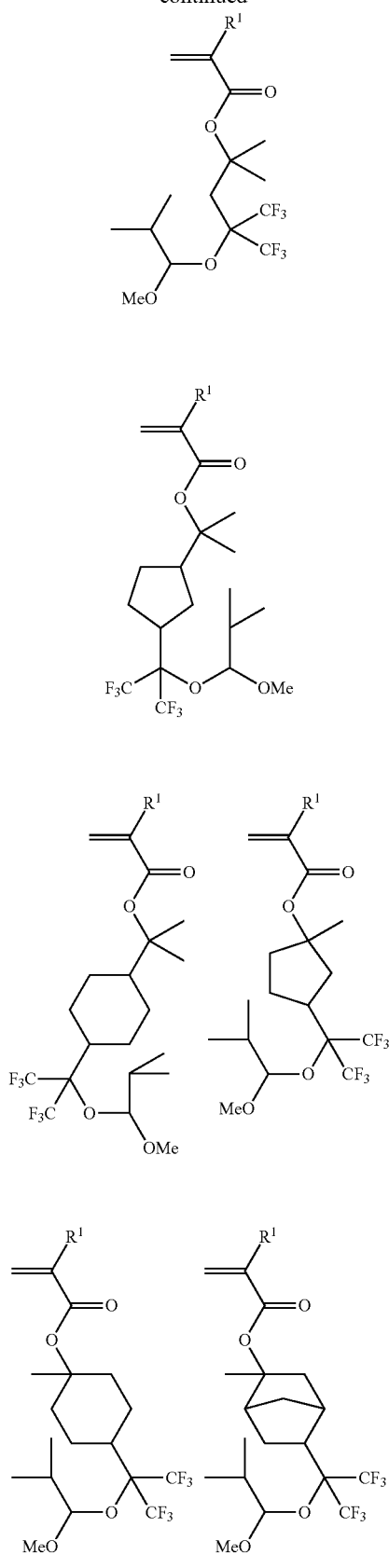
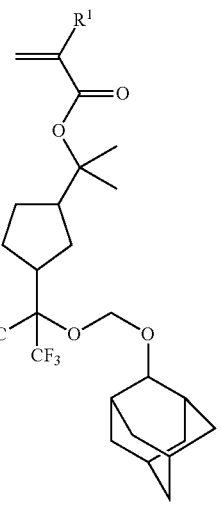
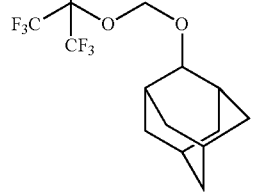
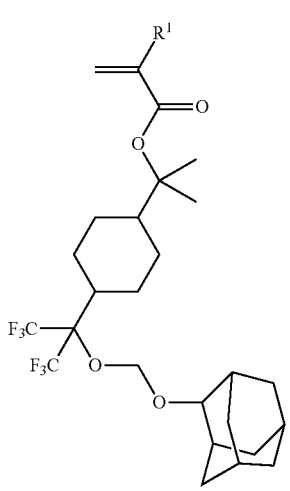
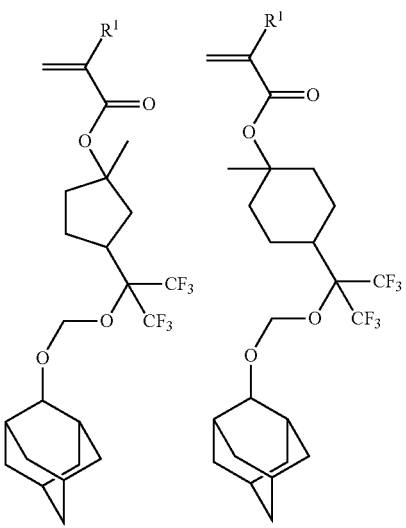
wherein R¹ is as defined above.

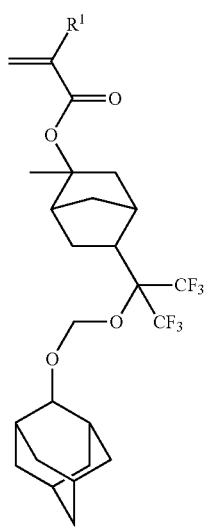

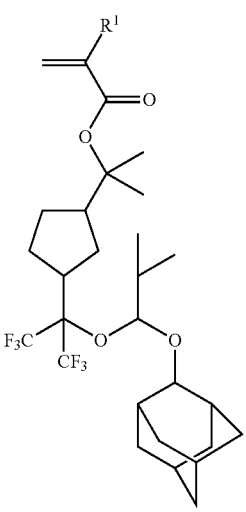

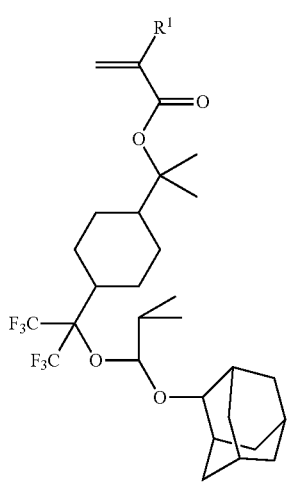

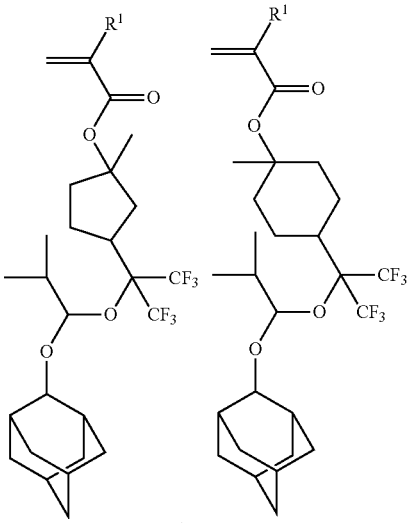

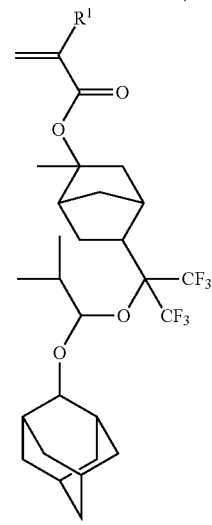

wherein R¹ is as defined above.

Of the above-describes compounds, it is particularly preferable that any one or more of groups corresponding to $R^2$, $R^3$, and Aa have a cyclic structure when they are used as a starting material for a functional material.

The polymerizable tertiary ester compound of the present invention represented by the general formula (1a) or (1b) can be obtained by the following reaction schemes i) to iv). However, the present invention is not limited to the schemes.

A case where k=0 will be first described,

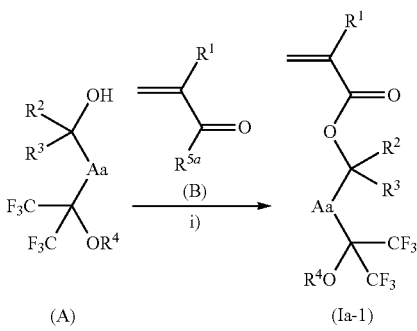

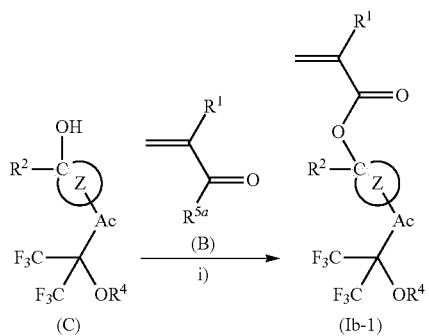

wherein $R^1$, $R^2$, $R^3$, $R^4$, Aa, Ac, and Z are as defined above; $R^{5a}$ represents a halogen atom, a hydroxyl group, or —$OR^{6a}$; and $R^{6a}$ represents a methyl group, an ethyl group, or a group represented by the following formula (D-1).

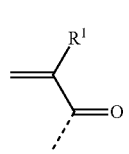

(D-1)

When $R^4$ is an hydrogen atom, an alcohol adjacent to a trifluoromethyl group may be more selectively esterified as compared with an alcohol adjacent to $R^2$. In this case, after both the alcohols are esterified as shown in the following reaction formulae, the alcohol adjacent to a trifluoromethyl group may be deprotected,

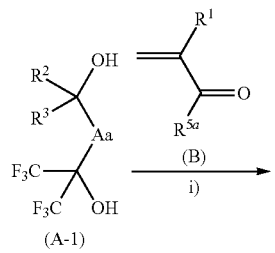

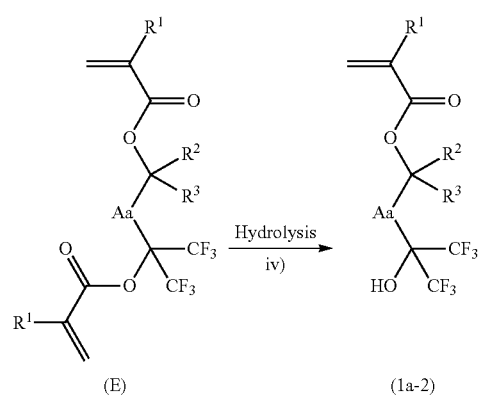

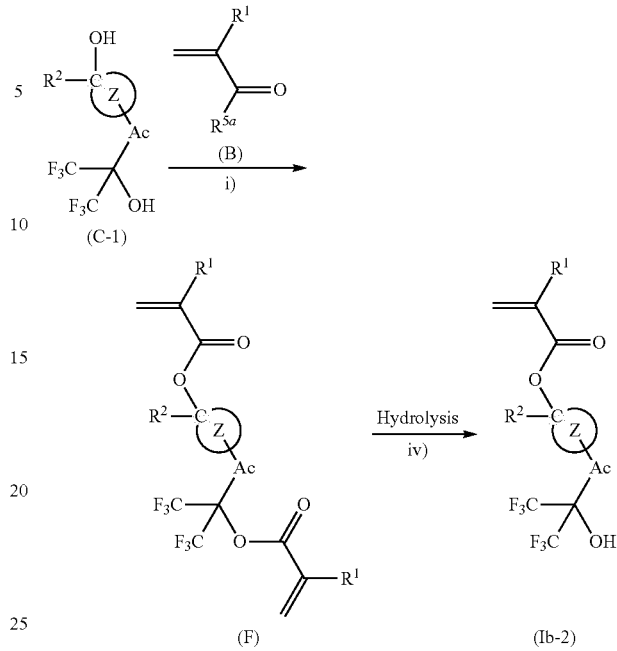

wherein $R^1$, $R^2$, $R^3$, $R^4$, $R^{5a}$, Aa, Ac, and Z are as defined above.

Step i) is a reaction of an esterifying agent (B) with an alcohol compound (A) or (C) to form a fluorine-containing monomer (1a-1) or (1b-1).

When $R^4$ is a hydrogen atom, it is preferable that step i) be a reaction of two or more equivalents of esterifying agent (B) with a diol compound (A-1) or (C-1) to form a fluorine-containing monomer having esterified alcohols (E) or (F).

The reaction may readily proceed by a known process. It is preferable that the esterifying agent (B) be an acid chloride when $R^{5a}$ in the formula (B) is a chlorine atom or a carboxylic acid anhydride when $R^{5a}$ represents formula (D-1).

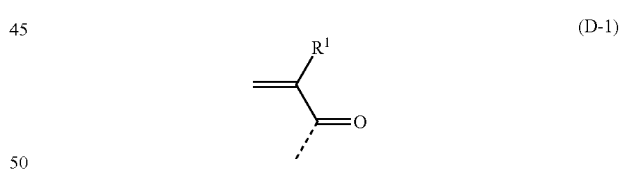

When an acid chloride is used, the alcohol compound (A) or (C) or the diol compound (A-1) or (C-1), the corresponding acid chloride such as methacrylic acid chloride or methacryloyloxyacetic acid chloride, and a base such as triethylamine, pyridine, or 4-dimethylaminopyridine are successively or simultaneously added to a solvent-free system or to a solvent such as methylene chloride, acetonitrile, toluene, or hexane while the reaction system may be cooled or heated if necessary. When a carboxylic acid anhydride is used, the alcohol compound (A) or (C) or the diol compound (A-1) or (C-1), and the corresponding carboxylic acid anhydride such as methacrylic acid anhydride or methacryloyloxyacetic acid anhydride may be reacted in a solvent such as toluene or hexane in the presence of an acid catalyst while the reaction system may be heated if necessary. Examples of an acid catalyst to be used may include inorganic acids such as hydrochloric acid, sulfuric acid, nitric acid, and perchloric acid, and organic acids such as methanesulfonic acid, trifluoromethanesulfonic acid, p-toluenesulfonic acid, and benzenesulfonic acid.

Step iv) is a selective hydrolysis reaction of a bis-ester compound (E) or (F), in which only an ester on the side adjacent to a trifluoromethyl group having a higher acidity is selectively hydrolyzed to form a fluorine-containing monomer (1a-2) or (1b-2).

The reaction may readily proceed by a known process. For example, a NaOH aqueous solution can be used as a hydrolysis reagent. The use amount of NaOH is preferably 0.5 to 2.0 mole, and particularly preferably 1.0 to 1.1 mole based on the bis-ester compound (E) or (F). The reaction can be carried out in a solvent-free system or in a solvent. As a solvent, ethers such as 1,4-dioxane, diglyme, or triglyme, or alcohols such as 2-methyl-2-propanol can be used.

A case where k=1 will be then described,

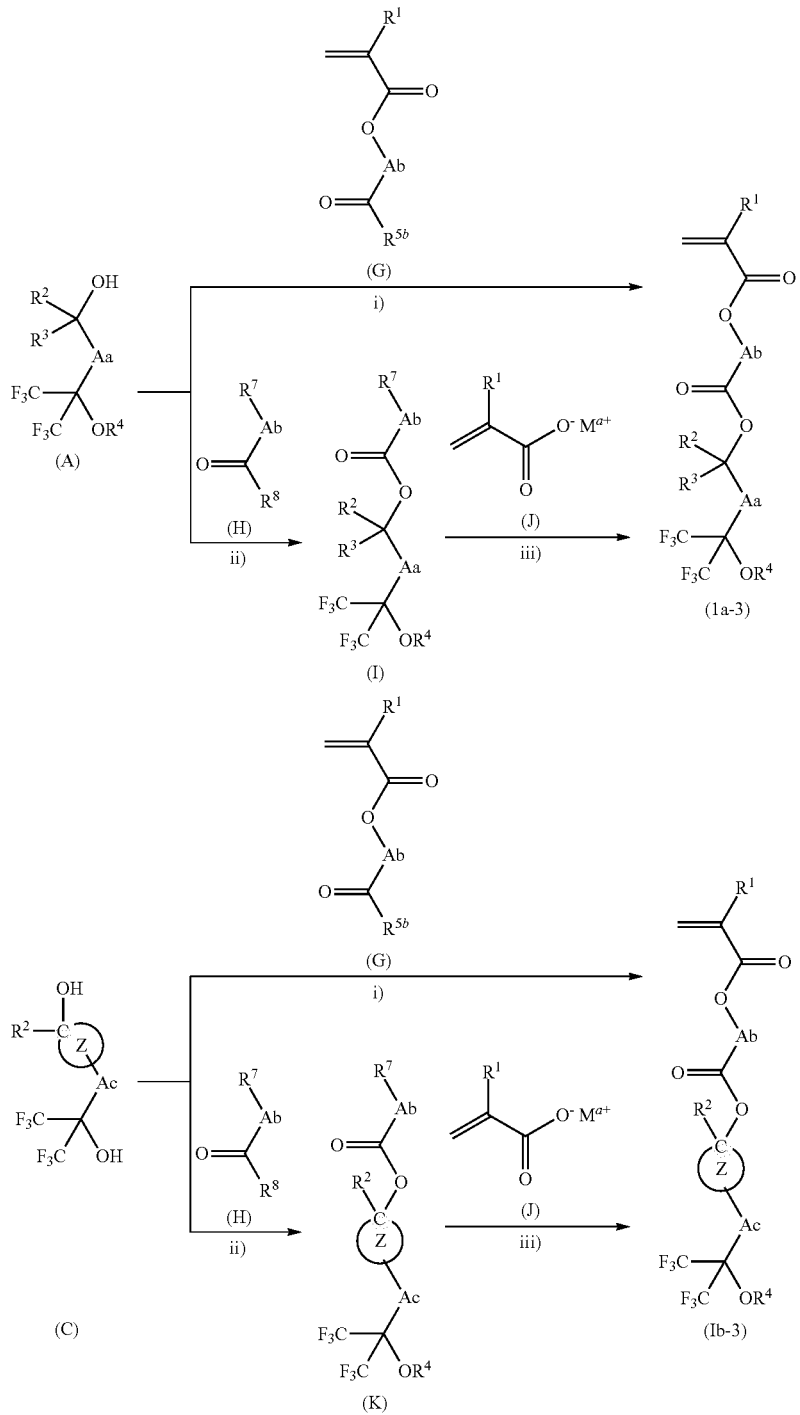

wherein $R^1$, $R^2$, $R^3$, $R^4$, Aa, Ab, Ac, and Z are as defined above; $R^{5b}$ represents a halogen atom, a hydroxyl group, or —$OR^{6b}$; $R^{6b}$ represents a methyl group, an ethyl group, or a group represented by the following formula (D-2),

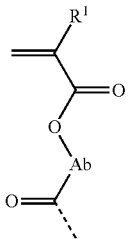

(D-2)

wherein $R^1$ and Ab are as defined above; $R^7$ represents a halogen atom; $R^8$ represents a halogen atom, a hydroxyl group, or —$OR^9$; $R^9$ represents a methyl group, an ethyl group, or a group represented by the following formula (L),

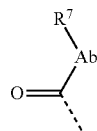

(L)

wherein $R^7$ and Ab are as defined above; and $M^a$ represents Li, Na, K, $Mg_{1/2}$, $Ca_{1/2}$, or substituted or unsubstituted ammonium.

When $R^4$ is a hydrogen atom, an alcohol adjacent to a trifluoromethyl group may be more selectively esterified as compared with an alcohol adjacent to $R^2$. In this case, both the alcohols are esterified as shown in the following reaction formula, and then the alcohol adjacent to a trifluoromethyl group may be deprotected,

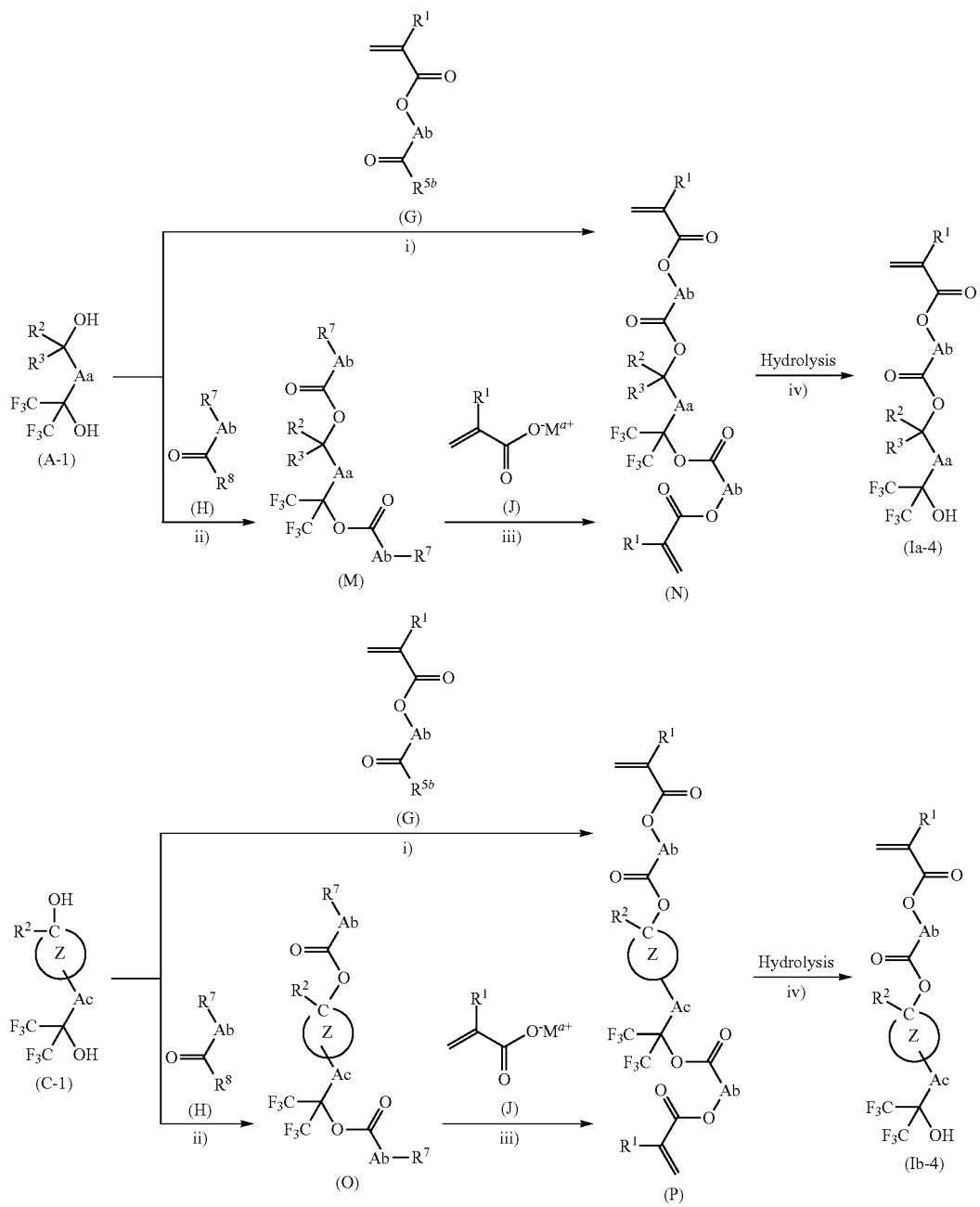

wherein $R^1$, $R^2$, $R^3$, $R^{5b}$, $R^7$, $R^8$, Aa, Ab, Ac, Z, and $M^a$ are as defined above.

Step i) is a reaction of an esterifying agent (G) with an alcohol compound (A) or (C) to form a fluorine-containing monomer (1a-3) or (1b-3).

When $R^4$ is a hydrogen atom, it is preferable that step i) be a reaction of two or more equivalents of esterifying agent (G) with a diol compound (A-1) or (C-1) to form a fluorine-containing monomer having esterified alcohols (N) or (P).

The reaction may readily proceed by a known process. It is preferable that the esterifying agent (G) be an acid chloride when $R^{5b}$ in the formula (G) is a chlorine atom or a carboxylic acid anhydride when $R^{5b}$ represents the following formula (D-2):

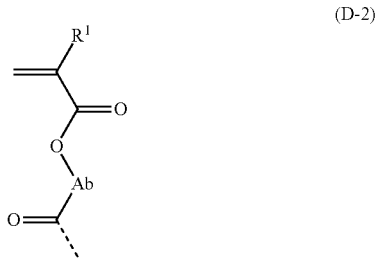

When an acid chloride is used, the alcohol compound (A) or (C) or the diol compound (A-1) or (C-1), the corresponding acid chloride such as methacrylic acid chloride or methacryloyloxyacetic acid chloride, and a base such as triethylamine, pyridine, or 4-dimethylaminopyridine are successively or simultaneously added to a solvent-free system or to a solvent such as methylene chloride, acetonitrile, toluene, or hexane, and the reaction system may be cooled or heated if necessary. When a carboxylic acid anhydride is used, the alcohol compound (A) or (C) or the diol compound (A-1) or (C-1), and the corresponding carboxylic acid anhydride such as methacrylic acid anhydride or methacryloyloxyacetic acid anhydride may be heated in a solvent such as toluene or hexane in the presence of an acid catalyst if necessary. Examples of an acid catalyst to be used may include inorganic acids such as hydrochloric acid, sulfuric acid, nitric acid, and perchloric acid, and organic acids such as methanesulfonic acid, trifluoromethanesulfonic acid, p-toluenesulfonic acid, and benzenesulfonic acid.

Step ii) is a reaction of an esterifying agent (H) with an alcohol compound (A) or (C) to form a halo ester compound (I) or (K).

When $R^4$ is a hydrogen atom, it is preferable that step ii) be a reaction of two or more equivalents of esterifying agent (H) with a diol compound (A-1) or (C-1) to form a halo ester compound (M) or (O).

The reaction may readily proceed by a known process. It is preferable that the esterifying agent (H) be an acid chloride when $R^8$ in formula (H) is a chlorine atom, or a carboxylic acid when $R^8$ is a hydroxyl group. When an acid chloride is used, the alcohol compound (A) or (C) or the diol compound (A-1) or (C-1), the corresponding acid chloride such as 2-chloroacetic acid chloride or 4-chlorobutyric acid chloride, and a base such as triethylamine, pyridine, or 4-dimethylaminopyridine are successively or simultaneously added to a solvent-free system or to a solvent such as methylene chloride, toluene, hexane, diethyl ether, tetrahydrofuran, or acetonitrile, and the reaction system may be cooled or heated if necessary. When a carboxylic acid is used, the alcohol compound (A) or (C) or the diol compound (A-1) or (C-1), and the corresponding carboxylic acid such as 2-chloroacetic acid or 4-chlorobutyric acid are heated in a solvent such as toluene or hexane in the presence of an acid catalyst while generated water may be removed out of the system if necessary. Examples of an acid catalyst to be used may include inorganic acids such as hydrochloric acid, sulfuric acid, nitric acid, and perchloric acid, and organic acids such as p-toluenesulfonic acid and benzenesulfonic acid.

Step iii) is a reaction of a halo ester compound (I) or (K) with a carboxylate salt compound (J) to form a fluorine-containing monomer (1a-3) or (1b-3).

When $R^4$ is a hydrogen atom, step iii) is a reaction of a halo ester compound (M) or (O) with a carboxylate salt compound (J), preferably in an amount of two or more equivalents, to form a fluorine-containing monomer having substituted moieties (N) or (P).

The reaction may readily proceed by a known process. As the carboxylate salt compound (J), commercially available carboxylate salt compounds, such as various carboxylic acid metal salts, may be used as they are. Alternatively, a carboxylate salt compound may be prepared by reaction of the corresponding carboxylic acid such as methacrylic acid or acrylic acid with a basic in a reaction system and be used. When a halo ester compound as a raw material is (I) or (K), the use amount of the carboxylate salt compound (J) is preferably 0.5 to 10 mole, and particularly preferably 1.0 to 3.0 mole per mole of the halo ester compound. When the use amount is 0.5 mole or more, the yield can be increased. When the use amount is 10 mole or less, the reaction is advantageous in terms of a cost without increasing a material cost and reducing a pot yield. On the other hand, when a halo ester compound as a raw material is (M) or (O), the use amount of the carboxylate salt compound (J) is preferably two times than the above-describes use amount. A base capable of being used to prepare a carboxylate salt compound from the corresponding carboxylic acid and the base in a reaction system is selected from amines such as ammonia, triethylamine, pyridine, lutidine, collidine, and N,N-dimethylaniline; hydroxides such as sodium hydroxide, potassium hydroxide, and tetramethylammonium hydroxide; carbonate such as potassium carbonate and sodium hydrogencarbonate; metals such as sodium; metal hydride such as sodium hydride; metal alkoxides such as sodium methoxide and potassium t-butoxide; organometallic compounds such as butyl lithium and ethyl magnesium bromide; and metal amides such as lithium diisopropyl amide, and may be used alone or two or more of them may be mixed for use. The use amount of the base is preferably 0.2 to 10 mole, and particularly preferably 0.5 to 2.0 mole per mole of the corresponding carboxylic acid. When the use amount is 0.2 mole or more, a carboxylate salt compound can be efficiently prepared, and it is advantageous in terms of a cost. When the use amount is 10 mole or less, side reactions can be decreased to increase the yield.

A solvent used in the reaction shown by step iii) is selected from hydrocarbons such as toluene, xylene, hexane, and heptane; chlorinated solvents such as methylene chloride, chloroform, and dichloroethane; ethers such as diethyl ether, tetrahydrofurane, and dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide, and dimethyl sulfoxide; and water, and may be used alone or two or more of them may be mixed for use. In the reaction, a phase-transfer catalyst such as tetrabutylammonium hydrogen sulfate may be added as a catalyst. The addition amount of the phase transfer catalyst is preferably 0.0001 to 1.0 mole, and particularly preferably 0.001 to 0.5 mole per mole of alcohol compound as a raw material. When the addition amount is 0.0001 mole or more, addition effects can be assuredly obtained. When the addition amount is 1.0 mole or less, the reaction is advantageous in terms of a cost without excessively increasing a material cost.

Step iv) is a selective hydrolysis reaction of a bis-ester compound (N) or (P), in which only an ester on the side adjacent to a trifluoromethyl group having a higher acidity is selectively hydrolyzed to form a fluorine-containing monomer (1a-4) or (1b-4).

The reaction may readily proceed by a known process. For example, a NaOH aqueous solution can be used as a hydrolysis reagent. The use amount of NaOH is preferably 0.5 to 2.0 mole, and particularly preferably 1.0 to 1.1 mole based on the bis-ester compound (N) or (P). The reaction can be carried out in a solvent-free system or in a solvent. As a solvent, ethers such as 1,4-dioxane, diglyme, or triglyme, or alcohols such as 2-methyl-2-propanol can be used.

The reaction temperature of the esterification reaction may be appropriately selected according to reaction conditions. The reaction temperature is preferably in a range from −70° C. to the boiling point of the used solvent, usually 0° C. to the boiling point of the used solvent to decrease side reactions and obtain a high yield, and particularly preferably a low temperature enough to ensure a practically acceptable reaction rate. A time of the reaction is preferably determined by monitoring a progress of the reaction by thin-layer chromatography, gas chromatography, or the like to obtain a higher yield, and is usually about 30 minutes to about 40 hours. The corresponding target compound can be obtained from the reaction mixture by ordinary aqueous work-up. If necessary, the compound can be purified by ordinary techniques such as distillation, recrystallization, and chromatography.

The polymer of the present invention includes repeating units derived from the polymerizable ester compound represented by the general formula (1a) or (1b).

The repeating units derived from the polymerizable ester compounds of the formulae (1a) and (1b) specifically include the following general formulae (2a) and (2b),

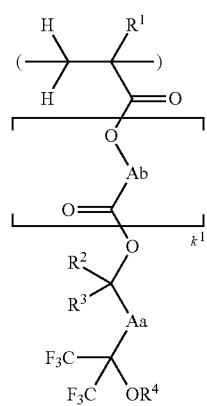

(2a)

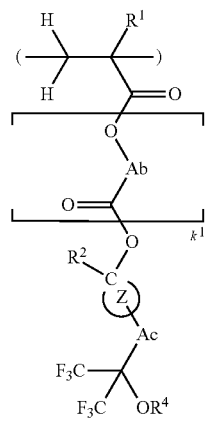

(2b)

wherein $R^1$ represents a hydrogen atom, a fluorine atom, a methyl group, or a trifluoromethyl group; $R^2$ and $R^3$ represent a linear, a branched, or a cyclic monovalent hydrocarbon group having 1 to 15 carbon atoms, or $R^2$ and $R^3$ may combine with each other to form a non-aromatic ring having 3 to 8 carbon atoms together with the carbon atoms to which they are bonded; Z represents a divalent group forming a substituted or an unsubstituted cyclopropane, cyclobutane, cyclopentane, cyclohexane, or norbornane ring together with the carbon atom to which it is bonded; Aa represents a linear, a branched, or a cyclic divalent hydrocarbon group having 1 to 10 carbon atoms; Ab is a linear, a branched, or a cyclic divalent hydrocarbon group having 1 to 6 carbon atoms; Ac represents a direct bond or a linear, a branched, or a cyclic divalent hydrocarbon group having 1 to 10 carbon atoms; $R^4$ represents a hydrogen atom, or a linear, a branched, or a cyclic monovalent hydrocarbon group having 1 to 15 carbon atoms, and when $R^4$ is a monovalent hydrocarbon group, —CH$_2$— may be substituted with —O— or —(=O)—; and $k^1$ is 0 or 1.

In addition to the repeating units of the compounds of the general formulae (2a) and/or (2b), the polymer of the present invention preferably includes at least one kind selected from repeating units represented by the following general formulae (3a) to (3d),

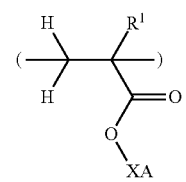

(3a)

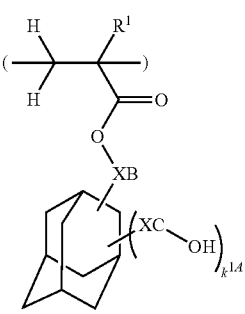

(3b)

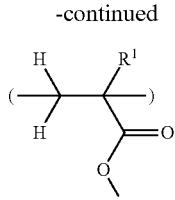

(3c)

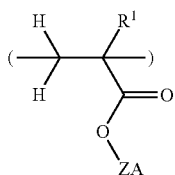

(3d)

wherein $R^1$ is as defined above; XA represents an acid labile group; each of XB and XC independently represents a single bond, or a linear or a branched divalent hydrocarbon group having 1 to 4 carbon atoms; YA represents a substituent having a lactone, sultone, hydroxy, carboxyl, ester, ether, carbonyl, amide, or cyano structure; ZA represents a hydrogen atom, or a fluoroalkyl group having 1 to 15 carbon atoms, or a fluoroalcohol-containing substituent having 1 to 15 carbon atoms; and $k^{1A}$ represents an integer of 1 to 3.

Under the action of acid, a polymer including a repeating unit of the general formula (3a) is decomposed to generate carboxylic acid, turning to be an alkali soluble polymer. The acid labile group XA may be selected from a variety of such groups. Specific examples of the acid labile group include groups represented by the following general formulae (R1-1) to (R1-4), a tertiary alkyl group having 4 to 20 carbon atoms, and preferably 4 to 15 carbon atoms, a trialkylsilyl group in which each alkyl group has 1 to 5 carbon atoms, an oxoalkyl group having 4 to 15 carbon atoms, and an acyl group having 1 to 10 carbon atoms,

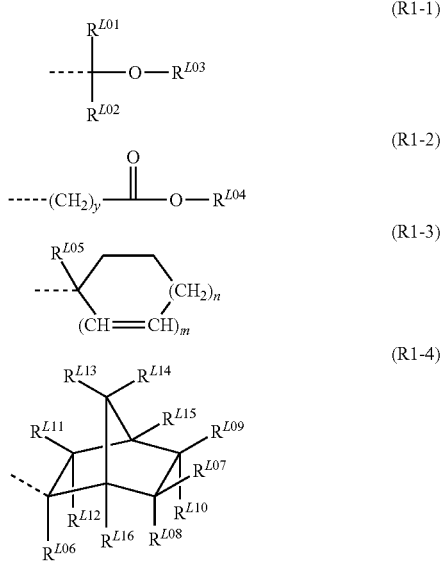

wherein $R^{L01}$ to $R^{L04}$, and y are defined above; $R^{L05}$ represents a linear, a branched, or a cyclic alkyl group having 1 to 10 carbon atoms and optionally substituted or an aryl group having 6 to 20 carbon atoms and optionally substituted; $R^{L06}$ represents a linear, a branched, or a cyclic alkyl group having 1 to 10 carbon atoms and optionally substituted or an aryl group having 6 to 20 carbon atoms and optionally substituted; each of $R^{L07}$ to $R^{L16}$ independently represents a hydrogen atom or a substituted or an unsubstituted monovalent hydrocarbon group having 1 to 15 carbon atoms; m represents 0 or 1, and n represents an integer of 0 to 3, wherein 2m+n represents 2 or 3.

In the formula (R1-3), examples of the linear, branched, or cyclic alkyl group having 1 to 10 carbon atoms and optionally substituted of $R^{L05}$ may include a linear, a branched, or a cyclic alkyl group such as a methyl group, an ethyl group, a propyl group, an isopropyl group, a n-butyl group, a sec-butyl group, a tert-butyl group, a tert-amyl group, a n-pentyl group, a n-hexyl group, a cyclopentyl group, a cyclohexyl group, and a bicyclo[2.2.1]heptyl group, in which some hydrogen atoms are replaced by a hydroxyl group, an alkoxy group, a carboxyl group, an alkoxycarbonyl group, an oxo group, an amino group, an alkylamino group, a cyano group, a mercapto group, an alkylthio group, or a sulfo group, or some methylene groups are replaced by an oxygen atom or a sulfur atom. Specific examples of the aryl group having 6 to 20 carbon atoms and optionally substituted may include a phenyl group, a methylphenyl group, a naphthyl group, an anthryl group, a phenanthryl group, and a pyrenyl group.

In the formula (R1-4), specific examples of the linear, branched, or cyclic alkyl group having 1 to 10 carbon atoms and optionally substituted or the aryl group having 6 to 20 carbon atoms and optionally substituted of $R^{L06}$ may be the same as those exemplified for $R^{L05}$.

Specific examples of the monovalent hydrocarbon group having 1 to 15 carbon atoms of $R^{L07}$ or $R^{L16}$ may include a linear, a branched, or a cyclic alkyl group such as a methyl group, an ethyl group, a propyl group, an isopropyl group, a n-butyl group, a sec-butyl group, a tert-butyl group, a tert-amyl group, a n-pentyl group, a n-hexyl group, a n-octyl group, a n-nonyl group, a n-decyl group, a cyclopentyl group, a cyclohexyl group, a cyclopentylmethyl group, a cyclopentylethyl group, a cyclopentylbutyl group, a cyclohexylmethyl group, a cyclohexylethyl group, and a cyclohexylbutyl group, in which some hydrogen atoms are replaced by a hydroxyl group, an alkoxy group, a carboxyl group, an alkoxycarbonyl group, an oxo group, an amino group, an alkylamino group, a cyano group, a mercapto group, an alkylthio group, or a sulfo group.

$R^{L07}$ to $R^{L16}$ may combine with each other to form a ring with a carbon atom to which they are bound (e.g., $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, and $R^{L13}$ and $R^{L14}$). In this case, a group involved in the forming of the ring represents a divalent hydrocarbon group such as alkylene groups having 1 to 15 carbon atoms, and specifically represents a group obtained by eliminating one hydrogen atom from groups exemplified as the monovalent hydrocarbon group. Further, $R^{L07}$ to $R^{L16}$ may form a double bond by a direct bond between groups connected to adjacent carbons (e.g., $R^{L07}$ and $R^{L09}$, $R^{L09}$ and $R^{L15}$, and $R^{L13}$ and $R^{L15}$)

Specific examples of the protecting group of the formula (R1-1) or (R1-2) are exemplified above.

Specific examples of the acid labile group of the formula (R1-3) may include a 1-methylcyclopentyl group, a 1-ethylcyclopentyl group, a 1-n-propylcyclopentyl group, a 1-isopropylcyclopentyl group, a 1-n-butylcyclopentyl group, a 1-sec-butylcyclopentyl group, a 1-cyclohexylcyclopentyl group, a 1-(4-methoxy-n-butyl)cyclopentyl group, a 1-(bicyclo[2.2.1]heptan-2-yl)cyclopentyl group, a 1-(7-oxabicyclo[2.2.1]heptan-2-yl)cyclopentyl group, a 1-methylcyclohexyl group, a 1-ethylcyclohexyl group, a 3-methyl-1-cyclopenten- 3-yl group, a 3-ethyl-1-cyclopenten-3-yl group, a 3-methyl-1-cyclohexen-3-yl group, and a 3-ethyl-1-cyclohexen-3-yl group.

As the acid labile group of the formula (R1-4), groups represented by the following formulae (L4-1) to (L4-4) are particularly preferable.

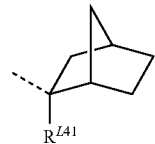
(L4-1)

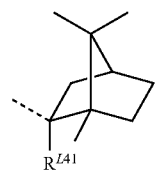
(L4-2)

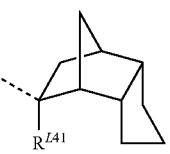
(L4-3)

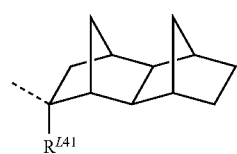
(L4-4)

wherein each $R^{L41}$ independently represents a monovalent hydrocarbon group such as a linear, a branched, or a cyclic alkyl group having 1 to 10 carbon atoms; and the broken line represents a bonding site and a bonding direction.

In the formulae (L4-1) to (L4-4), examples of the monovalent hydrocarbon group of $R^{L41}$ may include a methyl group, an ethyl group, a propyl group, an isopropyl group, a n-butyl group, a sec-butyl group, a tert-butyl group, a tert-amyl group, a n-pentyl group, a n-hexyl group, a cyclopentyl group, and a cyclohexyl group.

In the general formulae (L4-1) to (L4-4), an enantiomer or a diastereomer may be present, but each of the general formulae (L4-1) to (L4-4) typifies all the stereoisomers thereof. The stereoisomers may be used alone or in a mixture.

For example, the general formula (L4-3) typifies mixtures of one or two kinds selected from groups represented by the general formulae (L4-3-1) and (L4-3-2),

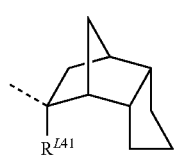
(L4-3-1)

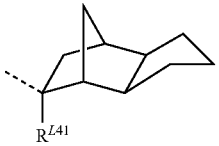
(L4-3-2)

wherein $R^{L41}$ is as defined above.

Further, the general formula (L4-4) typifies mixtures one or two or more kinds selected from groups represented by the general formulae (L4-4-1) to (L4-4-4),

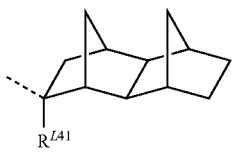
(L4-4-1)

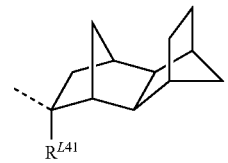
(L4-4-2)

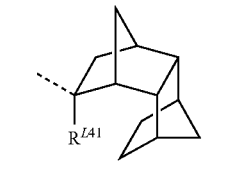
(L4-4-3)

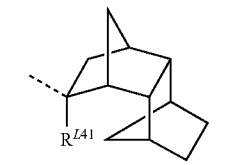
(L4-4-4)

wherein $R^{L41}$ is as defined above.

The general formulae (L4-1) to (L4-4), (L4-3-1-), (L4-3-2), and (L4-4-1) to (L4-4-4) typify enantiomers thereof and enantiomeric mixtures.

It is noted that in the formulae (L4-1) to (L4-4), (L4-3-1), (L4-3-2), and (L4-4-1) to (L4-4-4), each bond direction is on the exo side relative to the bicyclo[2.2.1]heptane ring, which ensures high reactivity for acid catalyzed deprotection reaction (see Japanese Patent Laid-Open Publication No. 2000-336121). In preparation of these monomers having a tertiary exo-alkyl group having a bicyclo[2.2.1]heptane skeleton as a substituent, there may be monomers substituted with an endo-alkyl group represented by the following general formulae (L4-1-endo) to (L4-4-endo). For good reactivity, the exo proportion is preferably 50% or more, and more preferably 80% or more.

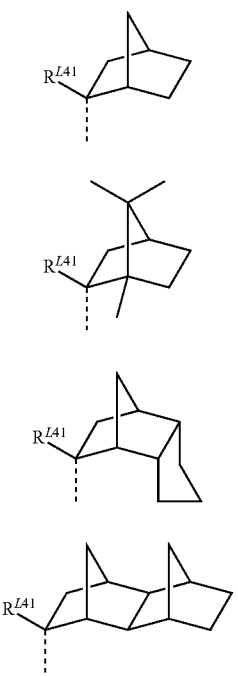

(L4-1-endo)

(L4-2-endo)

(L4-3-endo)

(L4-4-endo)

wherein $R^{L41}$ is as defined above.

Specific examples of the acid labile group of the formula (R1-4) include the following groups.

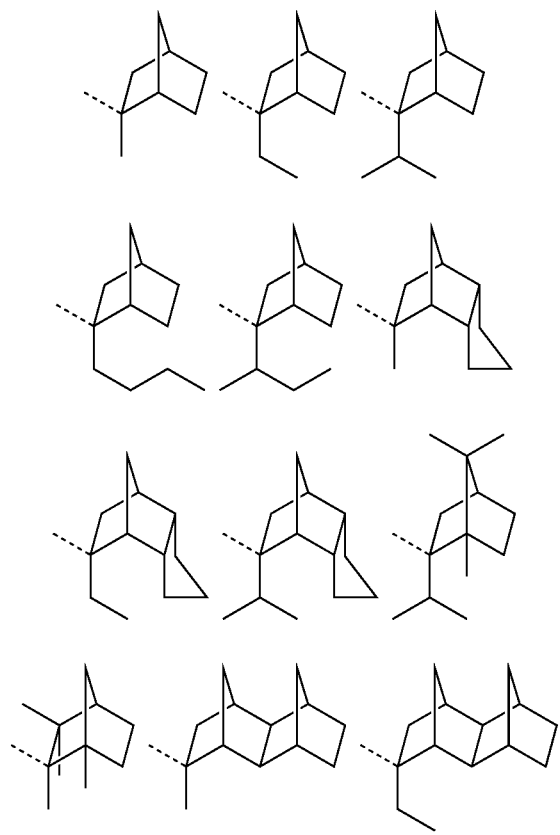

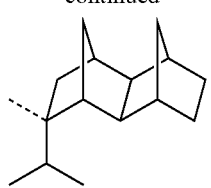

A tertiary alkyl group having 4 to 15 carbon atoms, a trialkylsilyl group in which each alkyl group has 1 to 5 carbon atoms, and an oxoalkyl group having 4 to 15 carbon atoms may be specifically the same groups as those exemplified for $R^{L104}$.

The repeating unit represented by the general formula (3a) may be specifically, but is not limited to, as follows.

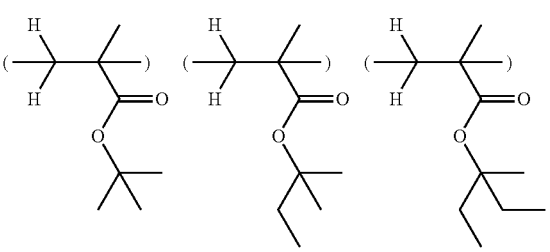

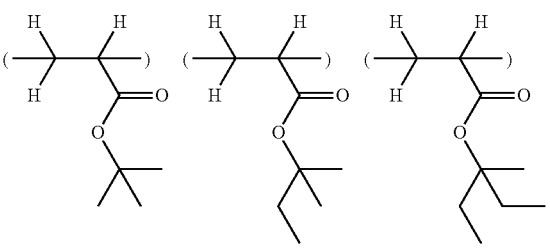

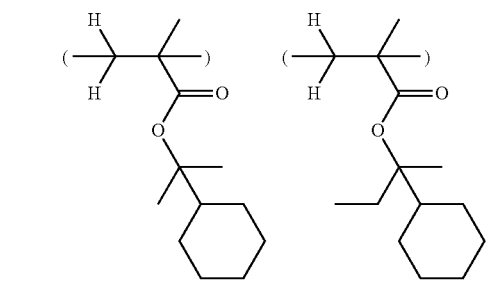

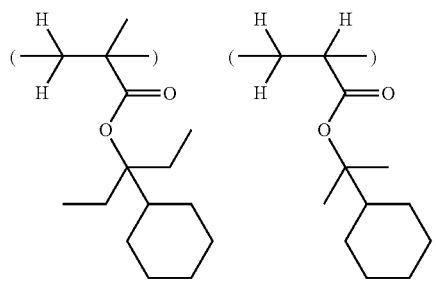

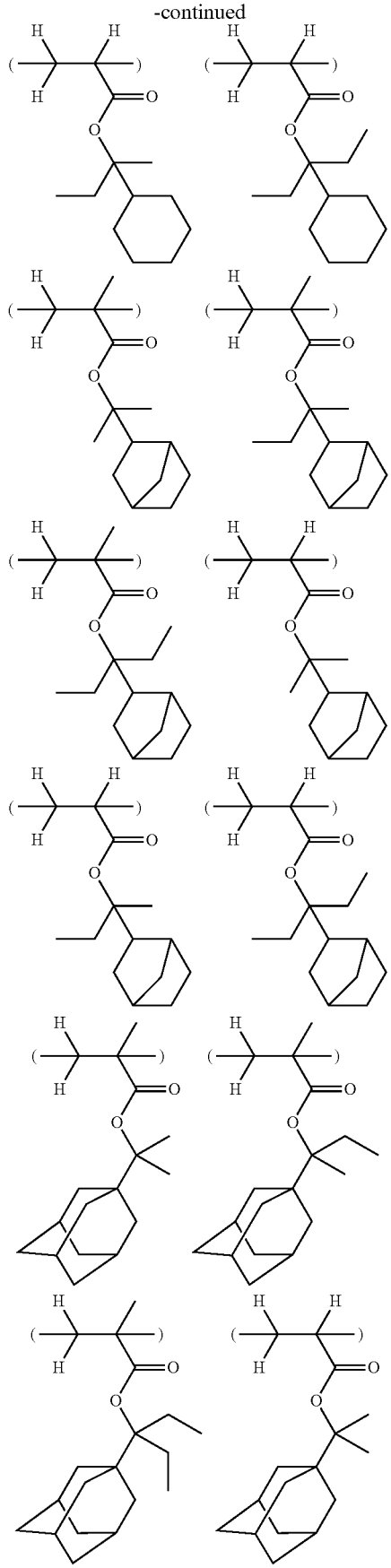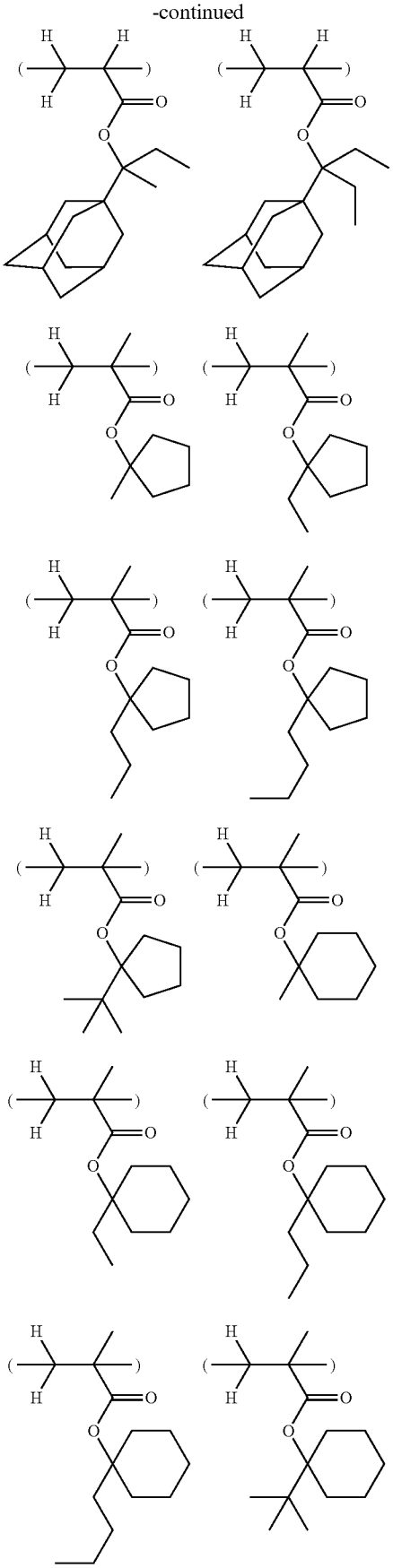

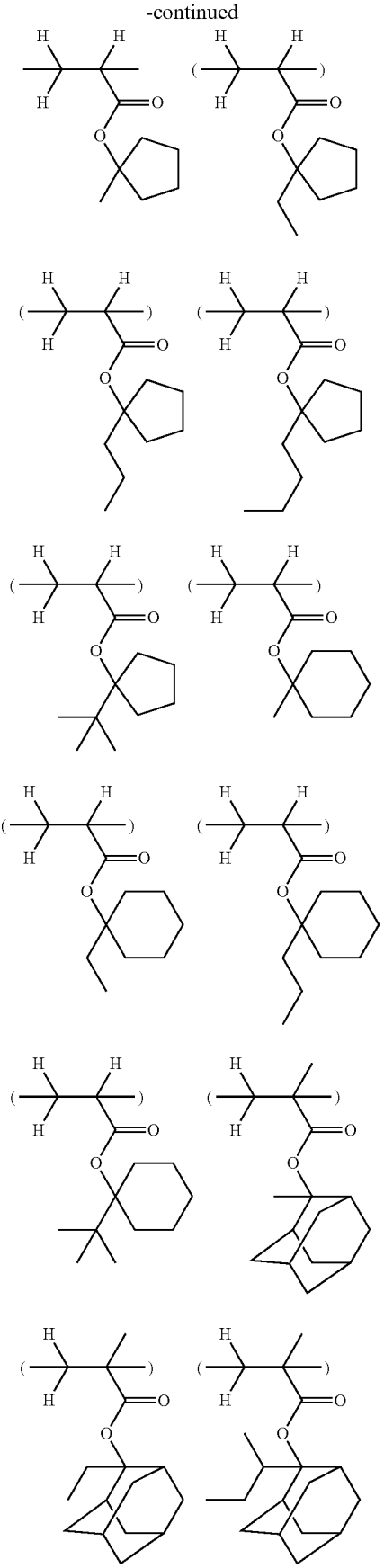
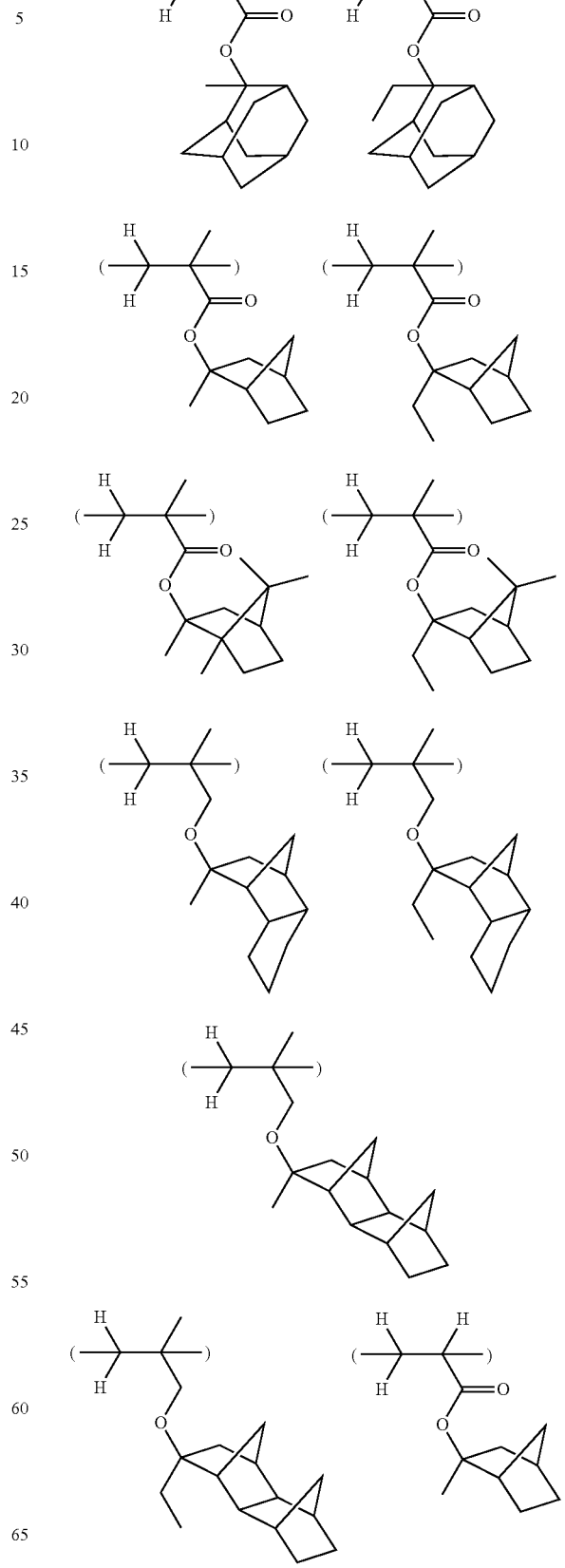

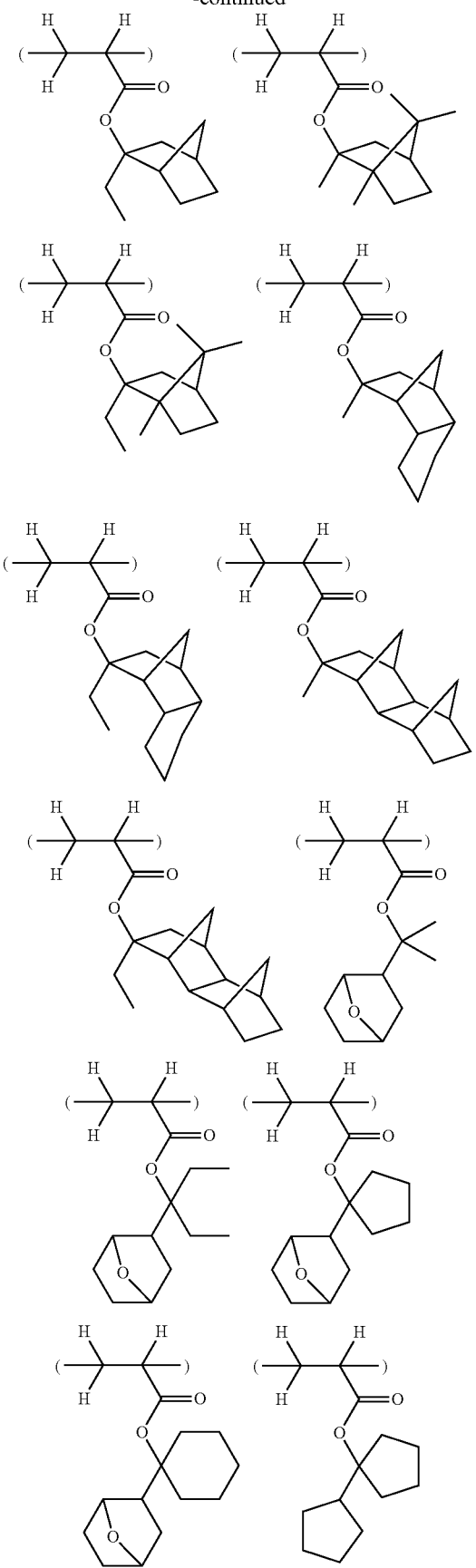
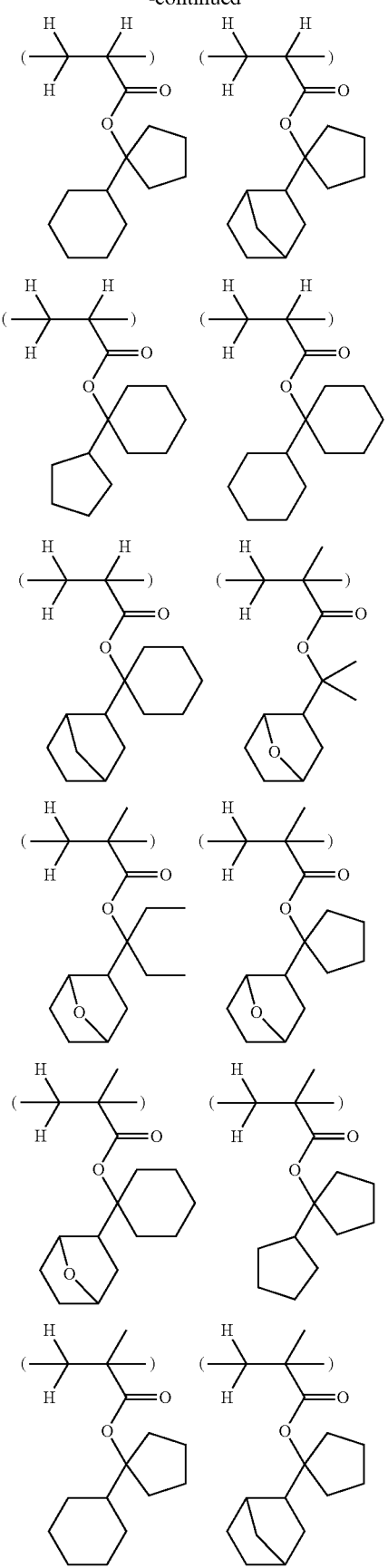

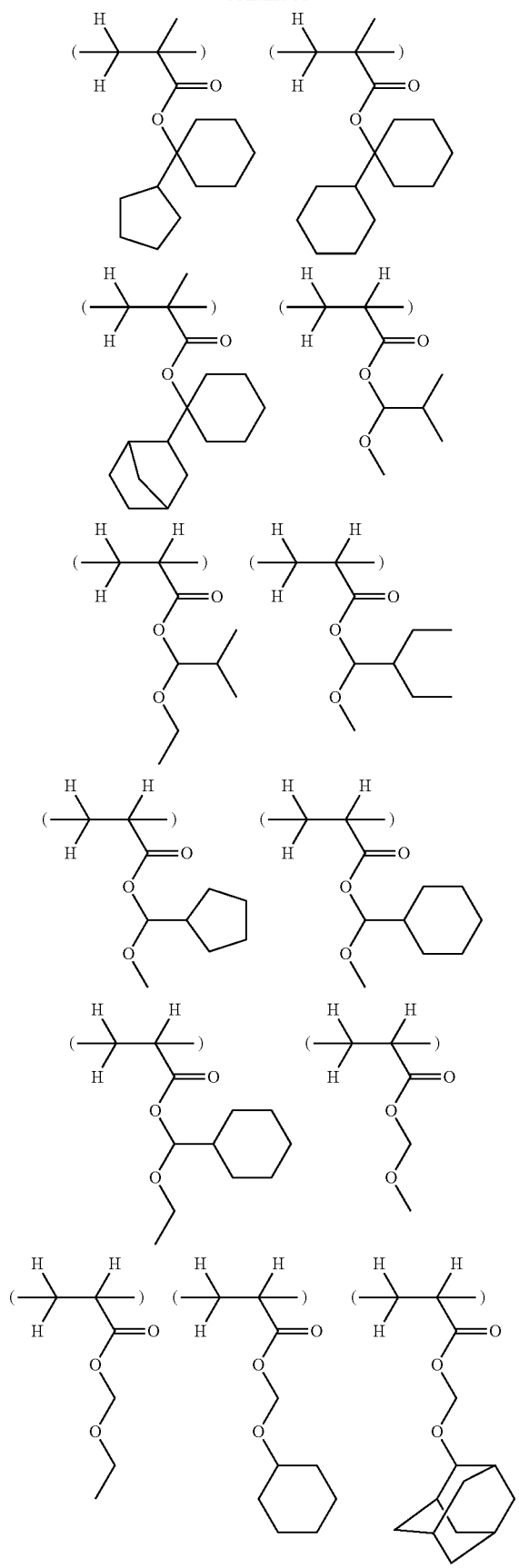
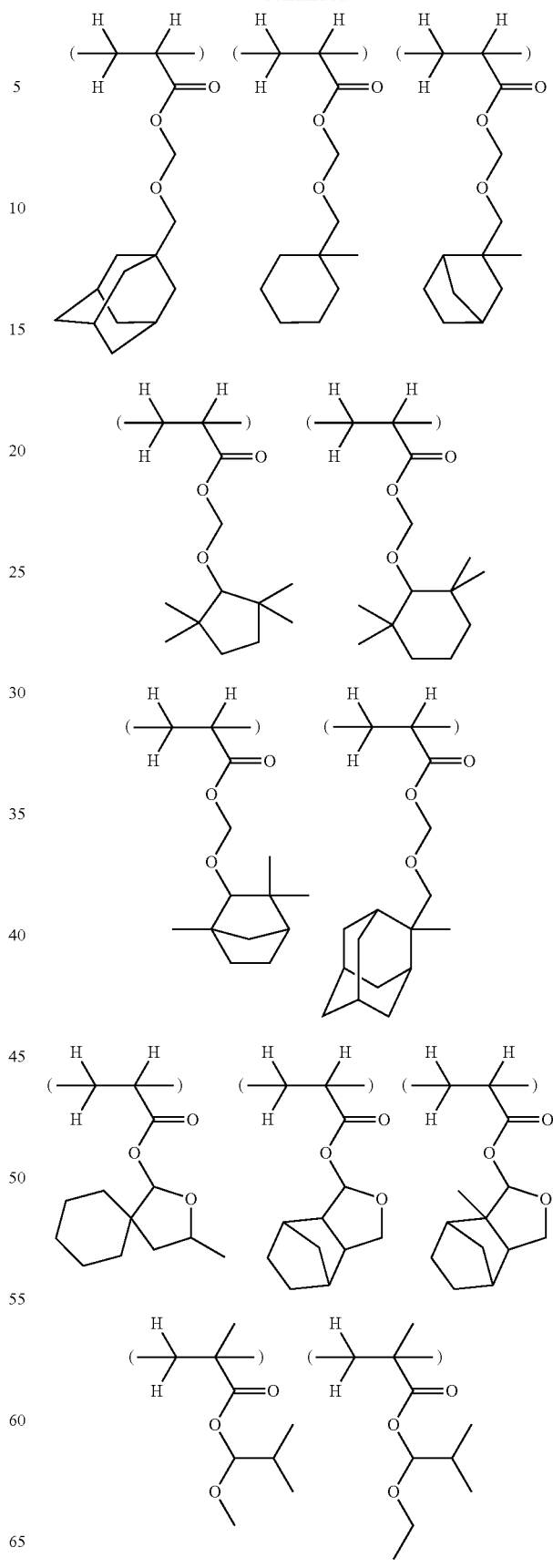

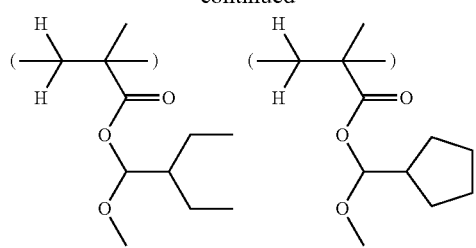
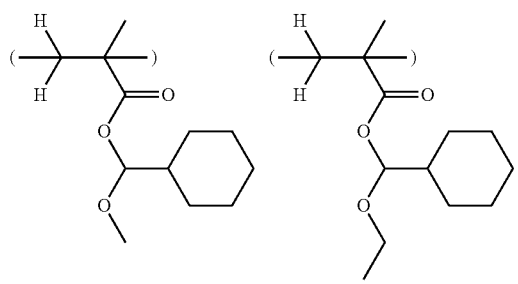
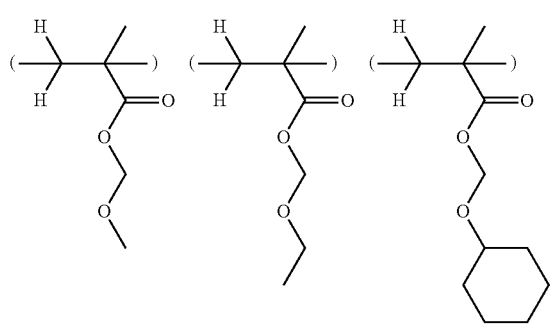
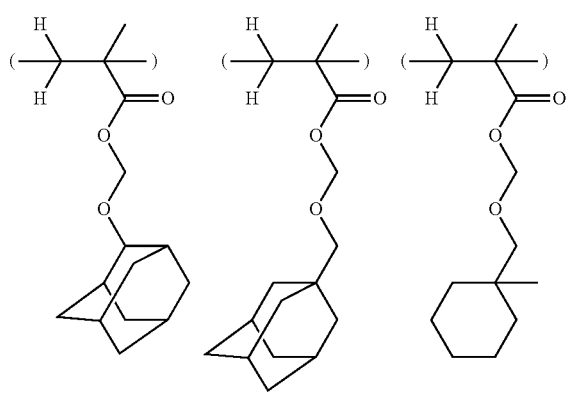
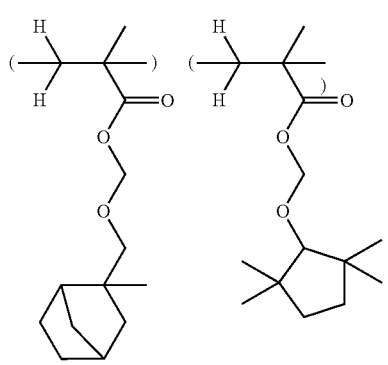
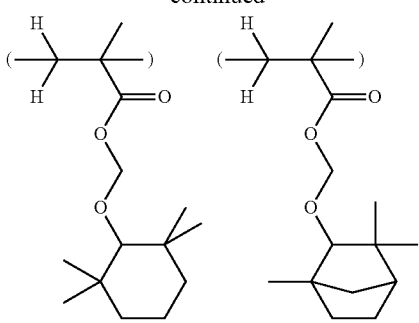
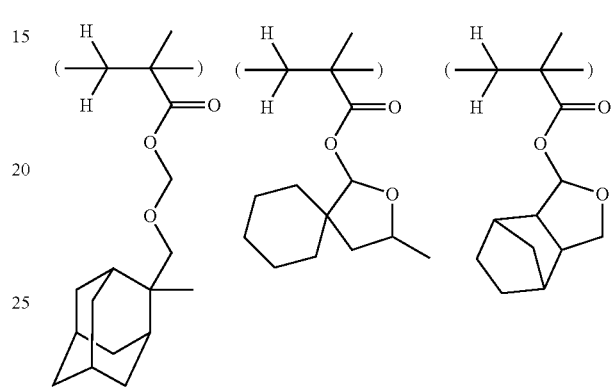
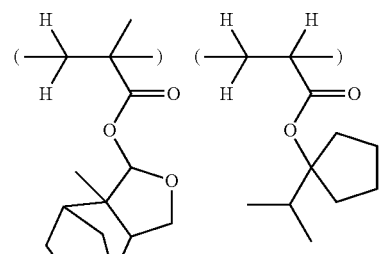
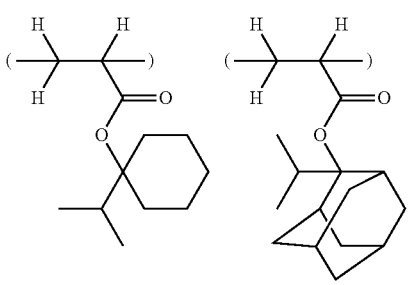
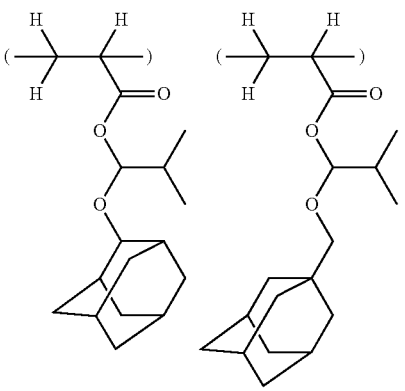

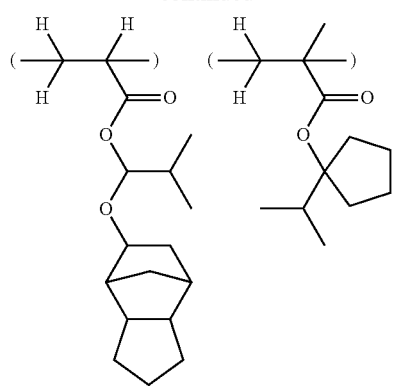
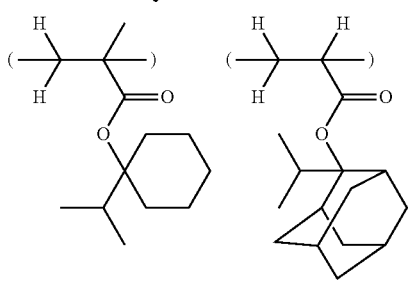
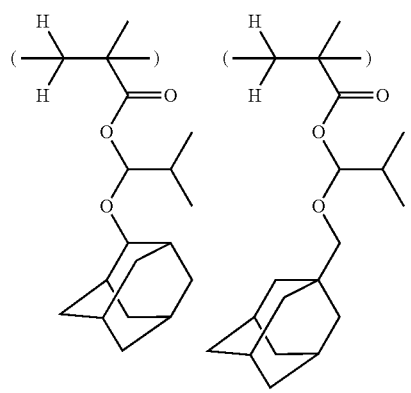
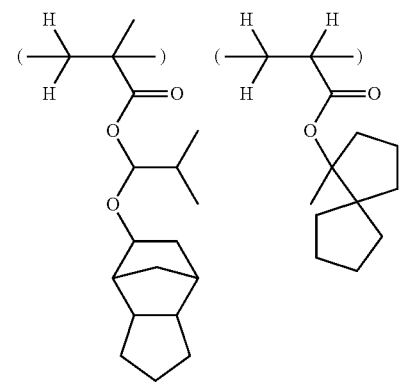
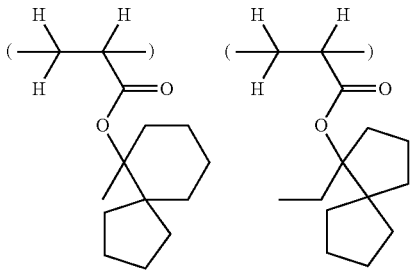
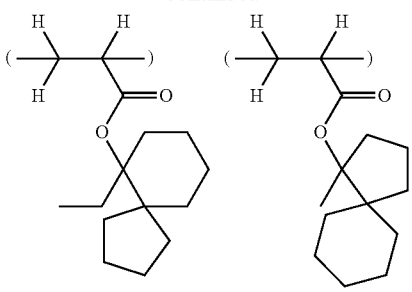
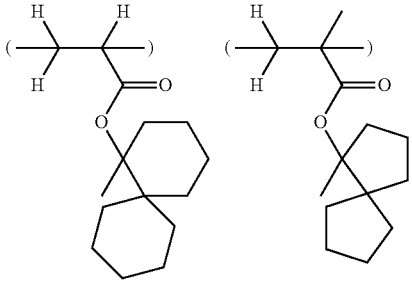
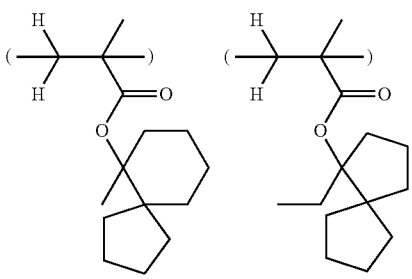
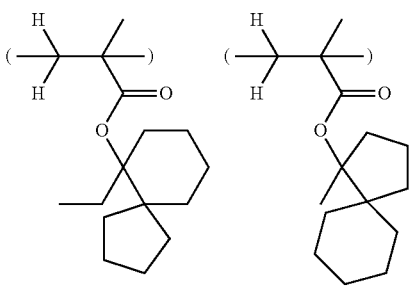
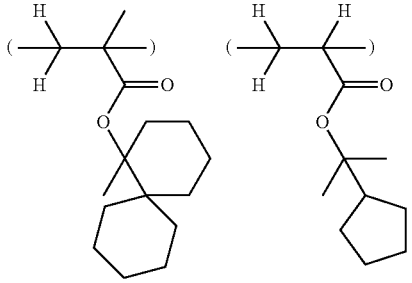

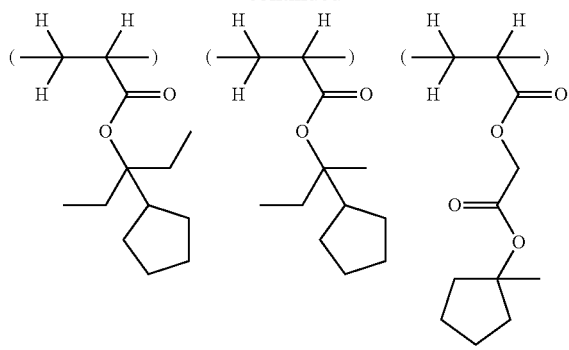
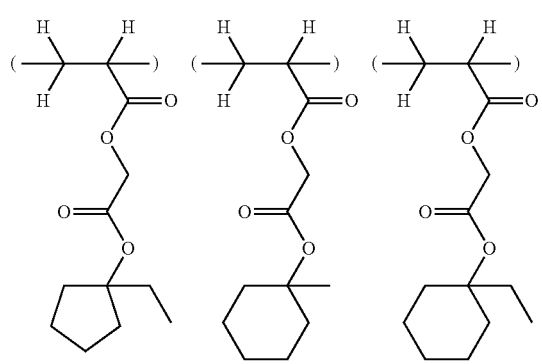
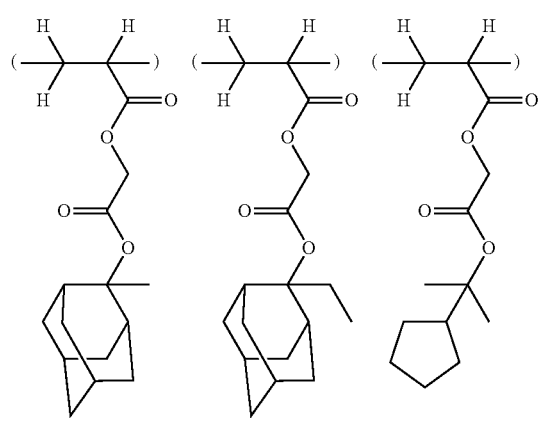
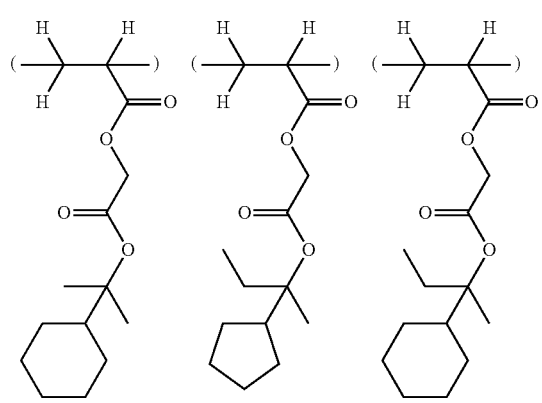
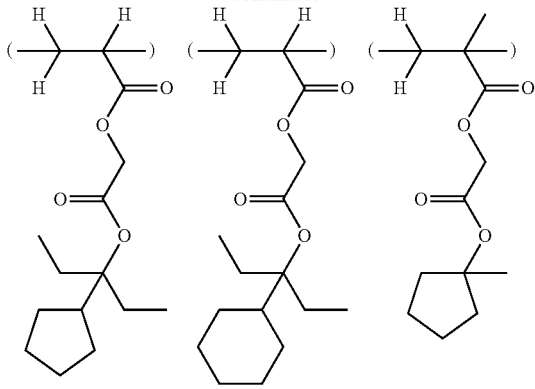
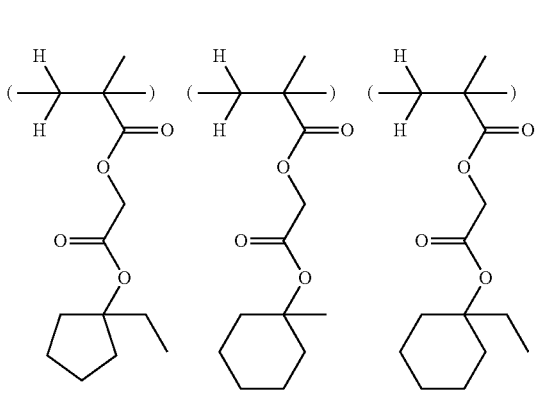
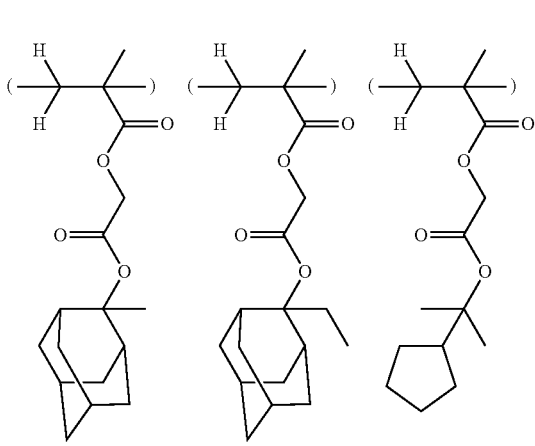
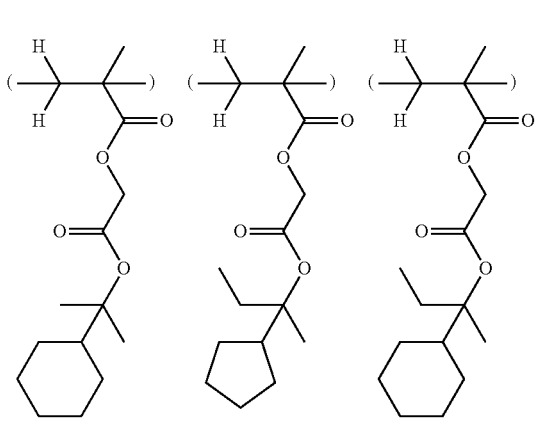

-continued
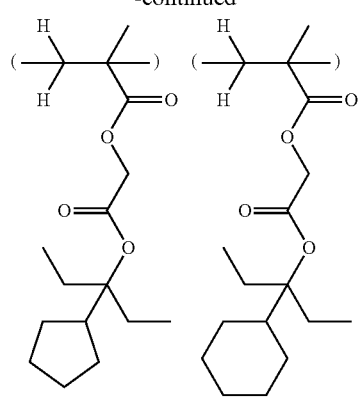
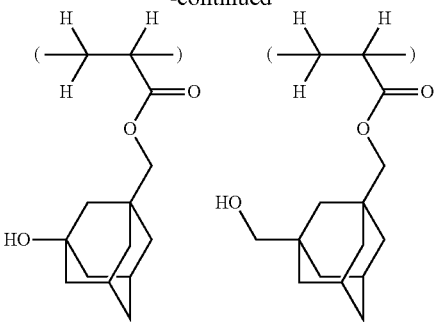
The repeating unit represented by the general formula (3b) may be specifically, but is not limited to, as follows.
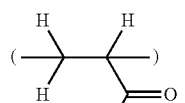
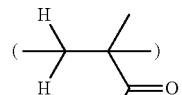
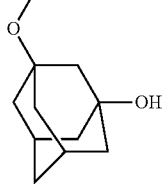
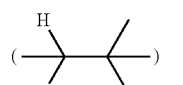
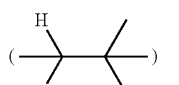
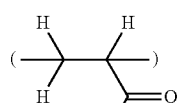
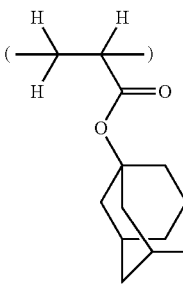
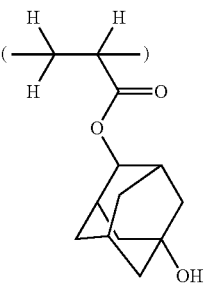
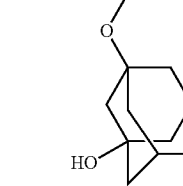
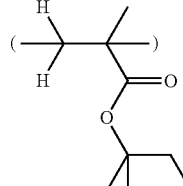
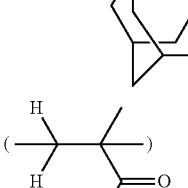
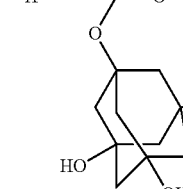
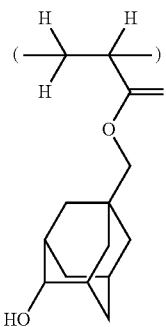

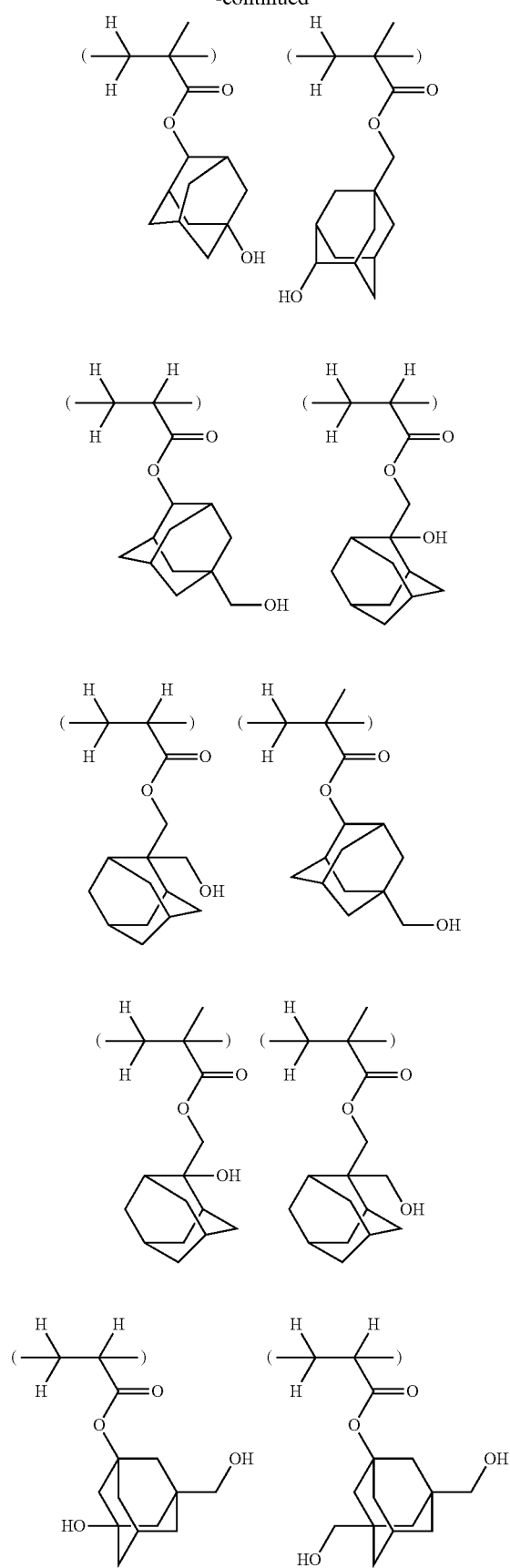
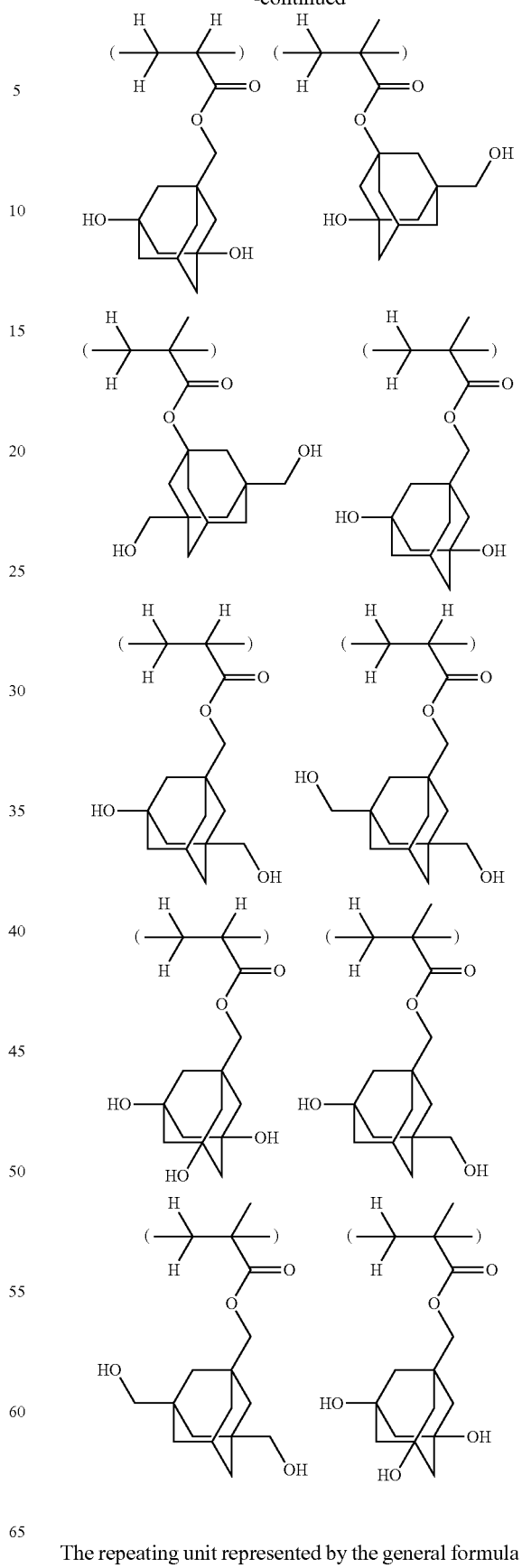
The repeating unit represented by the general formula (3c) may be specifically, but is not limited to, as follows.

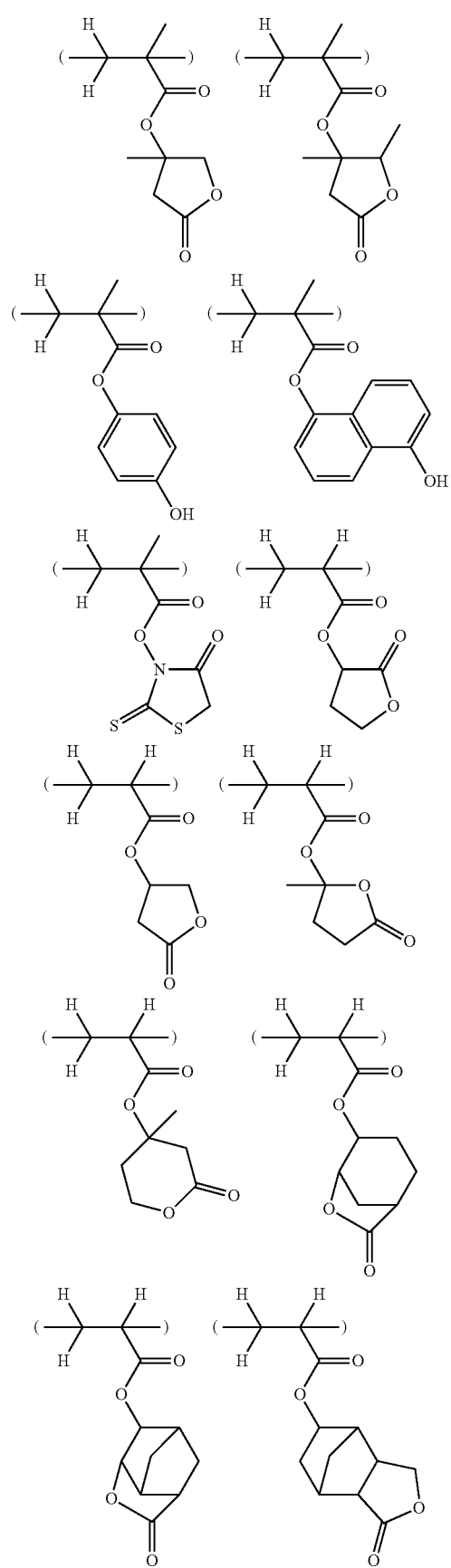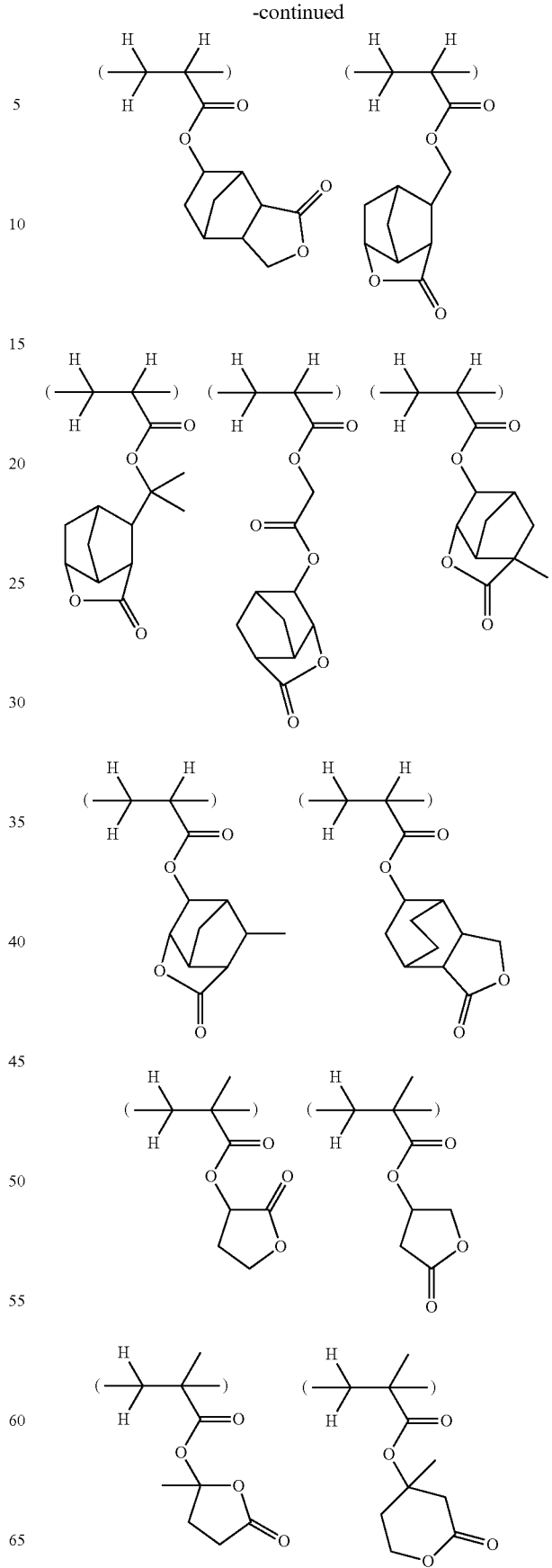

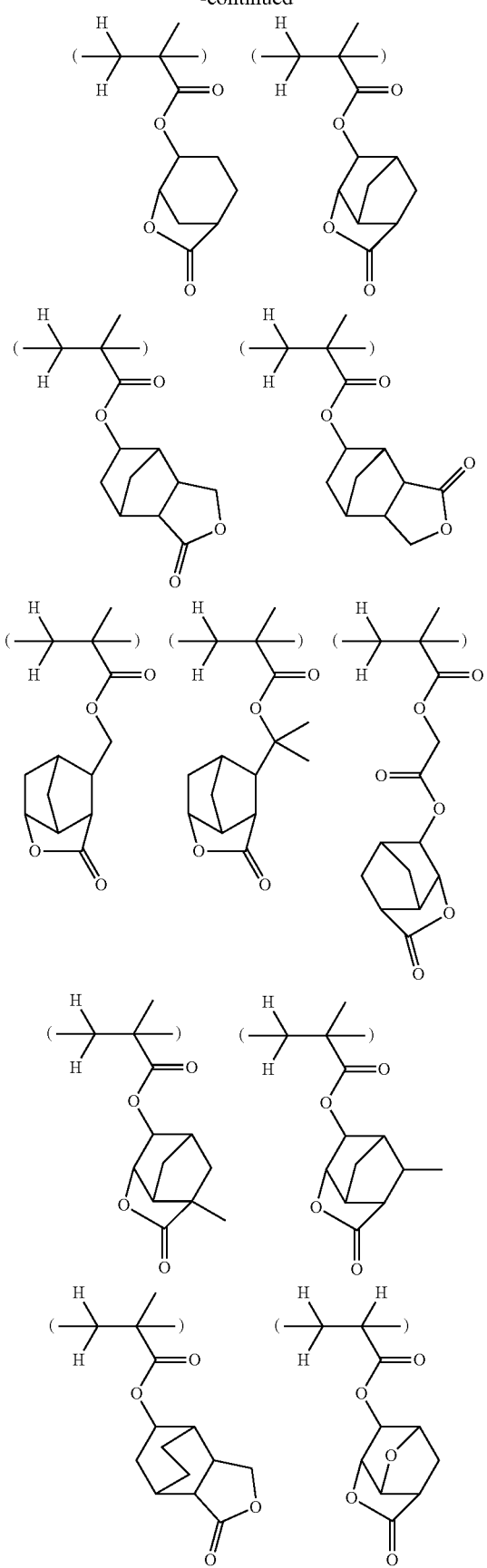
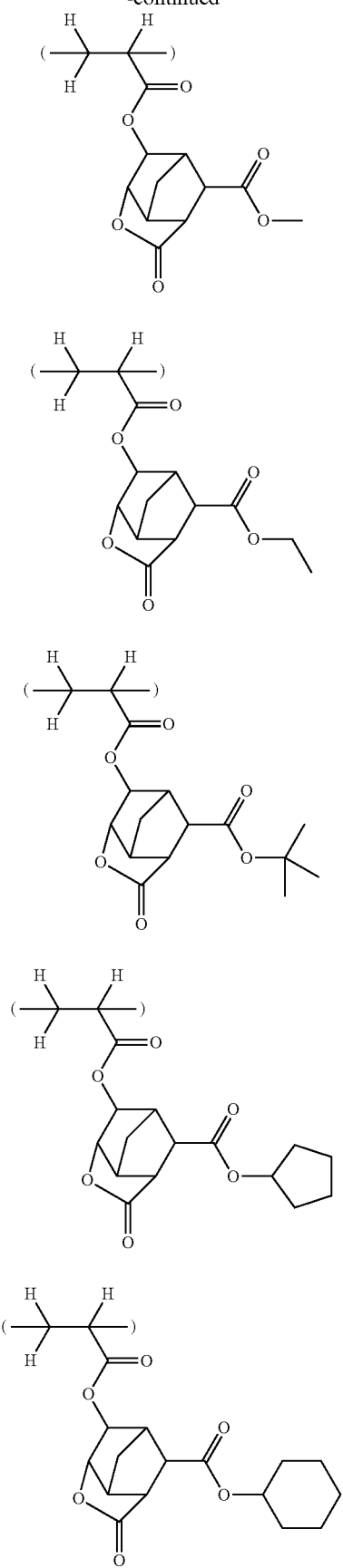

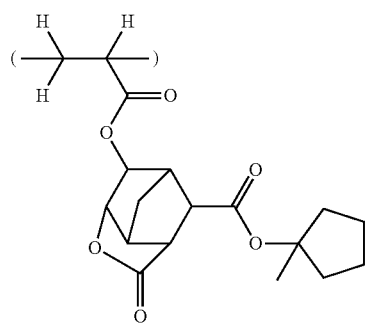
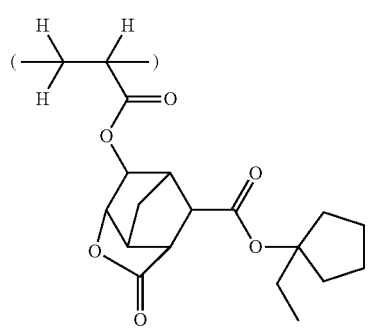
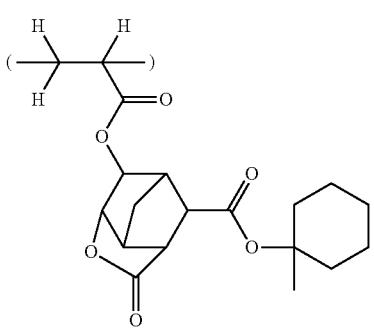
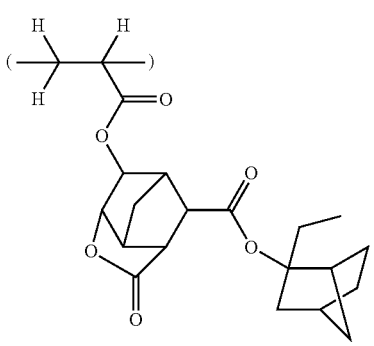
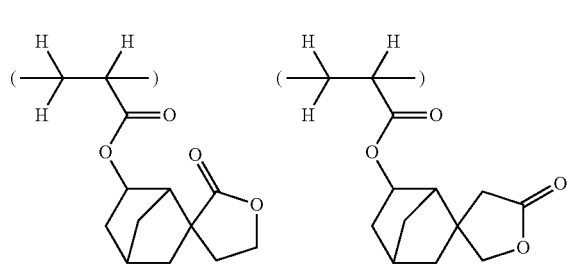
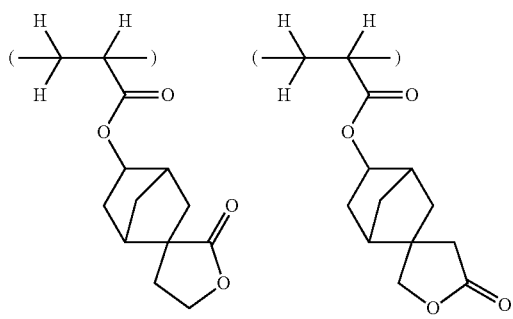
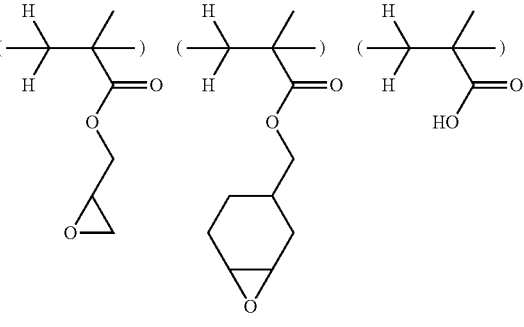
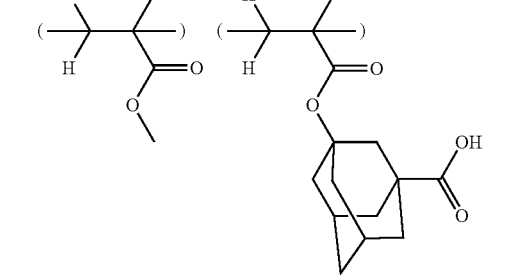
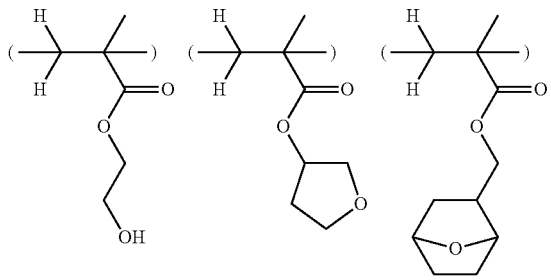
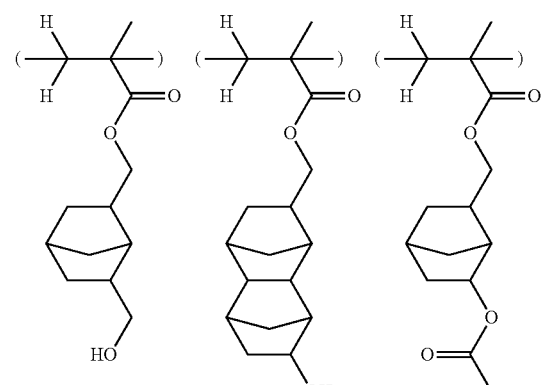

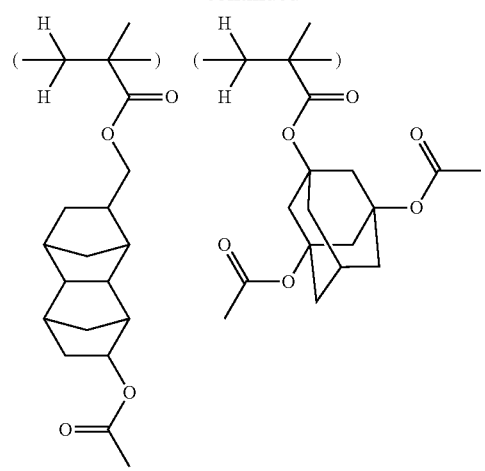
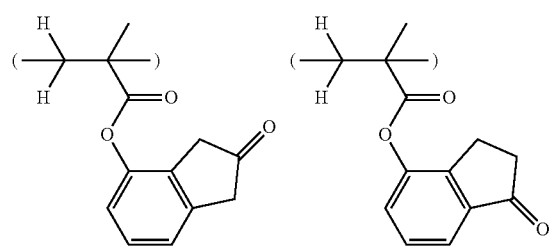
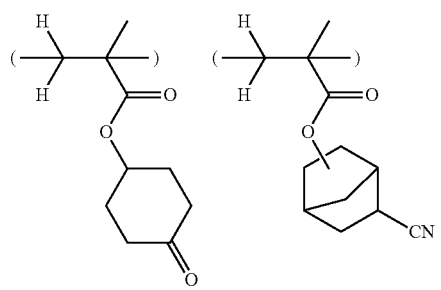
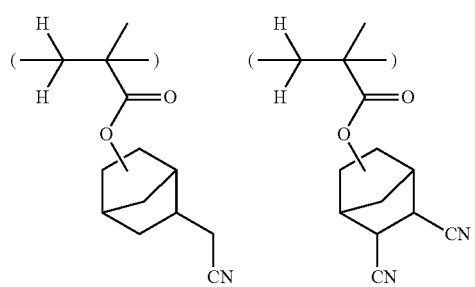
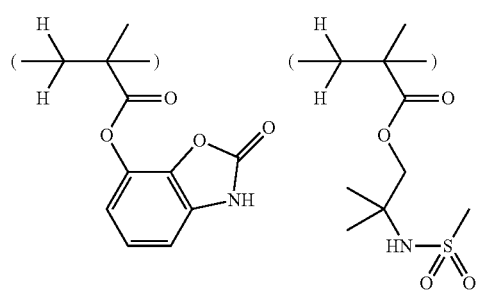
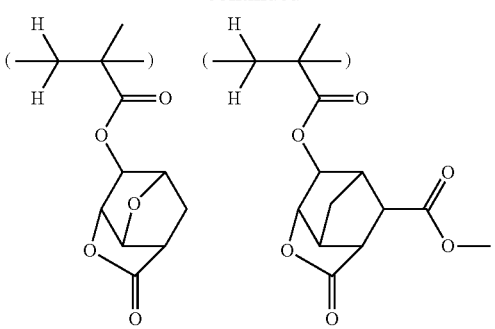
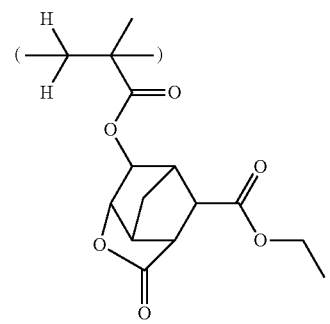
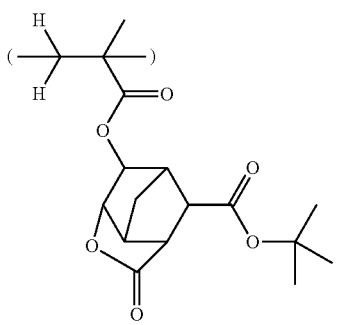
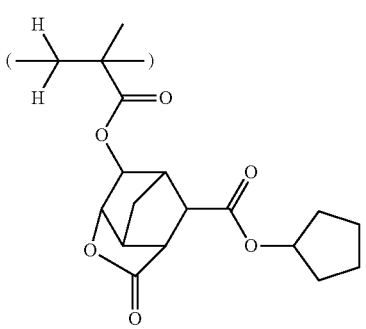
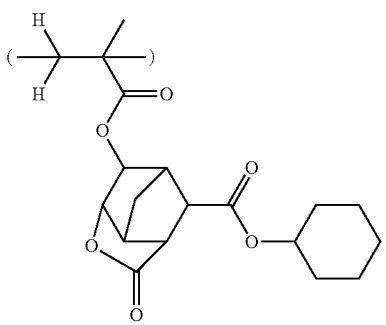

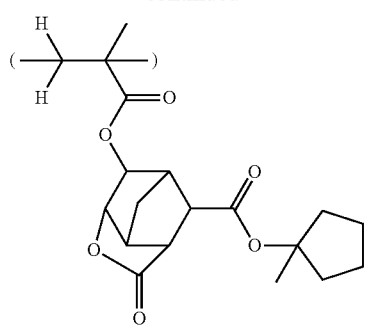
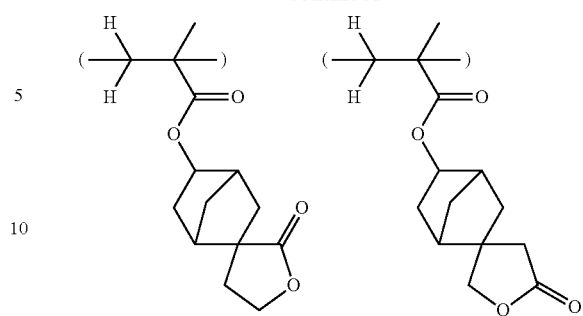
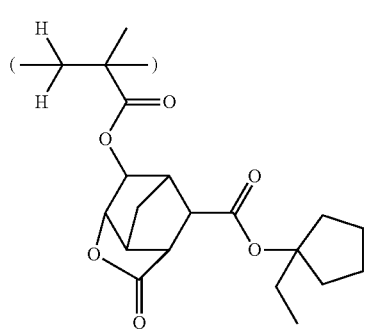
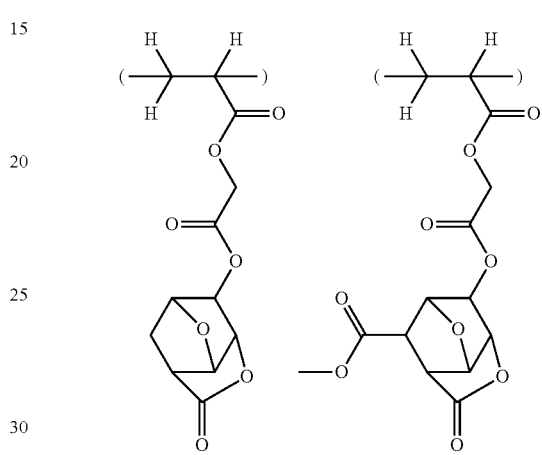
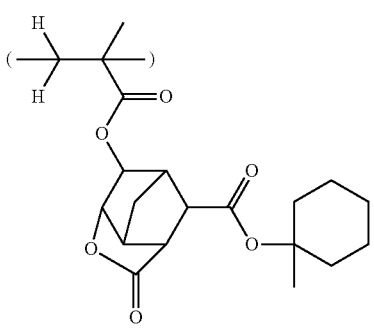
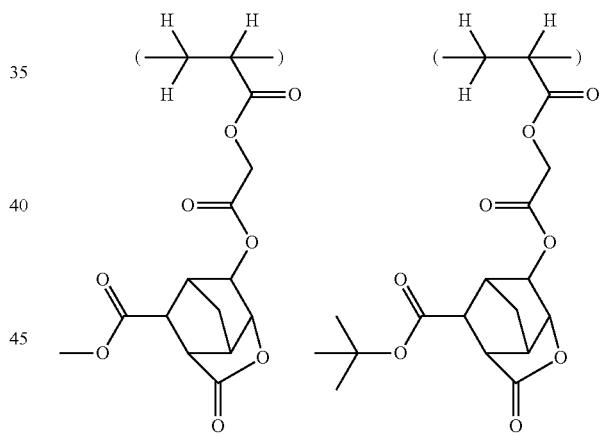
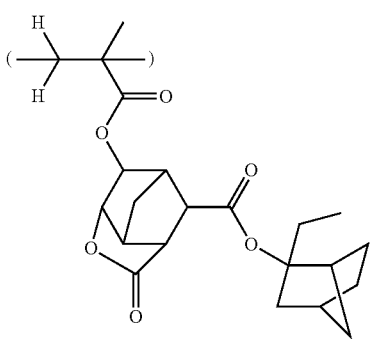
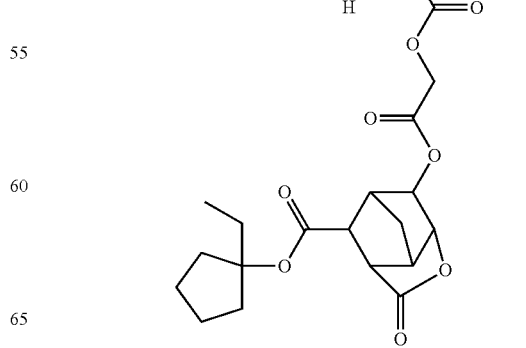
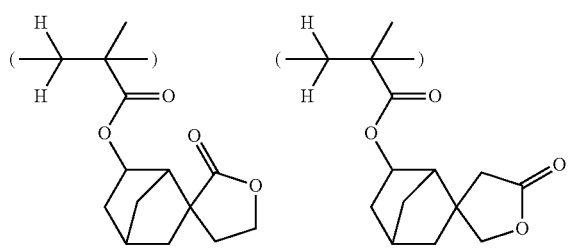

75
-continued
76
-continued
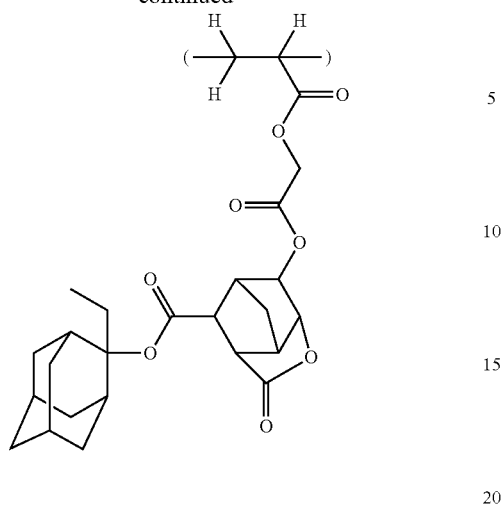
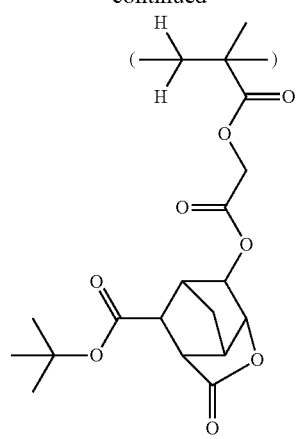
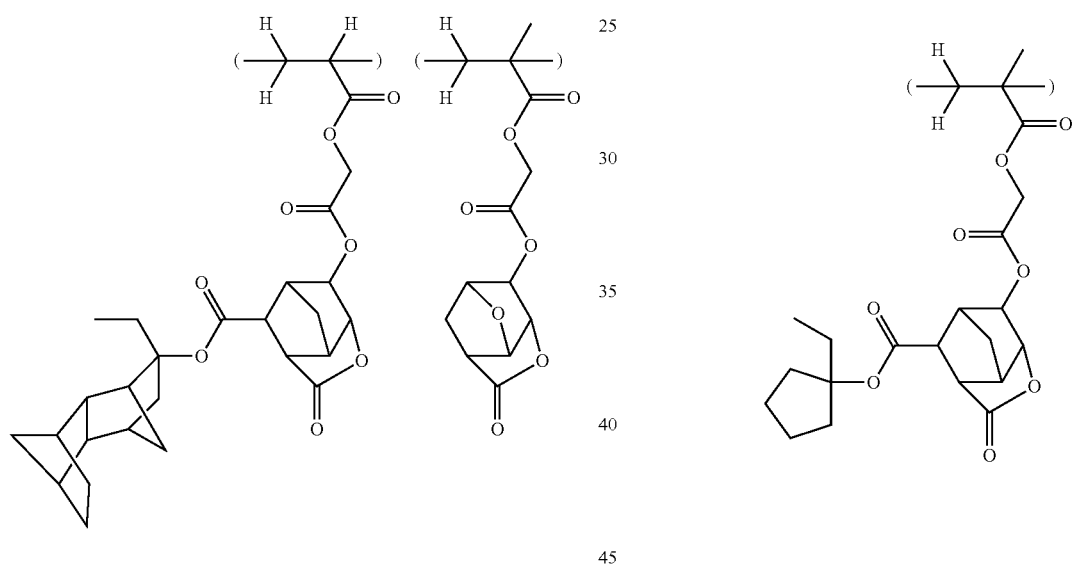
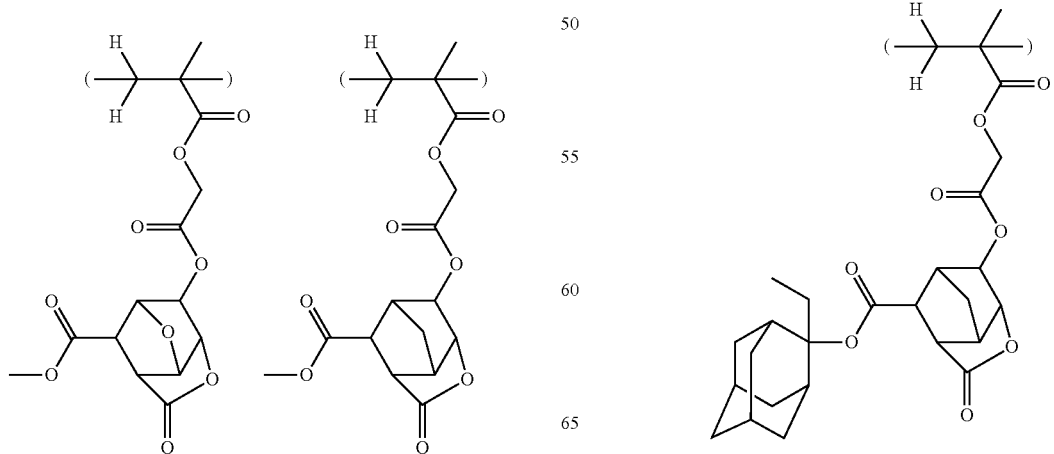

-continued
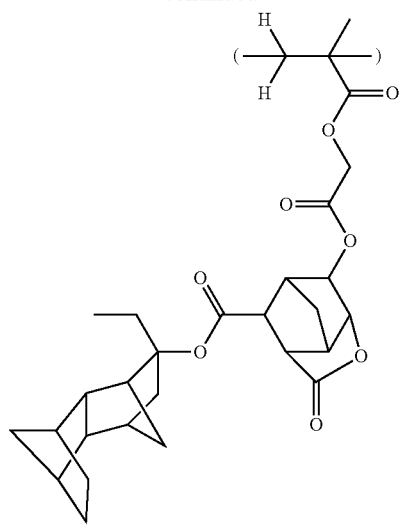
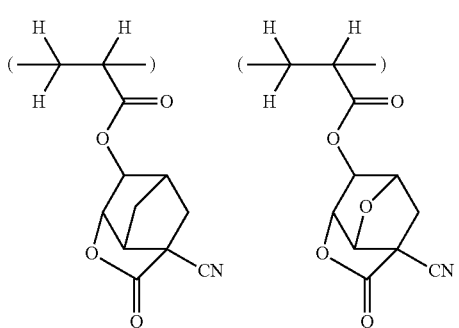
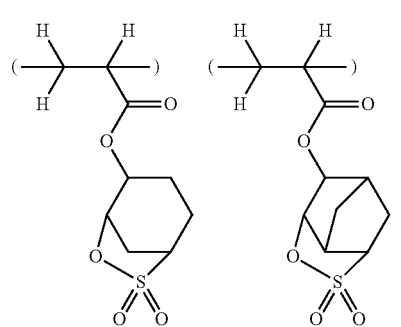
-continued
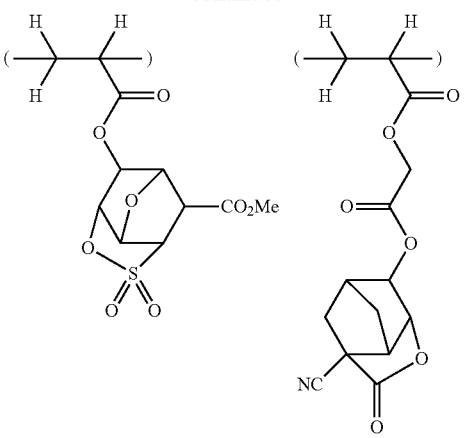
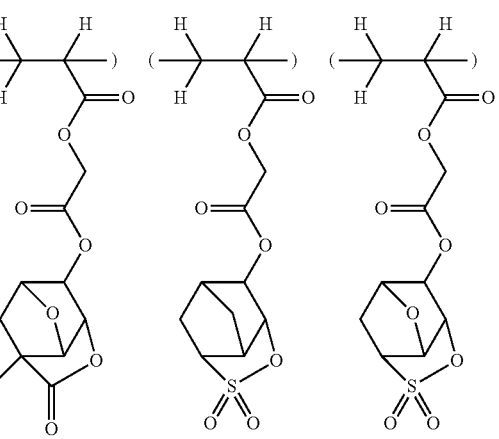
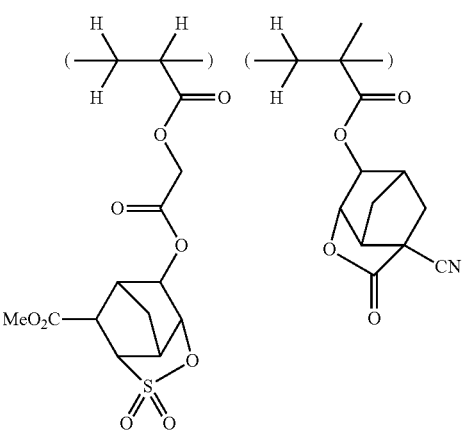

-continued
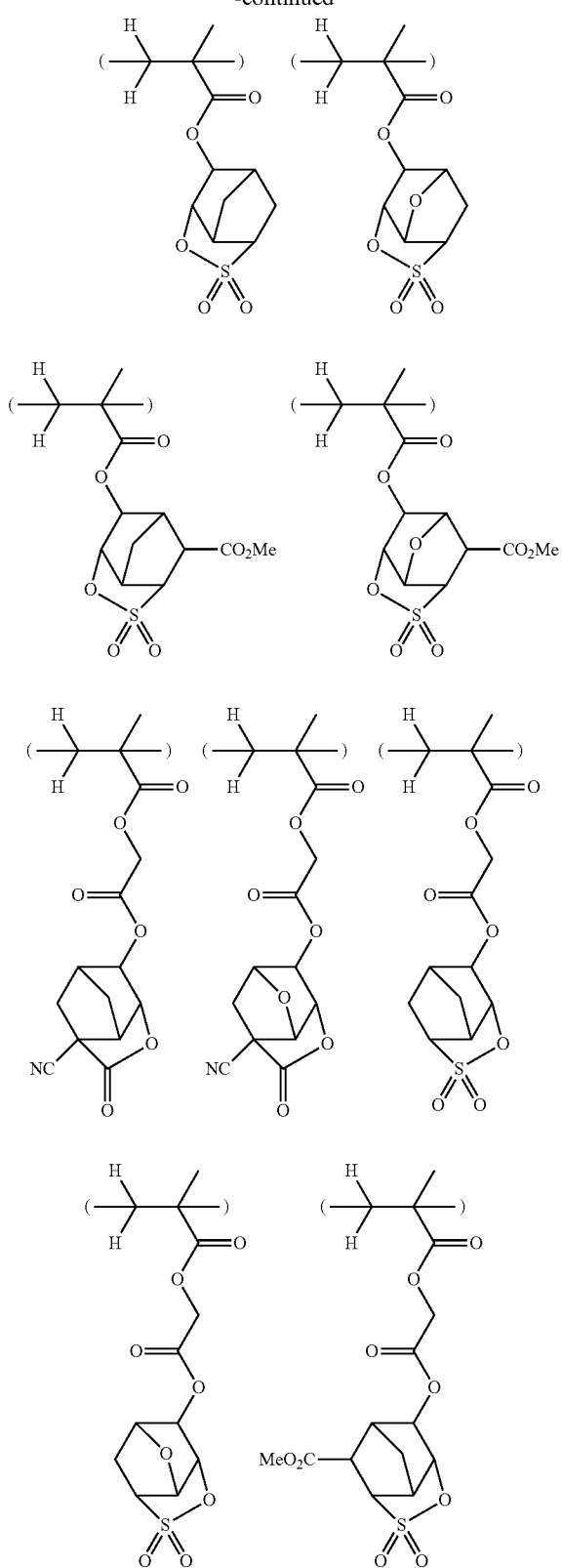
wherein Me represents a methyl group.
The repeating unit represented by the general formula (3d) may be specifically, but is not limited to, as follows.
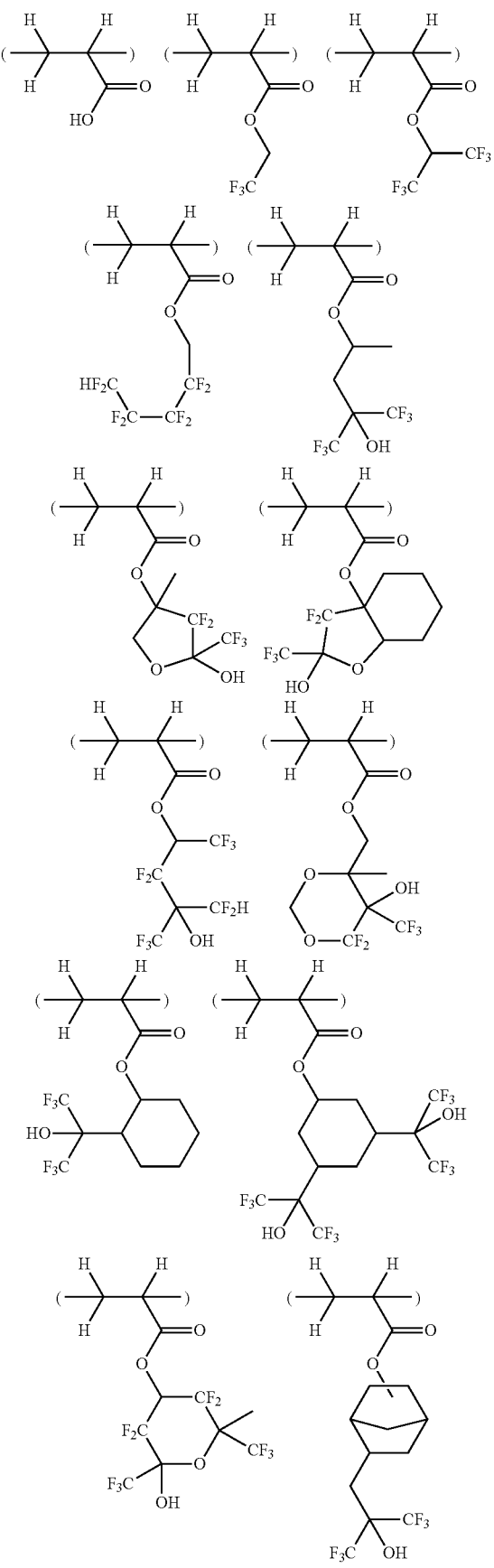

-continued
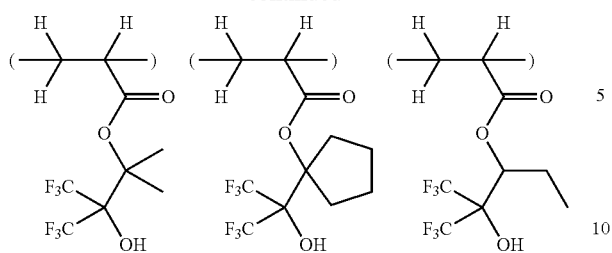
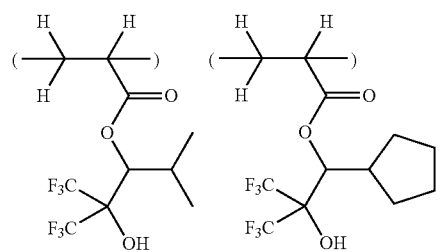
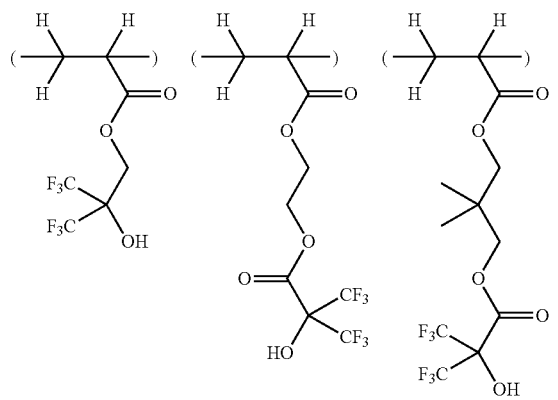
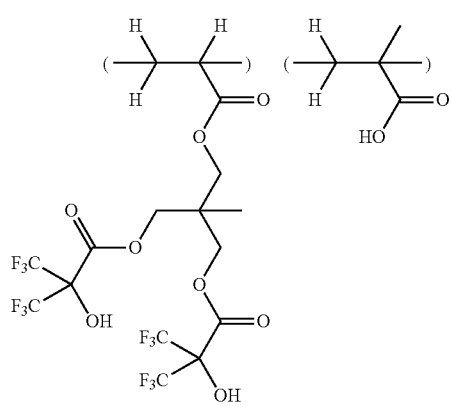
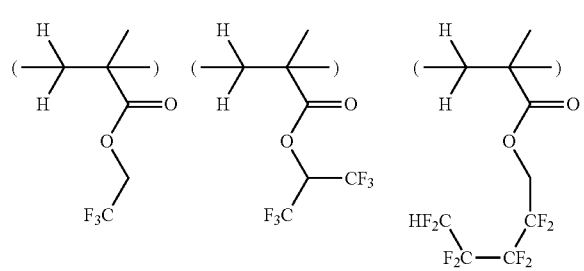
-continued
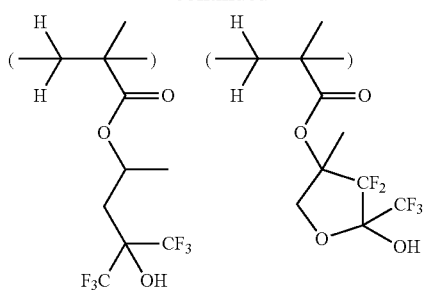
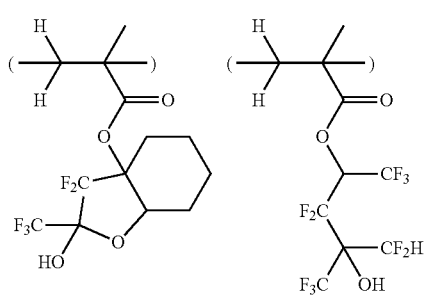
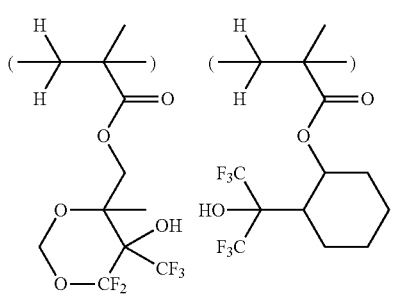
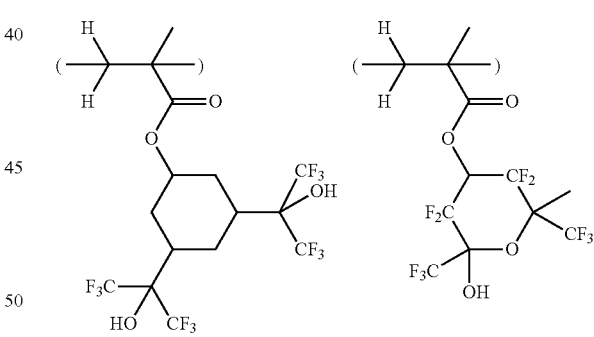
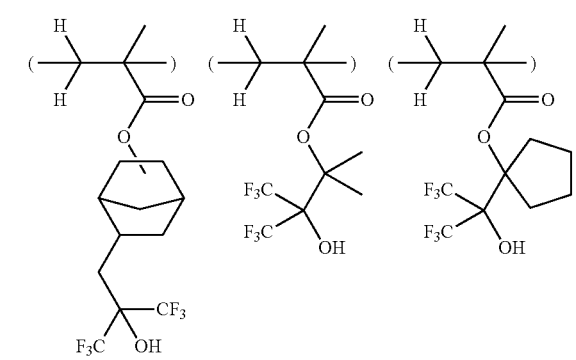

-continued

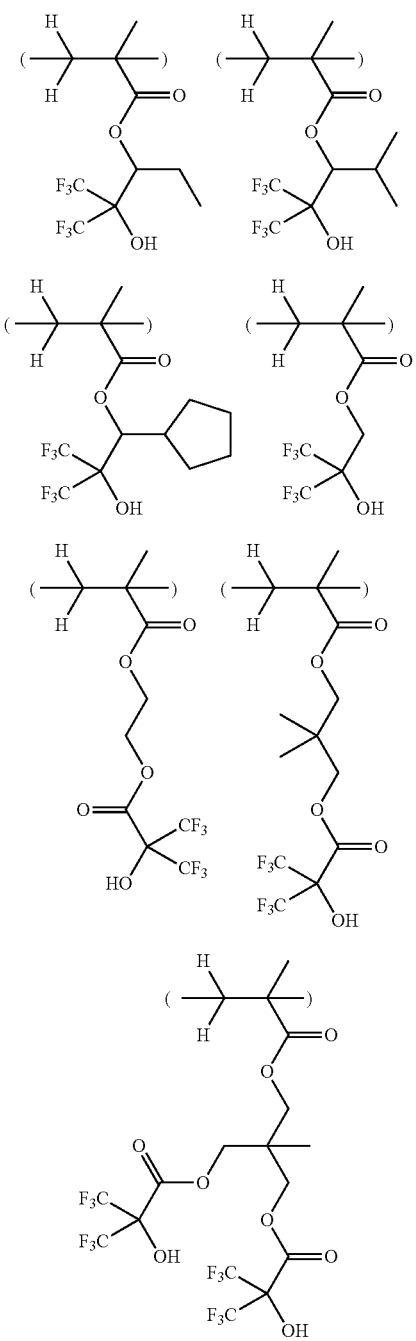

The polymer of the present invention may be copolymerized with any sulfonium salts represented by the following general formulae (d1) to (d3), (d1)

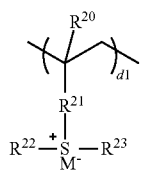

-continued (d2)

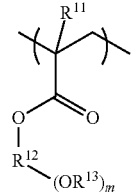

(d3)

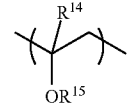

wherein $R^{20}$, $R^{24}$, and $R^{28}$ represent a hydrogen atom or a methyl group; $R^{21}$ represents a single bond, a phenylene group, —O—$R^{33}$—, or —C(=O)—Y—$R^{33}$—; Y represents an oxygen atom or NH; and $R^{33}$ represents a linear, a branched, or a cyclic alkylene group having 1 to 6 carbon atoms, an alkenylene group, or a phenylene group, optionally containing a carbonyl group (—CO—), an ester group (—COO—), an ether group (—O—), or a hydroxy group; $R^{22}$, $R^{23}$, $R^{25}$, $R^{26}$, $R^{27}$, $R^{29}$, $R^{30}$, and $R^{31}$ represent the same or different linear, branched, or cyclic alkyl groups having 1 to 12 carbon atoms, optionally containing a carbonyl group, an ester group, or an ether group, or represent an aryl group having 6 to 12 carbon atoms, an aralkyl group having 7 to 20 carbon atoms, or a thiophenyl group; $Z_0$ represents a single bond, a methylene group, an ethylene group, a phenylene group, a fluorinated phenylene group, —O—$R^{32}$—, or —C(=O)—$Z_1$—$R^{32}$—; $Z_1$ represents an oxygen atom or NH; $R^{32}$ represents a linear, a branched, or a cyclic alkylene group having 1 to 6 carbon atoms, an alkenylene group, or a phenylene group, optionally containing a carbonyl group, an ester group, an ether group, or a hydroxy group; and M⁻ represents a non-nucleophilic counter ion.

The polymer of the present invention may be copolymerized with repeating units in which the hydroxy group is substituted with an acid labile group, which are represented by the following general formulae (4a) and/or (4b), (4a)

(4b)

wherein each of $R^{11}$ and $R^{14}$ independently represents a hydrogen atom or a methyl group; $R^{12}$ represents a linear, a branched, or a cyclic aliphatic hydrocarbon group having a valence of 2 to 5 and 1 to 16 carbon atoms, optionally containing an ether group or an ester group; $R^{13}$ and $R^{15}$ represent an acid labile group; and m represents an integer of 1 to 4.

Copolymerization of repeating units obtained by substituting a hydroxyl group with an acid labile group can improve dissolution contrast in development using an organic solvent. As the acid labile groups represented by $R^{13}$ and $R^{15}$, groups represented by the general formulae (R1-1) to (R1-4) or tertiary alkyl groups having 4 to 20 carbon atoms, and preferably 4 to 15 carbon atoms may be used.

Specific examples of a monomer for obtaining a repeating unit (4a) may be as follows. In the following examples, $R^{11}$, $R^{13}$, $R^{14}$, and $R^{15}$ may be defined above.

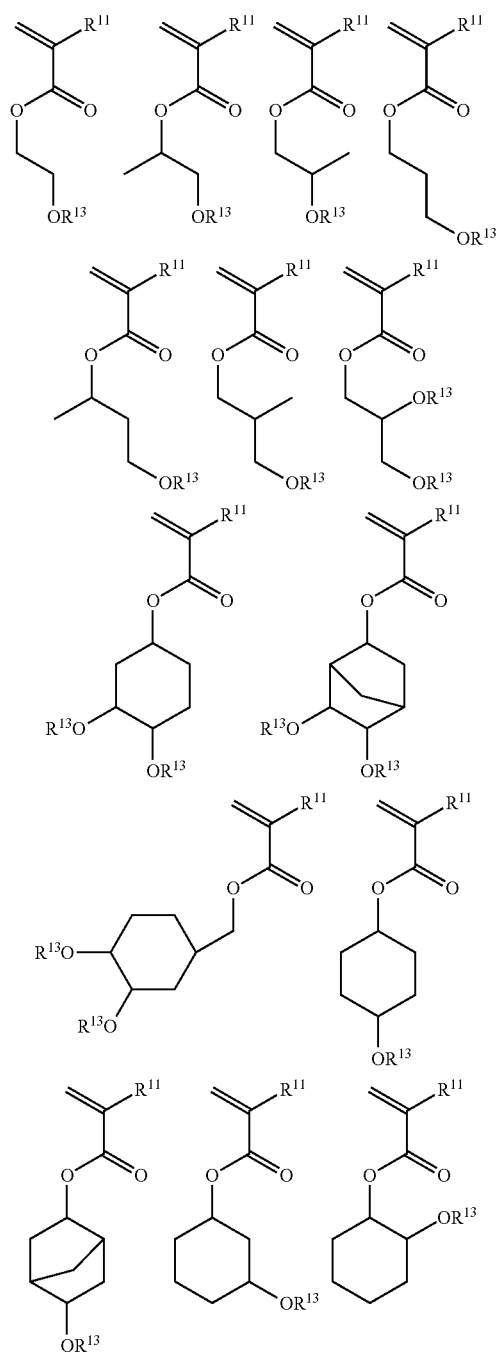

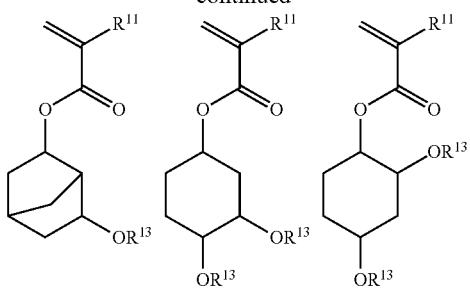

-continued

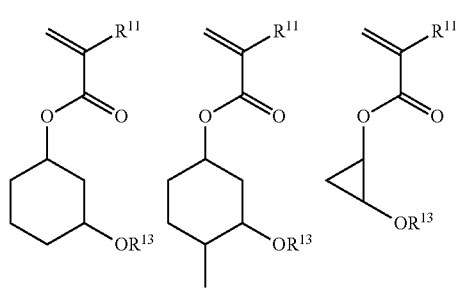

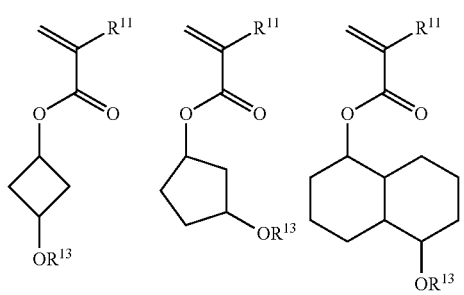

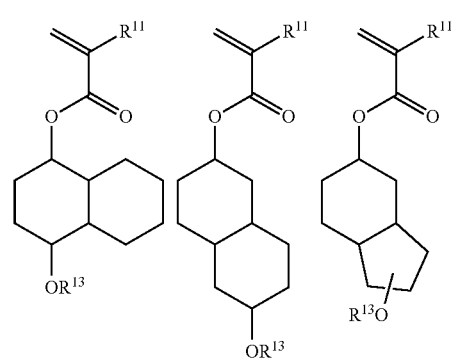

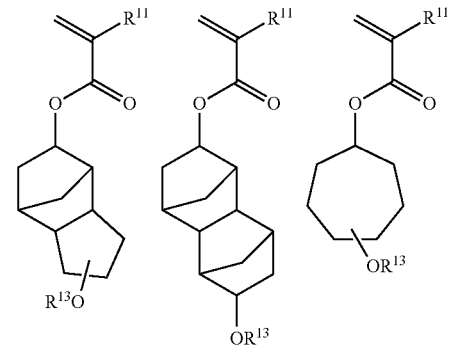

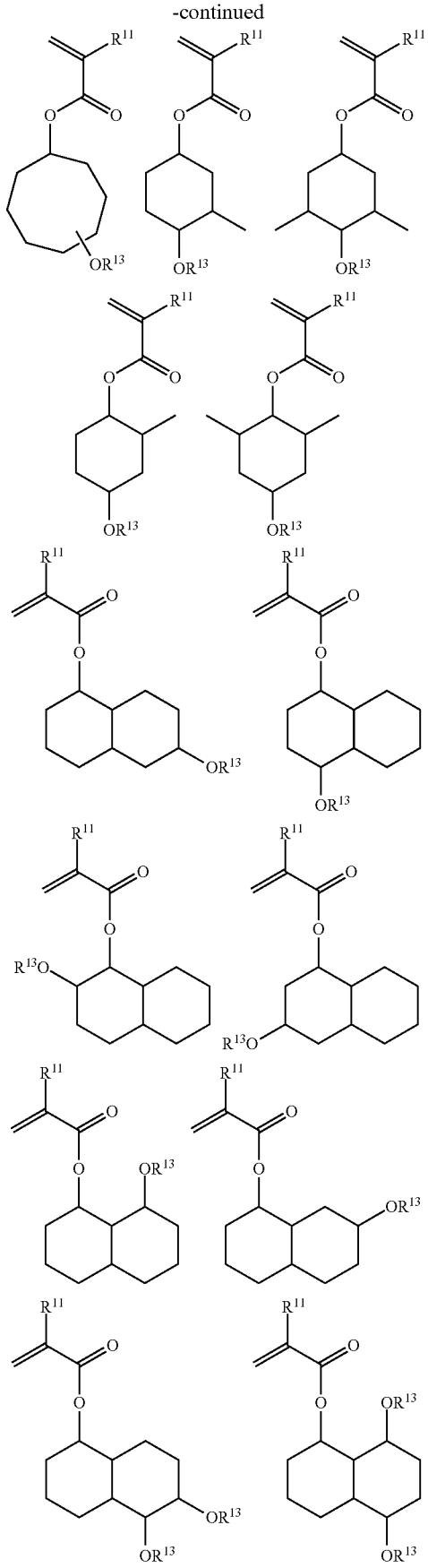
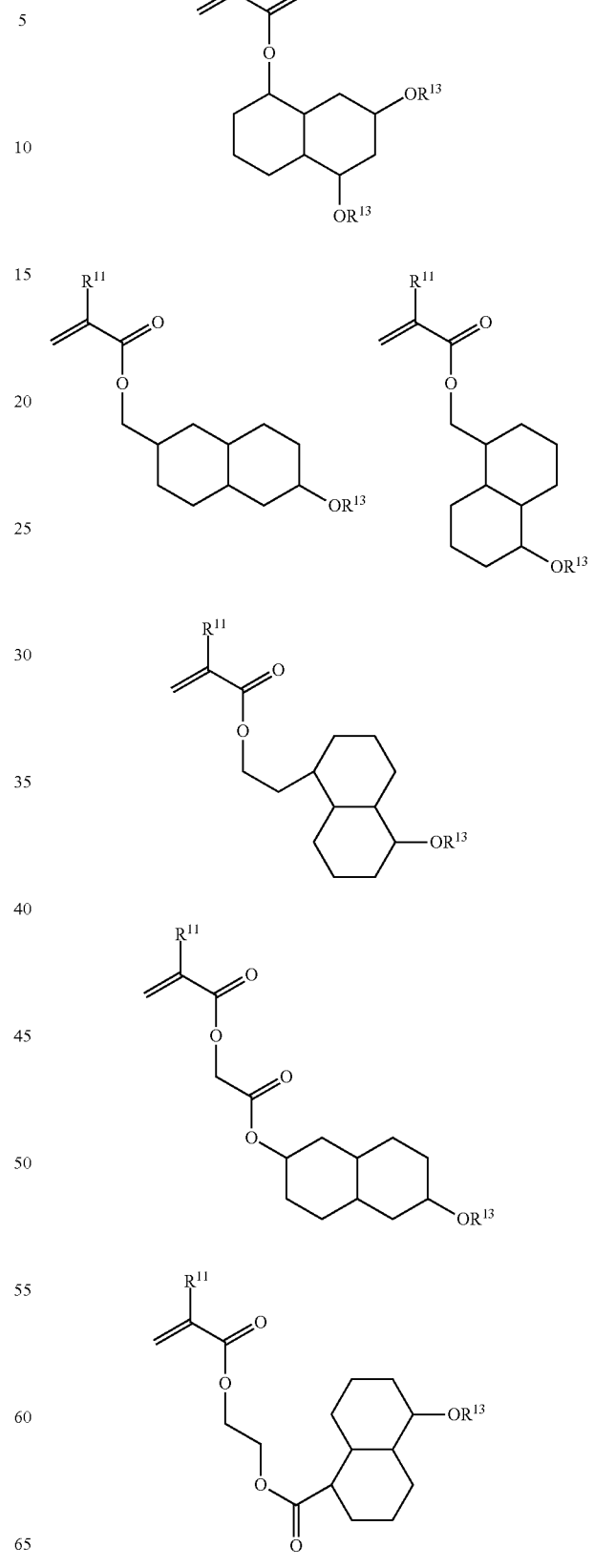

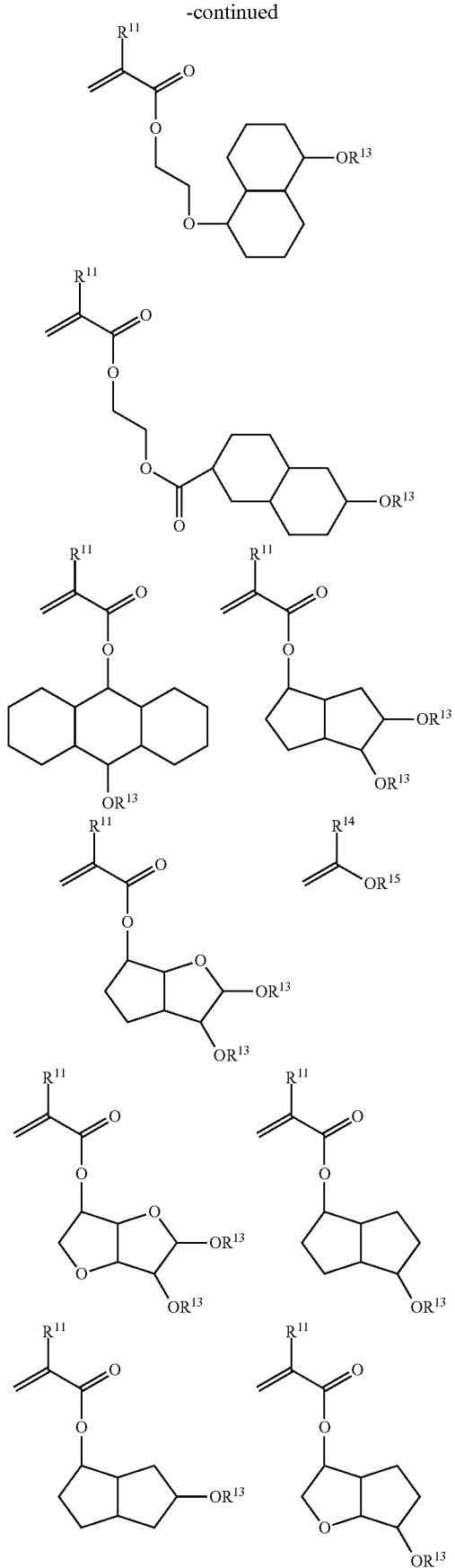
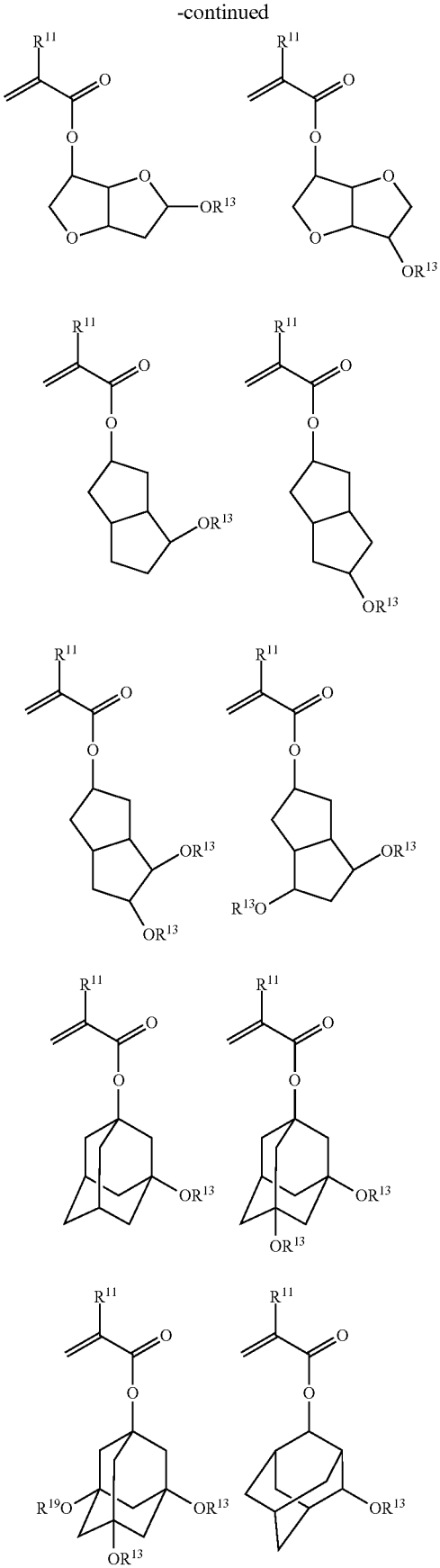

-continued

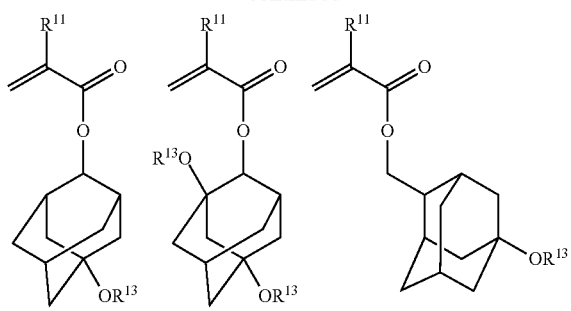

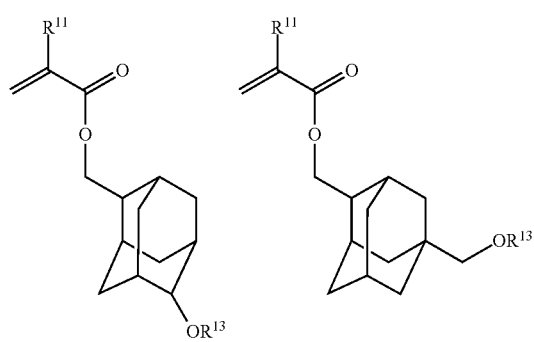

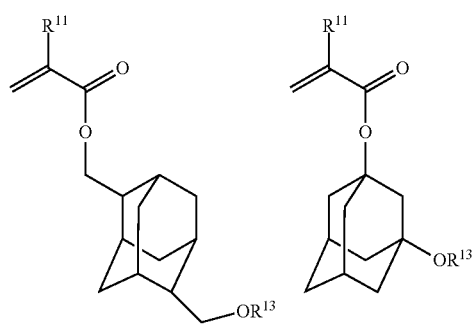

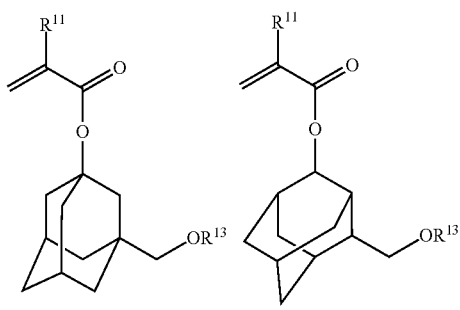

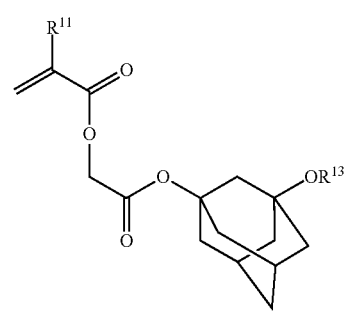

-continued

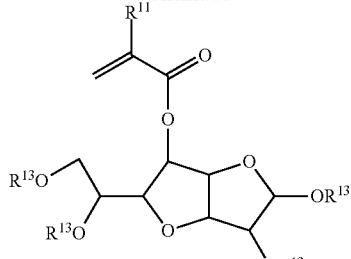

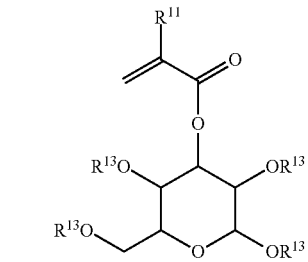

The polymer of the present invention may include a repeating unit derived from a monomer having a carbon-carbon double bond, including substituted acrylic acid esters such as methyl methacrylate, methyl crotonate, dimethyl maleate, and dimethyl itaconate, unsaturated carboxylic acids such as maleic acid, fumaric acid, and itaconic acid, cyclic olefins such as norbornene, norbornene derivatives, and tetracyclo [4.4.0.1$^{2,\ 5}$.1$^{7,\ 10}$] dodecene derivatives, and unsaturated acid anhydrides such as itaconic acid anhydride, and other monomers, in addition to the above-described compounds.

The weight average molecular weight in terms of polystyrene of the polymer of the present invention is determined by gel permeation chromatography (GPC) (solvent: tetrahydrofuran). It is 1,000 to 500,000, and preferably 3,000 to 100,000. When it falls within the range, the etching resistance may not largely decrease, and the resolution may not decrease even without a difference in dissolution rate before and after exposure.

In the polymer of the present invention, the preferable content of the repeating units derived from the respective monomers falls within the following range (mole %), but not limited to the range.

(I) more than 0 to 100 mole %, preferably 5 to 70 mole %, and more preferably 10 to 50 mole % of one or more constituent units represented by the formulae (2a) and (2b) derived from the monomers of the formulae (1a) and (1b); (II) 0 or more and less than 100 mole %, preferably 30 to 95 mole %, and more preferably 50 to 90 mole % of one or more constituent units of one or more represented by the formulae (3a) to (3d); (III) 0 to 30 mole %, preferably 0 to 20 mole %, and more preferably 0 to 10 mole % of one or more constituent units represented by the formulae (d1) to (d3) if necessary; and (IV) 0 to 80 mole %, preferably 0 to 70 mole %, and more preferably 0 to 50 mole % of one or more constituent units derived from other monomers, such as constituent units represented by the formulae (4a) and (4d), if necessary.

The polymer of the present invention is prepared by copolymerization reaction using the compounds represented by the general formulae (1a) and (1b) as first monomers and polymerizable double bond-bearing compounds as second and subsequent monomers.

The copolymerization reaction to prepare the polymer of the present invention may include various processes, and be preferably radical polymerization, anionic polymerization, or coordination polymerization.

For radical polymerization, preferable reaction conditions include (a) a solvent selected from hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile, and peroxides such as benzoyl peroxide and lauroyl peroxide, (c) a reaction temperature of about 0 to about 100° C., and (d) a reaction time of about 0.5 to about 48 hours. Reaction conditions outside this range may be employed.

For anionic polymerization, preferable reaction conditions include (a) a solvent selected from hydrocarbons such as benzene, ethers such as tetrahydrofuran, and liquid ammonia, (b) a polymerization initiator selected from metals such as sodium and potassium, alkyl metals such as n-butyl lithium and sec-butyl lithium, ketyl, and Grignard reagents, (c) a reaction temperature of about −78 to about 0° C., (d) a reaction time of about 0.5 to about 48 hours, and (e) a terminator selected from proton donating compounds such as methanol, halides such as methyl iodide, and electrophilic compounds. Reaction conditions outside the described range may be employed.

For coordination polymerization, preferable reaction conditions include (a) a solvent selected from hydrocarbons such as n-heptane and toluene, (b) a catalyst selected from Ziegler-Natta catalysts including a transition metal such as titanium, and alkylaluminum, Phillips catalysts of metal oxides having chromium or nickel compounds carried thereon, and olefin-metathesis mixed catalysts typified by tungsten and rhenium mixed catalysts, (c) a reaction temperature of about 0 to about 100° C., and (d) a reaction time of about 0.5 to about 48 hours. Reaction conditions outside the described range may be employed.

[Resist Composition]

Since the polymer of the present invention is suitably used as the base resin of a resist composition, and especially a chemically amplified positive resist composition, the present invention provides a resist composition containing the polymer, and especially a chemically amplified positive resist composition. In this case, the resist composition preferably contains (A) the polymer as a base resin; (B) an acid generator; (C) an organic solvent; if necessary, (D) a basic compound; and (E) a surfactant.

The addition of the acid generator (B) may be omitted when the polymer contains any repeating units of the formulae (d1) to (d3).

In addition to the polymer of the present invention, a resin for increasing a dissolution rate in alkaline developer under the action of acid may be added, if necessary, as the base resin of the component (A). Examples of the resin include, but are not limited to, i) a poly(meth)acrylic acid derivative, ii) a norbornene derivative-maleic anhydride copolymer, iii) a hydrogenated product of ring-opening metathesis polymerization polymer, and iv) a vinyl ether-maleic anhydride-(meth)acrylic acid derivative copolymer.

Of these, a method for synthesizing a hydrogenated product of ring-opening metathesis polymerization polymer is specifically described in Examples of Japanese Patent Laid-Open Publication No. 2003-66612. Specific examples thereof include, but not limited to, polymers having the following repeating units.

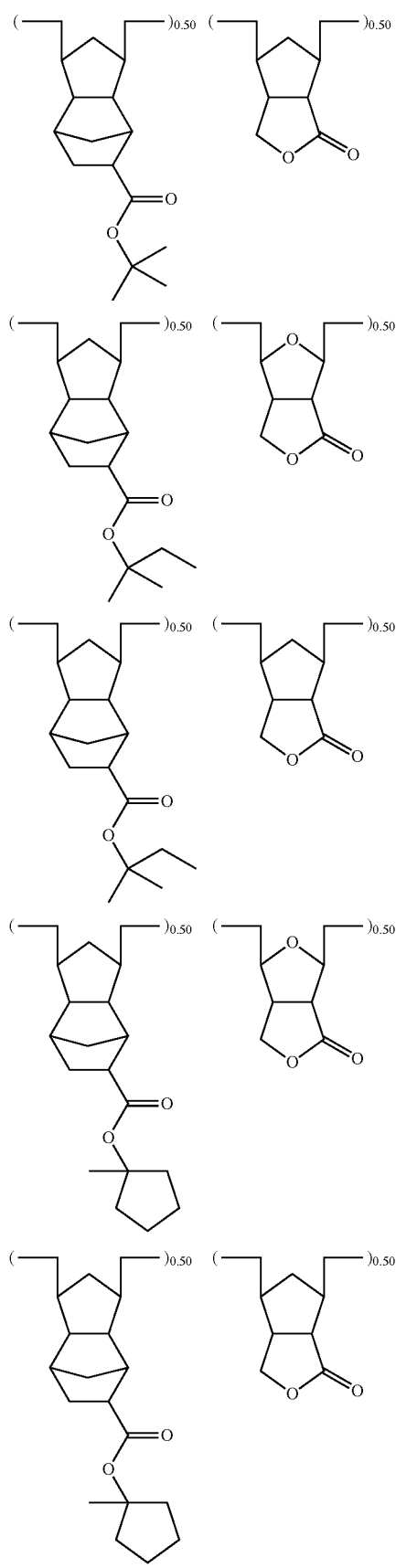

95
-continued
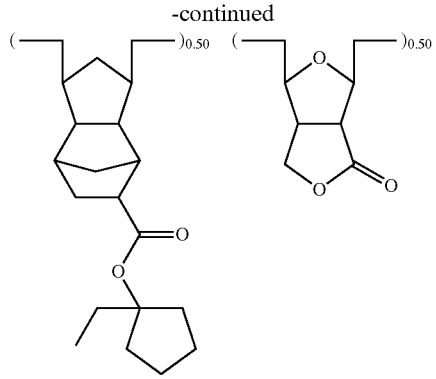
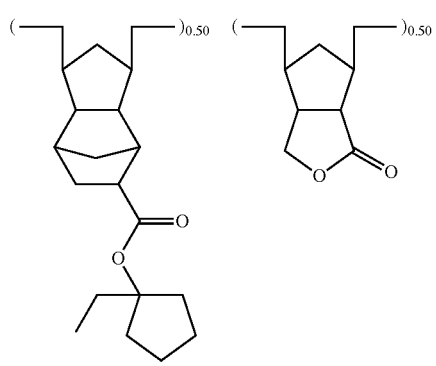
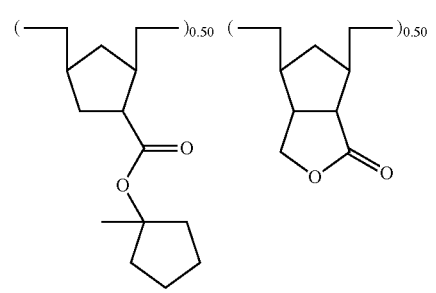
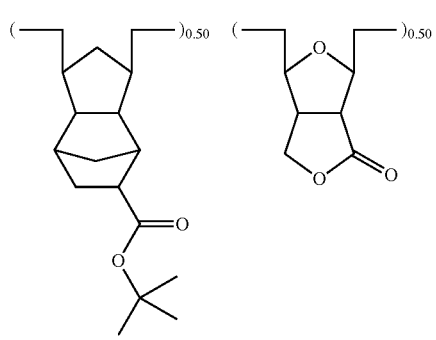
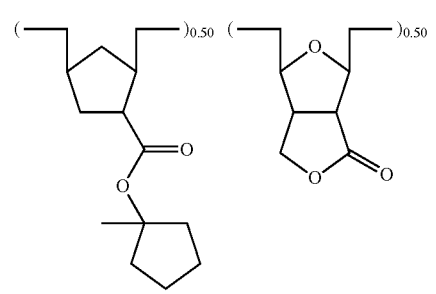
96
-continued
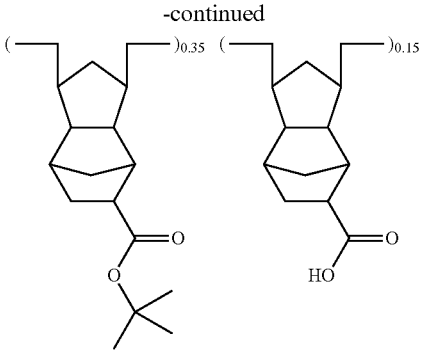
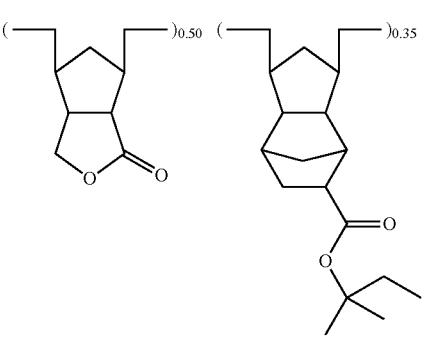
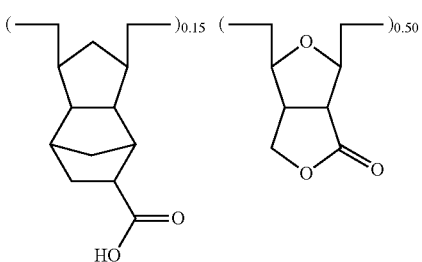
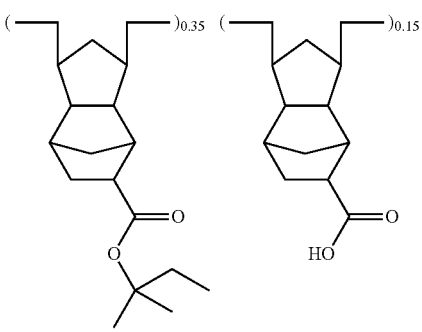
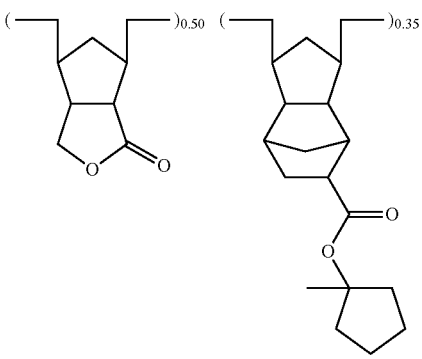

-continued

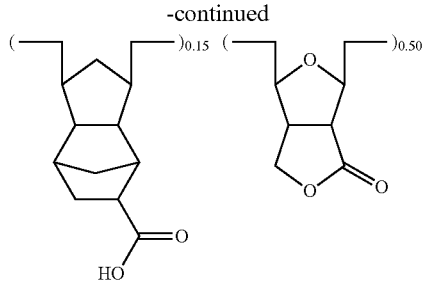
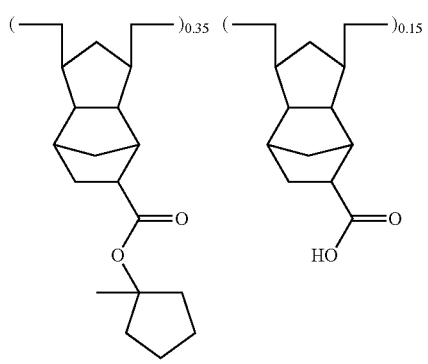
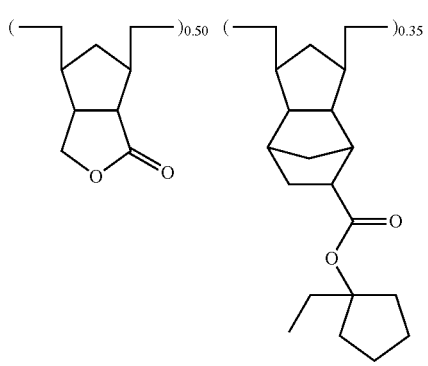
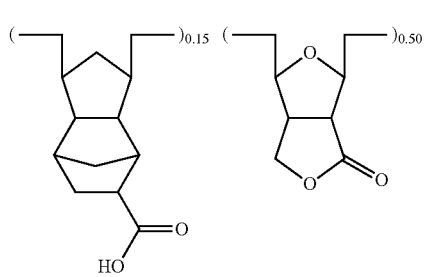
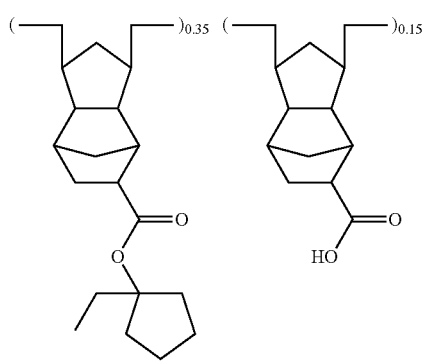

-continued

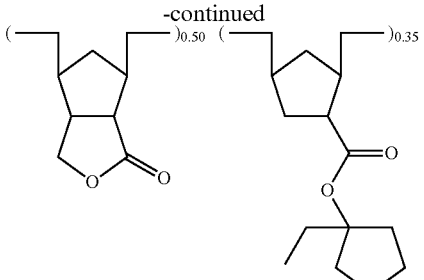
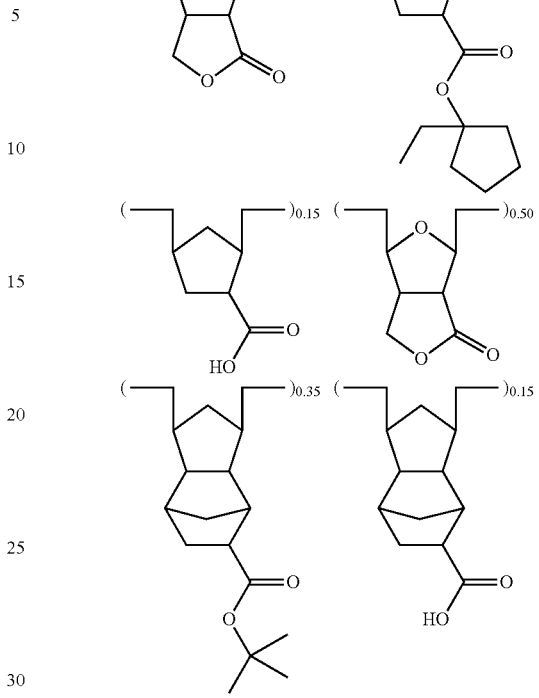
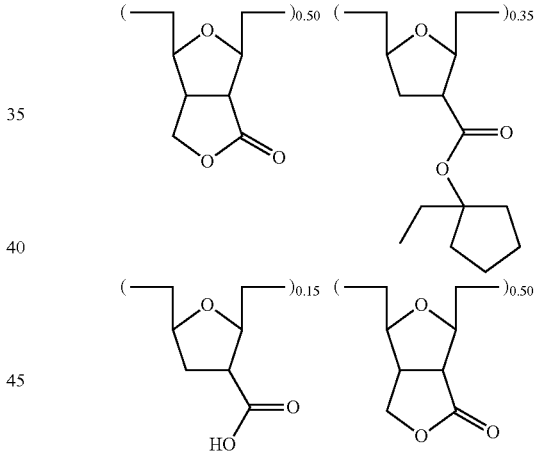

The combination ratio (by mass) of the polymer of the present invention and the other polymer preferably falls within a range of 100:0 to 10:90, and more preferably 100:0 to 20:80. The properties of the resist composition can be adjusted by properly changing the combination ratio.

The polymer is not limited to one kind and two or more polymers may be added. A plurality of polymers can be used to adjust the properties of the resist composition.

As the acid generator (B) used in the present invention, a photoacid generator may be added as long as the photoacid generator is a compound which generates an acid under high energy irradiation. Suitable examples of the photoacid generator may include a sulfonium salt, an iodonium salt, sulfonyldiazomethane, N-sulfonyloxyimide, and an oxime-O-sulfonate acid generator. Specific examples thereof are described in Japanese Patent Laid-Open Publication No. 2009-269953, paragraphs [0151] to [0156].

In particular, an acid generator represented by the following general formula (B)-1 is preferably used,

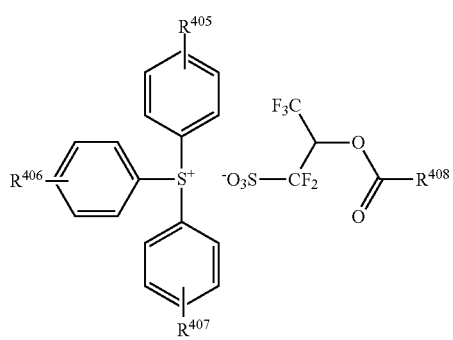

(B)-1 wherein $R^{405}$, $R^{406}$, and $R^{907}$ are each independently a hydrogen atom or a linear, a branched, or a cyclic monovalent hydrocarbon group having 1 to 20 carbon atoms and optionally containing a heteroatom, especially an alkyl group or an alkoxy group; and $R^{408}$ is a linear, a branched, or a cyclic monovalent hydrocarbon group having 7 to 30 carbon atoms and optionally containing a heteroatom.

Specific examples of the hydrocarbon groups and optionally containing a heteroatom of $R^{405}$, $R^{406}$, and $R^{407}$ may include a methyl group, an ethyl group, a propyl group, an isopropyl group, a n-butyl group, a sec-butyl group, a tert-butyl group, a tert-amyl group, a n-pentyl group, a n-hexyl group, a cyclopentyl group, a cyclohexyl group, an ethylcyclopentyl group, a butylcyclopentyl group, an ethylcyclohexyl group, a butylcyclohexyl group, an adamantyl group, an ethyladamantyl group, a butyladamantyl group, a group in which a heteroatom group such as —O—, —S—, —SO—, —SO$_2$—, —NH—, —C(=O)—, —C(=O)O—, and —C(=O)NH— is inserted between any carbon-carbon bonds thereof, and a group in which a functional group such as —OH, —NH$_2$, —CHO, and —CO$_2$H is substituted. $R^{408}$ represents a linear, a branched, or a cyclic monovalent hydrocarbon group having 7 to 30 carbon atoms and optionally containing a heteroatom, and specific examples may be, but not limited to, as follows.

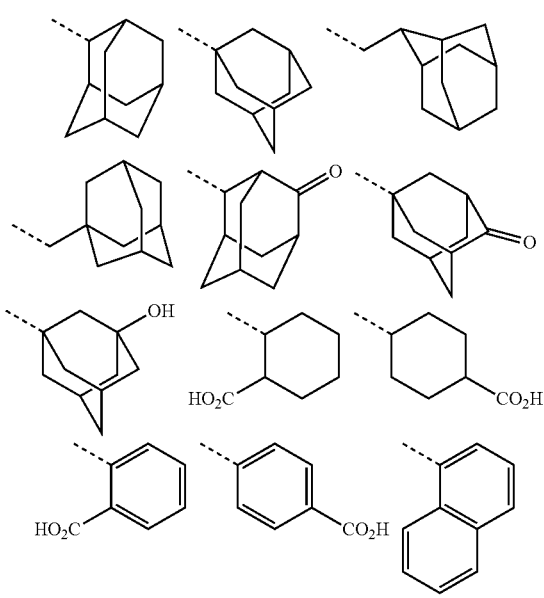

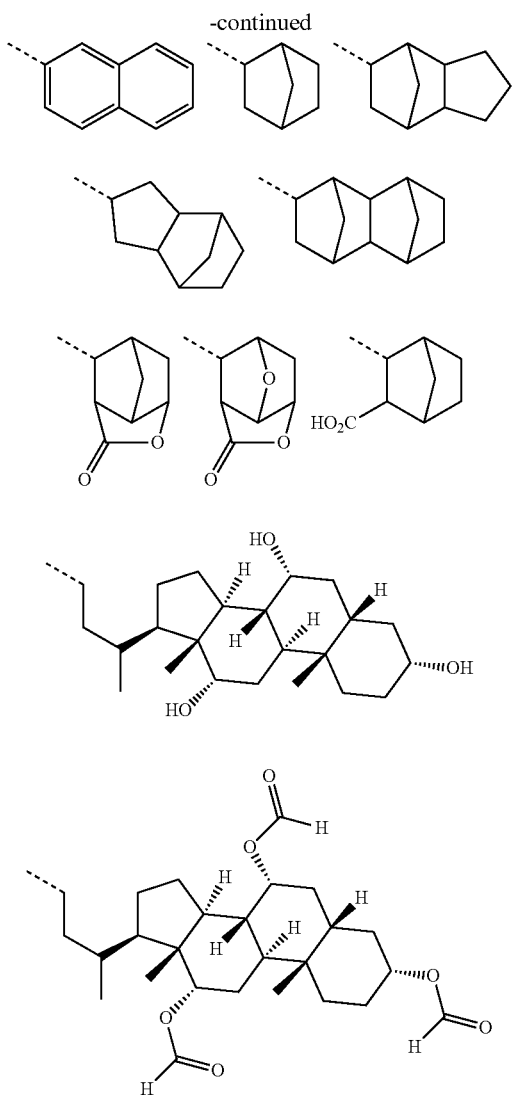

Specific examples of the acid generator of the formula (B)-1 may be, but not limited to, as follows.

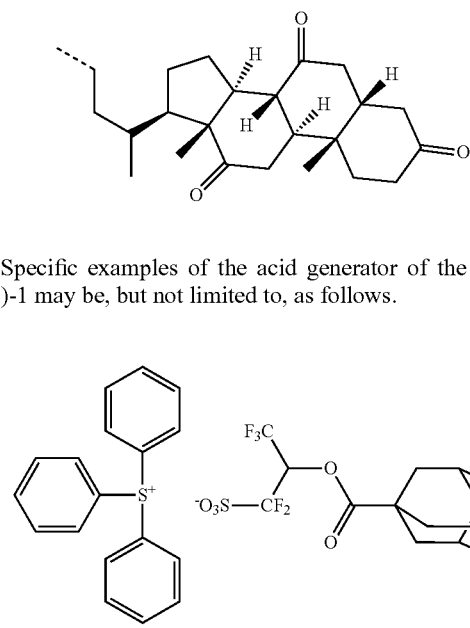

101
-continued
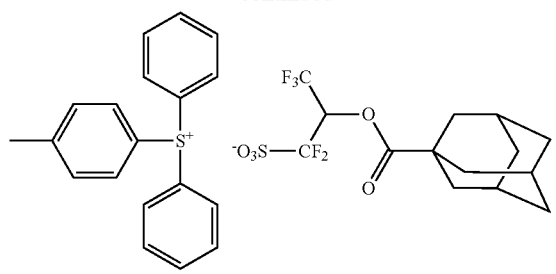
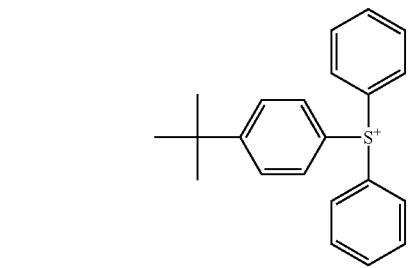
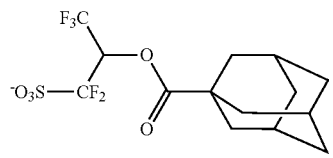
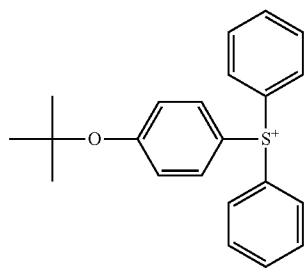
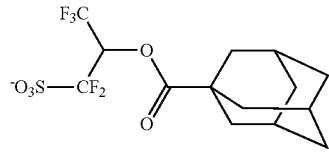
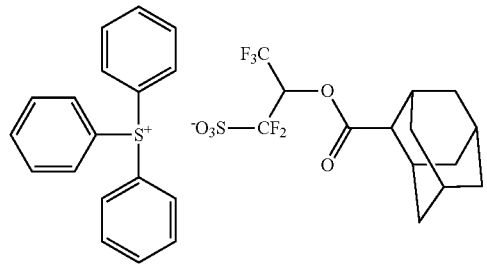
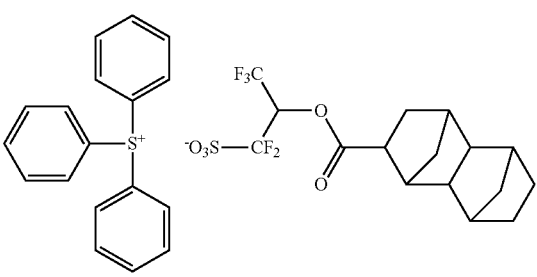
102
-continued
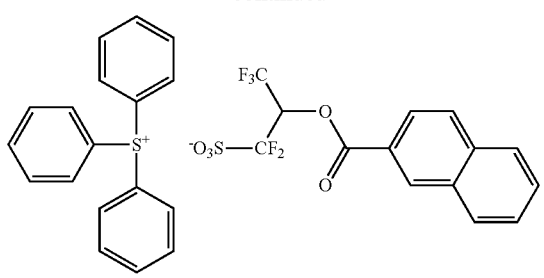
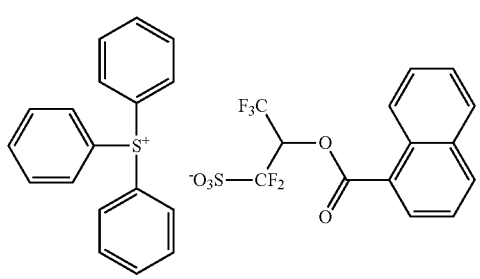
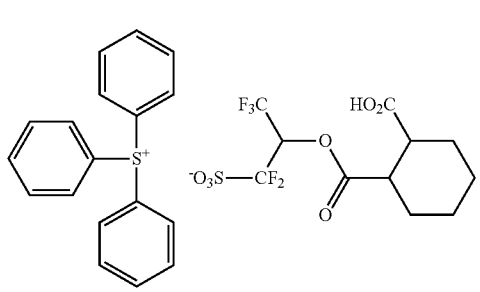
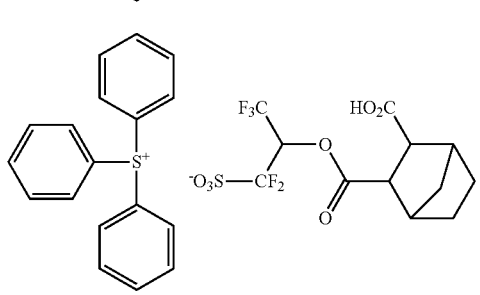
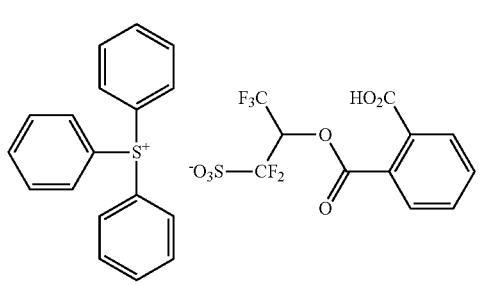
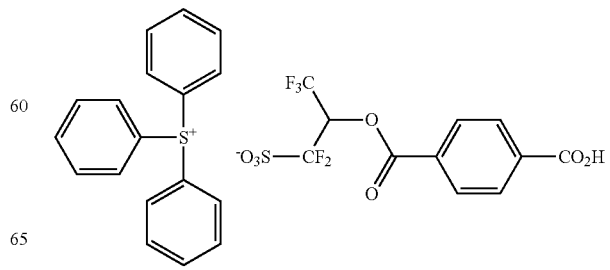

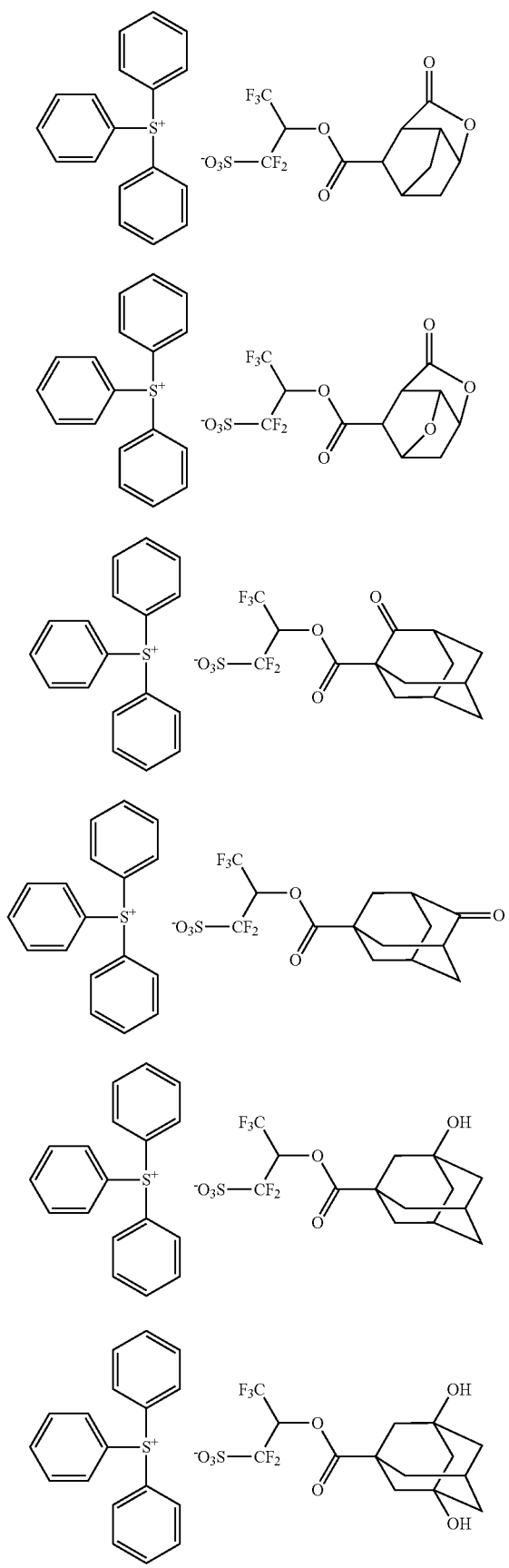

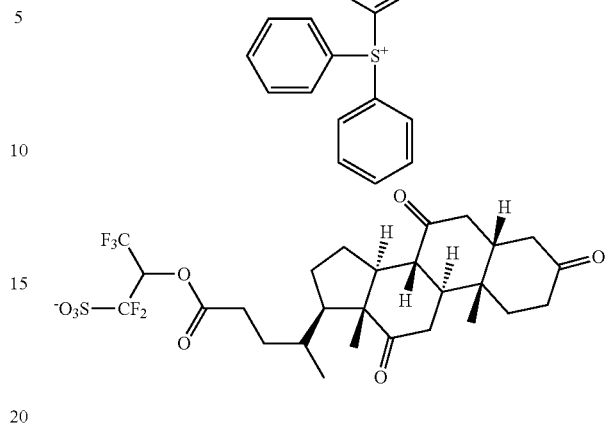

It is noted that an acid diffusion controlling function may be provided when two or more photoacid generators are used in mixture, in which one photoacid generator is an onium salt capable of generating a weak acid. Specifically, when a photoacid generator capable of generating a strong acid (e.g., fluorinated sulfonic acid) and an onium salt capable of generating a weak acid (e.g., unfluorinated sulfonic acid or carboxylic acid) are used in mixture, the strong acid generated from the photoacid generator upon high-energy irradiation collides with the unreacted onium salt having a weak acid anion, salt exchange occurs, and the weak acid is released to produce an onium salt having a strong acid anion. In this process, the strong acid is exchanged into a weak acid having a lower catalytic performance, and the acid is apparently deactivated to control acid diffusion.

If the photoacid generator capable of generating a strong acid is an onium salt, the strong acid generated upon high-energy irradiation can be exchanged into a weak acid as described above. However, salt exchange cannot occur by collision of the weak acid generated upon high-energy irradiation with the unreacted onium salt capable of generating a strong acid. This is because an onium cation is likely to form an ion pair with an anion of the stronger acid.

The addition amount of the photoacid generator is 0.1 to 40 parts by mass, and more preferably 0.1 to 20 parts by mass based on 100 parts by mass of the base resin (A) in the resin composition. When the amount of the photoacid generator is 40 parts by mass or less, the resist film has a fully high transmittance and the resolution performance is unlikely to deteriorate. The photoacid generators may be used alone or in a mixture of two or more kinds thereof. The transmittance of the resist film can be controlled by using a photoacid generator having a low transmittance at an exposure wavelength and adjusting the addition amount of the photoacid generator.

To the resist composition of the present invention, compounds which are decomposed by an acid to generate another acid (acid-amplifier compound) may be added. These compounds are described in J. Photopolym. Sci. and Tech., 8, 43-44, 45-46 (1995), and ibid., 9, 29-30 (1996).

Examples of the acid-amplifier compound may include tert-butyl-2-methyl-2-tosyloxymethyl acetoacetate and 2-phenyl-2-(2-tosyloxyethyl)-1,3-dioxolane, but are not limited thereto. Of known photoacid generators, many compounds having poor stability, especially poor thermal stability exhibit acid-amplifier compound-like properties.

In the resist composition of the present invention, the addition amount of the acid-amplifier compound is 2 parts by mass or less, and preferably 1 part by weight or less based on 100 parts by mass of the base resin. When it falls within this range, diffusion is easily controlled and the resolution and pattern profile do not deteriorate.

The organic solvent (C) used in the present invention may be any organic solvent in which a base resin, an acid generator, and other additives are soluble. Examples of such an organic solvent may include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylenegylcol monomethyl ether, ethylenegylcol monomethyl ether, propylenegylcol monoethyl ether, ethylenegylcol monoethyl ether, propylenegylcol dimethyl ether, and diethyleneglycol dimethyl ether; esters such as propylenegylcol monomethyl ether acetate, propylenegylcol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylenegylcol mono-tert-butyl ether acetate; and lactones such as γ-butyrolactone. These organic solvents may be used alone or in a mixture of two or more kinds thereof, but are not limited thereto. In the present invention, among these organic solvents, diethyleneglycol dimethyl ether, 1-ethoxy-2-propanol, propyleneglycol monomethyl ether acetate, and a mixture thereof are preferably used since the solubility of the acid generator contained in the resist components are excellent.

The use amount of the organic solvent is 200 to 1,000 parts by mass, and preferably 400 to 800 parts by mass based on 100 parts by mass of the base resin.

In the resist composition of the present invention, one or more kinds of basic compounds, such as an organic nitrogen-containing compound may be added as the component (D).

It is suitable that the organic nitrogen-containing compound be a compound capable of suppressing the diffusion rate when the acid generated by the photoacid generator diffuses within the resist film. The resist sensitivity is easily adjusted by addition of such a quencher. Further, the diffusion rate of the acid in the resist film may be suppressed to improve a degree of resolution. Changes in sensitivity after exposure may be suppressed, and a dependence on a substrate and an environment may be reduced to improve an exposure margin, a pattern profile, and the like.

Examples of the organic nitrogen-containing compounds may include primary, secondary, and tertiary aliphatic amines, mixed amines, aromatic amines, heterocyclic amines, nitrogen-containing compounds having a carboxyl group, nitrogen-containing compounds having a sulfonyl group, nitrogen-containing compounds having a hydroxyl group, nitrogen-containing compounds having a hydroxyphenyl group, alcoholic nitrogen-containing compounds, amides, imides, and carbamates. Specific examples thereof are disclosed in Japanese Patent Laid-Open Publication No. 2009-269953, paragraphs [0122] to [0141].

The amount of the organic nitrogen-containing compound to be added is preferably 0.001 to 8 parts by mass, and particularly preferably 0.01 to 4 parts by mass based on 100 parts by mass of the base resin. When the amount is 0.001 part by mass or more, the blending effect can be surely obtained. When the amount is 8 parts by mass or less, the sensitivity is not too low. It is suitable that the organic nitrogen-containing compound be a compound capable of suppressing the diffusion rate when an acid generated by the acid generator diffuses within the resist film. The addition of organic nitrogen-containing compound can suppress the rate of acid diffusion within the resist film to improve a degree of resolution. Further, changes in sensitivity after exposure can be suppressed and dependence on a substrate and an environment can be reduced to improve an exposure margin, a pattern profile, and the like.

As a quencher, onium salt such as sulfonium salts, iodonium salts, and ammonium salts of sulfonic acid which is not fluorinated at α-position as disclosed in Japanese Patent Laid-Open Publication No. 2008-158339, and of carboxylic acid as disclosed in Japanese Patent No. 3991462 can be used. Sulfonic acid, imidic acid, or methide acid which is fluorinated at α-position are necessary for deprotection of acid labile group of carboxylate ester. Sulfonic acid which is not fluorinated at α-position and carboxylic acid are released by salt exchange with an onium salt which is not fluorinated at α-position. The sulfonic acid which is not fluorinated at α-position and carboxylic acid function as a quencher since they do not cause a deprotection reaction. In addition, salt exchange with sulfonic acid, imidic acid, or methide acid, which is fluorinated at α-position varies onium salts of sulfonic acid which is not fluorinated at α-position and carboxylic acid into an acid generator which is sulfonic acid, imidic acid, or methide acid, which is fluorinated at α-position. As an exposure dose is increased, the generation of sulfonic acid, imidic acid, or methide acid, which is fluorinated at α-position and salt exchange with a sulfonium salt are repeated without end. After exposure, a position where sulfonic acid, imidic acid, or methide acid is generated is different from a first position of sulfonium salt of sulfonic acid, imidic acid, or methide acid. A large number of cycles of generation of acid by light, salt exchange, and generation of acid average positions of generation of acid. As a result, the resist pattern edge roughness after development is decreased.

Since the sulfonium salts or iodonium salts of sulfonic acid which is not fluorinated at α-position and carbonic acid have photodegradability, the quenching capacity of a moiety having a high light intensity is decreased, and the concentration of sulfonic acid, imidic acid, or methide acid, which is fluorinated at α-position is increased. Thus, the contrast in an exposed area is improved. In formation of negative tone by an organic solvent, the rectangle property of negative pattern is increased with improving contrast in an exposed area. Onium salts such as sulfonium salts, iodonium salts, or ammonium salts of sulfonic acid which is not fluorinated at α-position and carbonic acid have a high effect of suppressing diffusion of sulfonic acid, imidic acid, or methide acid which is fluorinated at α-position. This is because exchanged onium salts with a large molecular weight suppress the movement. When a hole pattern is formed by negative development, there are many areas of generating an acid. Therefore, it is important to control an acid that diffuses from an exposed area to a non-exposed area. From the viewpoints of control of acid diffusion, onium salts such as sulfonium salts, iodonium salts, or ammonium salts of sulfonic acid which is not fluorinated at α-position and carbonic acid and the addition of a carbamate compound which generates an amine compound by an acid are important.

When an acid labile group is acetal that is particularly sensitive to an acid, an acid for eliminating a protecting group is not necessarily sulfonic acid, imidic acid, or methide acid, which is fluorinated at α-position. Even in sulfonic acid which is not fluorinated at α-position, a deprotection reaction may proceed. In this case, it is preferable that an onium salt of carboxylic acid be used as a quencher.

To the resist composition of the present invention, a surfactant which is commonly used for improvement of coating property as the component (E) may be added. The amount of the surfactant to be added in the component (E) is a conventional amount.

It is preferable that the surfactant is a nonionic surfactant, and examples thereof may include a perfluoroalkylpolyoxyethylene ethanol, a fluorinated alkyl ester, a perfluoroalkylamine oxide, a perfluoroalkyl EO-addition product, and a fluorine-containing organosiloxane compound. Further, examples may include Fluorad FC-430 and FC-431 (available from Sumitomo 3M, Ltd.), SURFLON S-141, S-145, KH-10, KH-20, KH-30 and KH-40 (available from Asahi Glass Co., Ltd.), UNIDYNE DS-401, DS-403 and DS-451 (available from Daikin Industries, Ltd.), MEGAFACE F-8151 (available from Dainippon Ink & Chemicals, Inc.), and X-70-092 and X-70-093 (available from Shin-Etsu Chemical Co., Ltd.). Preferable surfactants are Fluorad FC-430 (available from Sumitomo 3M, Ltd.), KH-20 and KH-30 (available from Asahi Glass Co., Ltd.), and X-70-093; (available from Shin-Etsu Chemical Co., Ltd.).

In addition to the above-described components, a polymer may be optionally added to the resist composition of the present invention, which be locally distributed at the top of a coating and functions to adjust a hydrophilic and hydrophobic balance on the surface, to enhance water repellency, or to prevent low-molecular-weight components from flowing into or out of the coating when the coating comes in contact with water or other liquids. The amount of the polymer to be added is a conventional amount, preferably 15 parts by mass or less, and particularly preferably 10 parts by mass or less based on 100 parts by mass of the base resin.

Preferable examples of the polymer which is locally distributed at the top of a coating may include polymers and copolymers containing one or more kinds of fluorinated units, and copolymers containing fluorinated units and other units. The fluorinated units and other units are specifically, but not limited to, as follows.

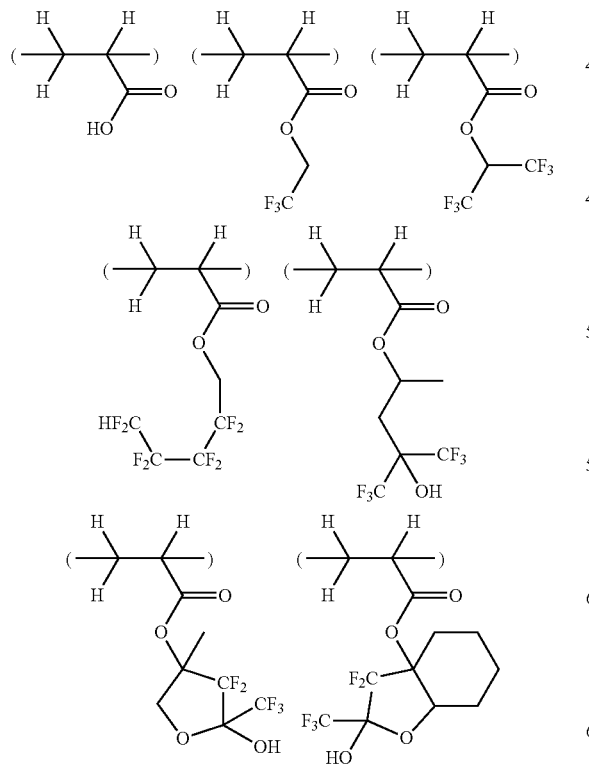

-continued

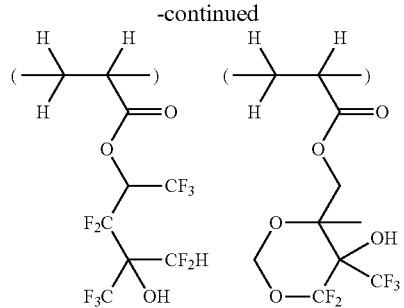

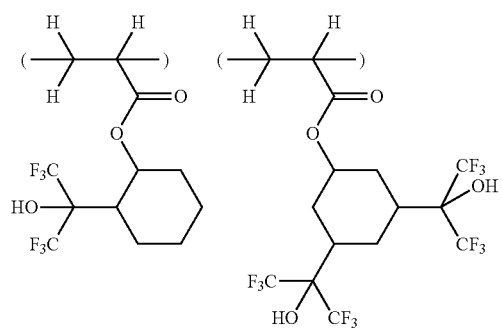

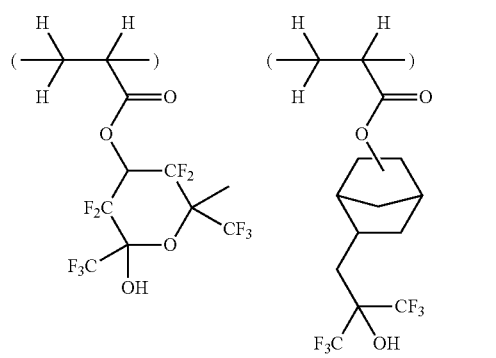

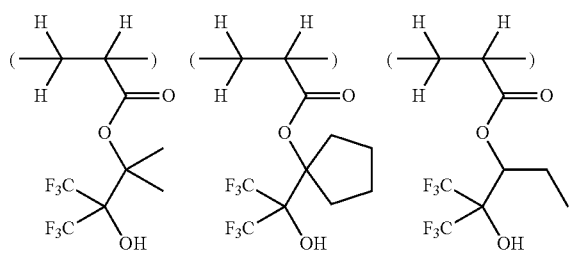

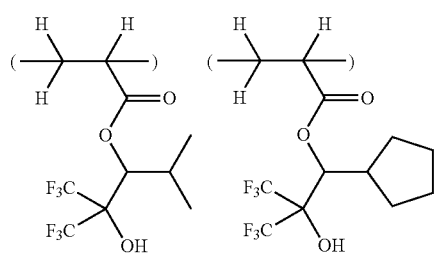

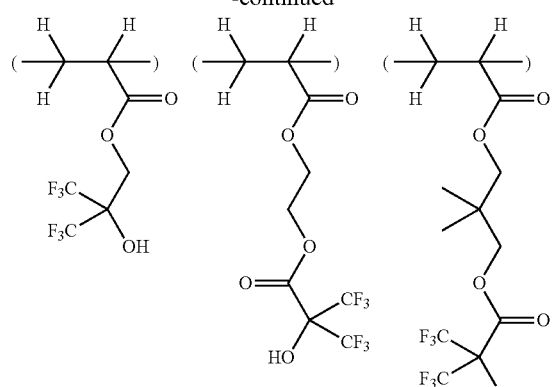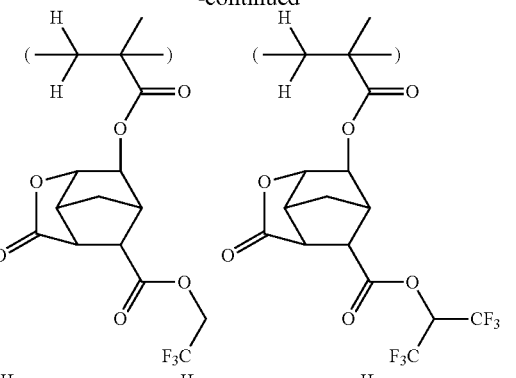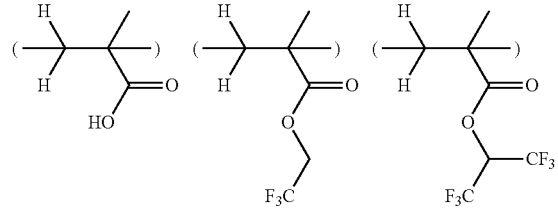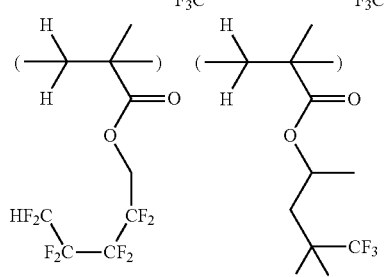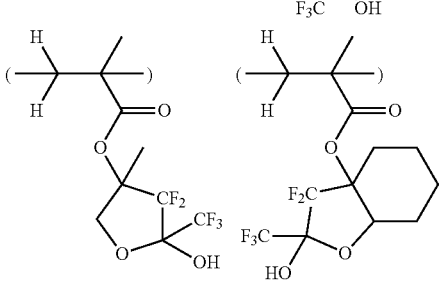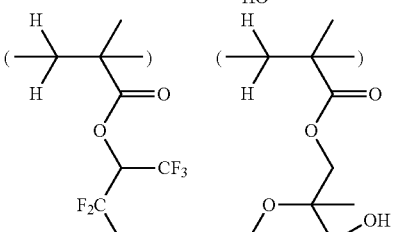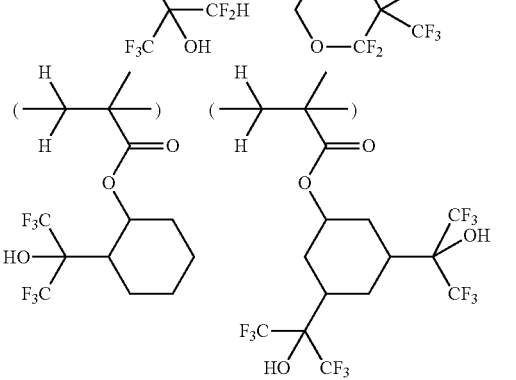

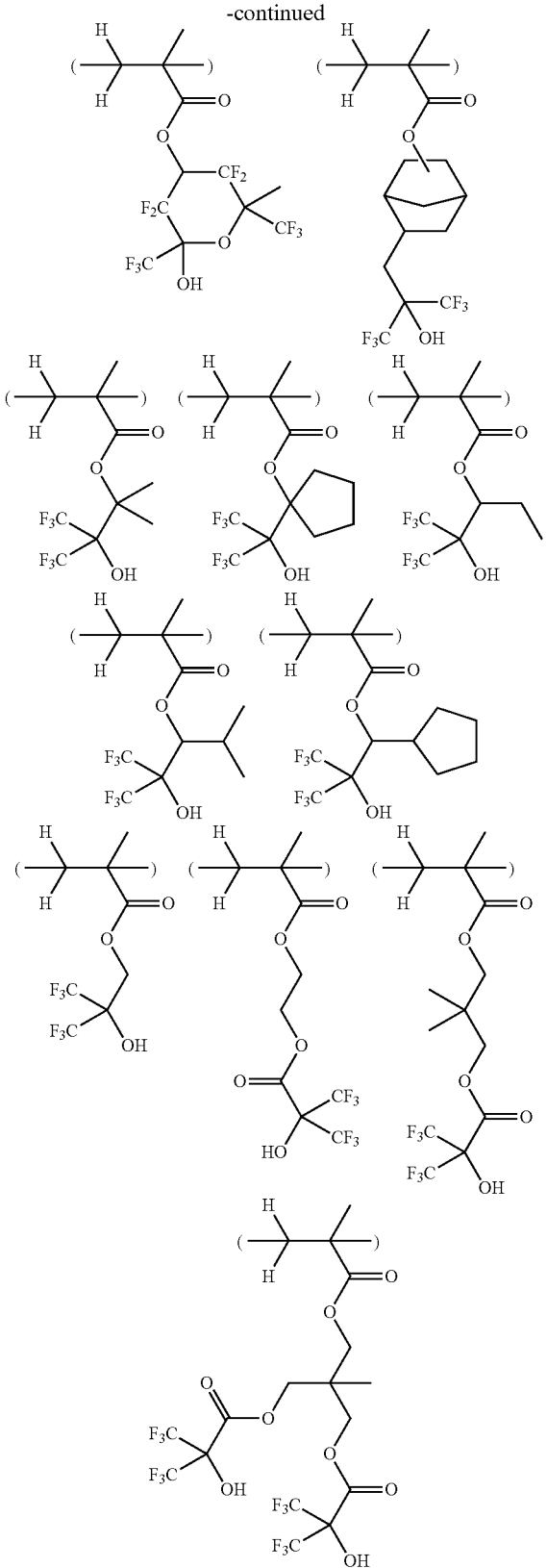

A polymer containing the repeating unit (2a) or (2b) of the present invention may be added as a water repellent.

The weight average molecular weight of the polymer locally distributed at the top of a coating is preferably 1,000 to 50,000, and more preferably 2,000 to 20,000. When it falls within the range, the polymer may not have a sufficient surface-modifying effect or cause development defects. The weight average molecular weight is a value in terms of polystyrene determined by gel permeation chromatography (GPC).

The resist composition of the present invention typically contains a polymer, an acid generator, an organic solvent, and an organic nitrogen-containing compound as described above as components. In addition to the components, optional other ingredients such as a dissolution inhibitor, an acidic compound, a stabilizer, and a dye may be added if necessary. The addition amounts of the ingredients are conventional amounts.

A pattern may be formed using the resist composition of the present invention by known lithography techniques. The steps including coating, heat treatment (prebaking), exposure, heat treatment (post-exposure baking, PEB), and development may be performed to form a pattern. If necessary, any additional steps may be added.

For formation of a pattern, the resist composition of the present invention is first applied to a substrate on which an integrated circuit is to be formed (e.g., Si, $SiO_2$, SiN, SiON, TiN, WSi, BPSG, SOG, organic anti-reflection film, Cr, CrO, CrON, and MoSi) by an appropriate coating method such as spin coating, roll coating, flow coating, dip coating, spray coating, or doctor coating so that the film thickness is 0.01 to 2.0 μm. The film is prebaked on a hot plate at 60 to 150° C. for 1 to 10 minutes, and preferably 80 to 140° C. for 1 to 5 minutes.

From the viewpoints of film thickness reduction of a resist film and selectivity ratio of etching of a substrate to be processed, processing becomes difficult. Therefore, a three-layer process is under investigation, in which a silicon-containing intermediate film is laminated under a resist film, an underlayer film having a high carbon density and etching resistance is laminated under the intermediate film, and a substrate to be processed is laminated under the film. Since the ratio of etching selectivity of a silicon-containing intermediate film and an underlayer film using an oxygen gas, a hydrogen gas, or an ammonia gas is high, the silicon-containing intermediate film can be made thinner. Since the ratio of etching selectivity of a monolayer resist and a silicon-containing intermediate layer is also comparatively high, the monolayer resist can be made thinner. In this case, a process for forming an underlayer film includes a process including coating and baking and a process using CVD. A coating-type underlayer film may be formed using a novolak resin or a resin obtained by polymerization of an olefin having a condensed ring. A CVD film may be formed using a gas of butane, ethane, propane, ethylene, or acetylene. A silicon-containing intermediate layer includes a coating-type layer and a CVD layer. Examples of the coating-type layer may include silsesquioxanes, and cage-like polyhedral oligomeric silsesquioxanes (POSSs). As a starting material for the CVD layer, various silane gasses are used. A silicon-containing intermediate layer may have an anti-reflection function with light absorption, and be a light absorbing group such as a phenyl group or a SiON film. An organic film may be formed between a silicon-containing intermediate film and a photoresist. In this case, the organic film may be an organic anti-reflection film. After formation of a photoresist film, acid generators may be extracted from the surface of the film by rinsing with pure water (post-soak), particles may be washed off, or a top coat may be applied.

Then, exposure is performed through a prescribed mask for forming a desired pattern by using a light source selected from a ultraviolet beam, a far-ultraviolet beam, an electronic beam, an X-ray, an excimer laser, a γ beam, and a synchrotron radiation beam. The exposure dose is preferably about 1 to about 200 mJ/cm$^2$, and particularly preferably about 10 to about 100 mJ/cm$^2$. Then, a post-exposure bake (PEB) is performed on a hot plate at 60 to 150° C. for 1 to 5 minutes, and preferably at 80 to 120° C. for 1 to 3 minutes. Development is performed using as a developer of an alkali aqueous solution such as a 0.1 to 5% by mass, preferably 2 to 3% by mass tetramethylammonium hydroxide (TMAH) by the ordinary method such as dipping, puddling, or spraying for 0.1 to 3 minutes, and preferably 0.5 to 2 minutes to form the desired pattern on the substrate. The resist composition of the present invention is most suitable for fine patterning preferably by a far-ultraviolet beam with a wavelength of 254 to 193 nm, an extreme ultraviolet beam with a wavelength of 157 nm, an electron beam, a soft X-ray, a X-ray, an excimer laser, a γ beam, a synchrotron radiation beam, and more preferably a high-energy beam with a wavelength of 180 to 200 nm.

The resist composition of the present invention can be used in immersion lithography. In ArF immersion lithography, pure water or a liquid having an index of refraction of 1 or more and high transparent at the exposure wavelength, such as alkane, may be used as a solvent for immersion. In the immersion lithography, pure water or other liquid is inserted between the prebaked resist film and a projection lens. Thus, a lens with a NA of 1.0 or more can be designed, and therefore a finer patterning can be performed. The immersion lithography is important for the ArF lithography to survive to the 45 nm node, and a further development thereof is accelerated. In the immersion lithography, rinsing with pure water (post-soak) may be performed after exposure to remove droplets of water remained on a resist film, or a top coat may be formed on the prebaked resist film to prevent a substance from eluting from the resist film and increase the water-sliding property of the film surface.

For a resist top coat used in immersion lithography, a polymer having a 1,1,1,3,3,3-hexafluoro-2-propanol residue, which is insoluble in water and soluble in an alkaline developer, is preferably used as a base and a material which is dissolved in an alcohol solvent having 4 or more carbon atoms, an ether solvent having 8 to 12 carbon atoms, or a mixed solvent thereof is preferable.

The polymer containing the repeating unit (2a) or (2b) of the present invention may be used as a material for a top coat.

As described above, the positive resist composition is applied to a substrate to form a resist film, the resist film is baked, and a predetermined area of the resist film is exposed to irradiation of a high-energy beam, and baked. A non-exposed area of the resist film is dissolved in a developer of an organic solvent to leave the exposed area as a film. Thus, a negative-tone resist pattern such as a hole or a trench can be formed.

Preferable examples of the developer to be used may include ketones such as 2-octanone, 2-nonanone, 2-heptanone, 3-heptanone, 4-heptanone, 2-hexanone, 3-hexanone, diisobutyl ketone, methyl cyclohexanone, acetophenone, and methyl acetophenone; and esters such as propyl acetate, butyl acetate, isobutyl acetate, amyl acetate, butenyl acetate, isoamyl acetate, methyl propionate, ethyl propionate, ethyl 3-ethoxypropionate, phenyl acetate, propyl formate, butyl formate, isobutyl formate, amyl formate, isoamyl formate, methyl valerate, methyl pentenoate, methyl crotonate, ethyl crotonate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, benzyl acetate, methyl phenylacetate, benzyl formate, phenylethyl formate, methyl 3-phenylpropionate, benzyl propionate, ethyl phenylacetate, and 2-phenylethyl acetate.

After the completion of development, rinsing is performed. It is preferable that a rinsing liquid be a solvent which is mixed and dissolved in a developer, but cannot dissolve a resist film. As such a solvent, an alcohol having 3 to 10 carbon atoms, an ether compound having 8 to 12 carbon atoms, an alkane, an alkene, or an alkyne having 6 to 12 carbon atoms, or an aromatic solvent is preferably used.

Examples of the alkane having 6 to 12 carbon atoms may include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Examples of the alkene having 6 to 12 carbon atoms may include hexene, heptene, octene, cyclohexene, methylcyclohexene, dimethylcyclohexene, cycloheptene, and cyclooctene. Examples of the alkyne having 6 to 12 carbon atoms may include hexyne, heptyne, and octyne. Examples of the alcohol having 3 to 10 carbon atoms may include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-amyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol.

The ether compound having 8 to 12 carbon atoms represents one or more kinds of solvents selected from di-n-butyl ether, diisobutyl ether, di-sec-butyl ether, di-n-pentyl ether, diisopentyl ether, di-sec-pentyl ether, di-tert-amyl ether, and di-n-hexyl ether.

In addition to the solvents, an aromatic solvent such as toluene, xylene, ethylbenzene, isopropylbenzene, tert-butylbenzene, or mesitylene can be used. Further, a developer may be dried by spin-drying and baking without rinsing.

A reversed hole pattern can be shrunk by RELACS (trademark) technique. A shrinking agent is applied to a hole pattern. An acid catalyst diffuses from a resist layer during baking to cross-link the shrinking agent on the surface of the resist. Thus, the shrinking agent adheres to the side wall of the hole pattern. The baking temperature is 70 to 180° C., and preferably 80 to 170° C., and the baking time is 10 to 300 seconds. An extra shrinking agent is removed to shrink the hole pattern. The shrinking agent can be removed by using water, a developer, an alcohol solvent, or a mixture thereof. When a conventional resist polymer in which a carboxyl group is substituted with an acid labile group is used to perform negative development with an organic solvent, a left resist film is an alkali soluble film containing a carboxyl group. Therefore, when an alkaline developer is used in separation of a shrinking agent, the developer dissolves not only the shrinking agent but also the resist film. As a result, the whole pattern does not remain. However, when a resist base polymer of the present invention in which a hydroxy group is substituted with an acid labile group is used, a resist film after deprotection is not dissolved in an alkaline developer. Accordingly, an alkaline developer can be used to separate a shrinking agent.

When a hole pattern is formed by negative-tone development, light of the highest contrast can be used by exposure to dipole illumination of two X- and Y-direction line patterns. The contrast can be further enhanced by combining dipole illumination with s-polarized illumination.

There is a double patterning process as a technique enabling ArF lithography to survive to the 32 nm node. The double patterning process include a trench process including processing an underlay to a 1:3 trench pattern by first exposure and etching, shifting the position, and forming a 1:3 trench pattern by second exposure to form a 1:1 trench pattern; and a line process including processing a first underlay to a 1:3 isolated left pattern by first exposure and etching, shifting the position, processing a second underlay formed below the first underlay by second exposure through the 1:3 isolated left pattern to form a half-pitch 1:1 pattern.

EXAMPLES

Hereinafter, the present invention will be specifically described with reference to Synthesis Examples, Examples, and Comparative Examples, but the present invention is not limited to the following Examples. In the following formulae, Me represents a methyl group.

Synthesis Example 1

A polymerizable ester compound of the present invention was synthesized by the following scheme.

Synthesis Example 1-1

Synthesis of Monomer 1

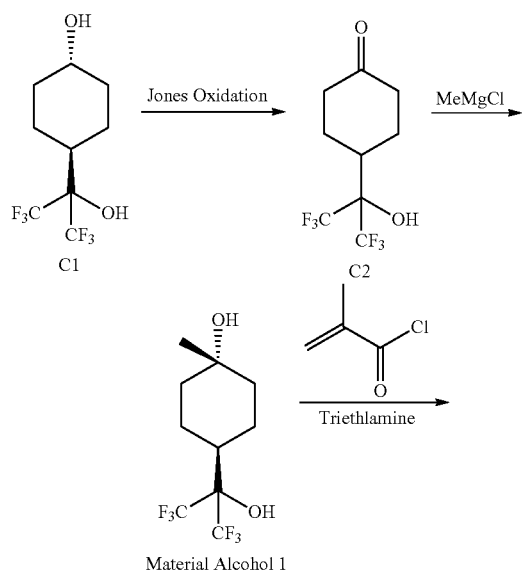

Material Alcohol 1

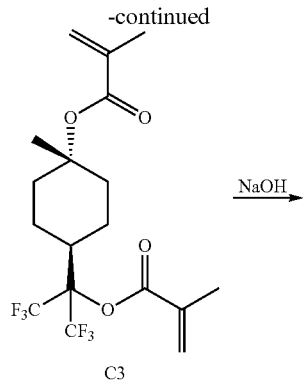

C3

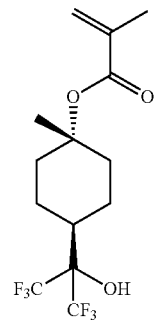

Monomer 1

Synthesis Example 1-1-1

Synthesis of Ketone Compound C2

26.0 g of alcohol compound C1 (major isomer (formula described above): minor isomer=73 mole %: 27 mole %) was dissolved in 65 mL of acetone, and the solution was ice-cooled. To the solution, 54.7 g (800 g/mol) of Jones reagent was added dropwise under a nitrogen atmosphere. The mixture was warmed to normal temperature, and stirred for 3.5 hours. Isopropyl alcohol was added to stop the reaction. After a usual aqueous work-up, the solvent was removed to obtain 25.0 g of ketone compound C2 (crude yield: 89%). The crude product was of sufficient purity and used for the next reaction without further purification.

IR (D-ATR): ν=3310, 2992, 2889, 1702, 1474, 1457, 1358, 1304, 1256, 1184, 1136, 1076, 981, 934 cm$^{-1}$.

$^1$H-NMR (600 MHz in DMSO-$d_6$): δ=1.61 (2H, dd), 2.13-2.29 (4H, m), 2.36-2.51 (3H, m), 7.88 (1H, s) ppm.

$^{19}$F-NMR (564 MHz in DMSO-$d_6$, trifluoroacetic acid standard (hereinafter as the same)): δ=−73.14 (6F, s)

Synthesis Example 1-1-2

Synthesis of Starting Material Alcohol 1

Methyl chloride gas bubbled through a solution of 6.6 g of magnesium in THF. The bubbling was stopped, and the solution was heated. When the solution became clouded, the heating was stopped, and THF in a total amount of 126 mL was gradually added under bubbling of methyl chloride gas. The mixture was stirred at 50 to 60° C. for 1.5 hours, the bubbling of ethyl chloride gas was stopped, and the mixture was ice-cooled. A solution of 24.8 g of ketone compound C2 in 50 mL of THF was added dropwise at 30° C. or lower under a nitrogen atmosphere, and the mixture was stirred at normal temperature for 19 hours. An aqueous solution of ammonium chloride was then added, and 20% hydrochloric acid was added to stop the reaction. After a usual aqueous work-up, the solvent was distilled off to obtain 26.0 g of starting material alcohol 1 (crude yield: 101%). The crude product was of sufficient purity and used for the next reaction without further purification. The product has a mixing ratio of isomers, major isomer:minor isomer, of 59 mole %: 41 mole %.

IR (D-ATR): ν=3520, 3486, 3197, 2957, 2941, 2902, 2858, 1448, 1410, 1365, 1280, 1200, 1123, 1073, 938, 902 cm$^{-1}$.

$^1$H-NMR (600 MHz in DMSO-d$_6$, draw only major isomer): δ=1.07 (3H, s), 1.16-1.35 (3H, m), 1.55-1.67 (4H, m), 1.76-1.87 (2H, m), 4.37 (1H, s), 7.58 (1H, s) ppm.

$^{19}$F-NMR (564 MHz in DMSO-d$_6$): δ=−73.03 (6F, s)

Synthesis Example 1-1-3

Synthesis of Bismethacrylate Compound C3

23.6 g of triethylamine was added dropwise to a mixture of 22.8 g of starting material alcohol 1, 23.6 g of methacryloyl chloride, and 86 mL of acetonitrile at normal temperature under a nitrogen atmosphere with stirring. The reaction mixture was stirred at room temperature overnight, and 46 g of water, 69 g of an aqueous solution of saturated sodium hydrogencarbonate, and 4-dimethylaminopyridine in a catalyst amount were successively added. Then, the mixture was stirred at room temperature for 1 hour. The reaction mixture was subjected to a usual aqueous work-up, and the solvent was distilled off. The resultant was purified by silica gel chromatography to obtain 26.7 g of bismethacrylate compound C3 (yield: 76%). The purified product has a mixing ratio of isomers, major isomer:minor isomer, of 58 mole %: 42 mole %.

IR (D-ATR): ν=2968, 1750, 1715, 1638, 1451, 1379, 1303, 1265, 1217, 1133, 1098, 1058, 1010, 953 cm$^{-1}$.

$^1$H-NMR (600 MHz in DMSO-d$_6$, draw only major isomer): δ=1.33 (1H, td), 1.52 (1H, s), 1.58 (3H, s), 1.61-1.73 (3H, m), 1.76-1.82 (1H, m), 1.88 (3H, s), 1.96 (3H, s), 2.30-2.36 (2H, m), 3.05-3.15 (1H, m), 5.47-5.50 (1H, m), 5.71-5.75 (1H, m), 5.98 (1H, s), 6.20 (1H, s)

$^{19}$F-NMR (564 MHz in DMSO-d$_6$): δ=−68.65 (6F, s)

Synthesis Example 1-1-4

Synthesis of Monomer 1

28.6 g of bismethacrylate compound C3 was dissolved in 150 g of 2-methyl-2-propanol at room temperature under a nitrogen atmosphere. 65.2 g of aqueous solution of 8% sodium hydroxide was added dropwise, and the mixture was stirred for 22 hours. Then, 120 g of 5% hydrochloric acid was added to stop the reaction. The reaction mixture was subjected to a usual aqueous work-up, and the solvent was distilled off. The resultant was purified by silica gel chromatography to obtain 23.2 g of monomer 1 (yield: 97%). The purified product has a mixing ratio of isomers, major isomer:minor isomer, of 58 mole %: 42 mole %.

IR (D-ATR): ν=3392, 2978, 1698, 1635, 1451, 1380, 1314, 1270, 1210, 1133, 1076, 1009, 936 cm$^{-1}$.

$^1$H-NMR (600 MHz in DMSO-d$_6$, draw only major isomer): δ=1.32-1.44 (2H, m), 1.48 (3H, s), 1.62 (2H, td), 1.81 (3H, s), 1.91 (2H, d), 1.94-2.02 (1H, m), 2.21 (2H, d), 5.56-5.62 (1H, m), 5.92 (1H, s), 7.71 (1H, s)

$^{19}$F-NMR (564 MHz in DMSO-d$_6$): δ=−73.05 (6F, s)

Synthesis Example 1-2

Synthesis of Monomer 2

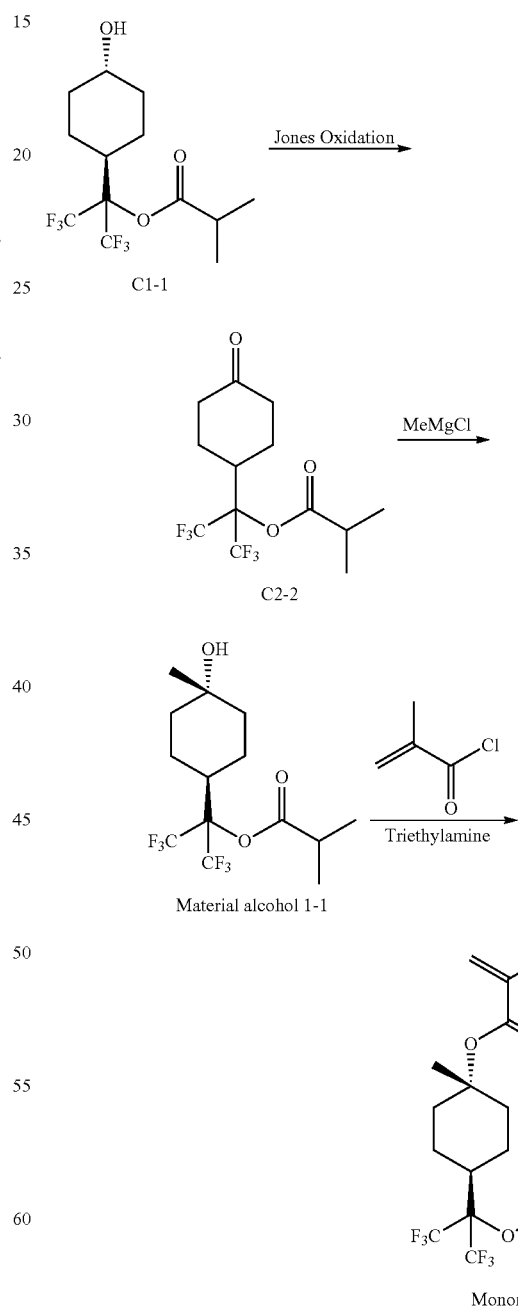

A monomer 2 (yield after three steps: 70%) was obtained in the same manner as in Synthesis Examples 1-1-1, 1-1-2, and 1-1-3 except that instead of an alcohol compound C-1, a protecting compound thereof C1-1 was used.

Synthesis Example 1-3

Synthesis of Monomer 3

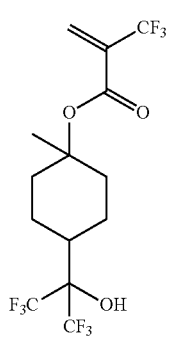

Monomer 3

A monomer 3 (yield after two steps: 62%) was obtained in the same manner as in Synthesis Examples 1-1-1, 1-1-2, 1-1-3, and 1-1-4 except that α-trifluoromethacryloyl chloride was used instead of methacryloyl chloride in Synthesis Example 1-1-3.

Synthesis Example 1-4

Synthesis of Monomer 4

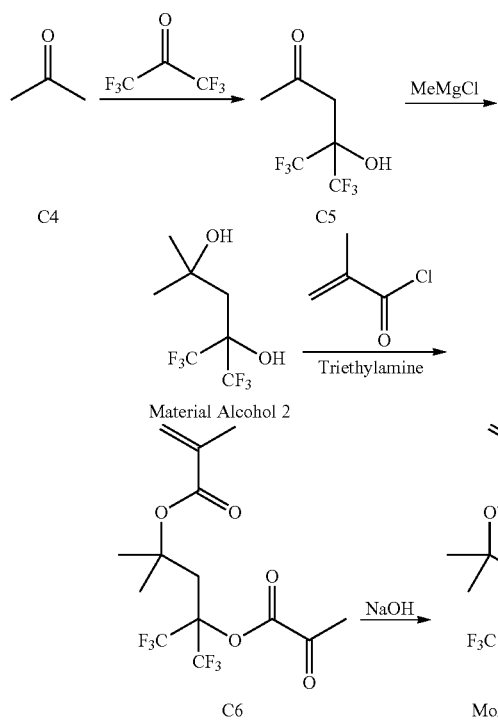

Synthesis Example 1-4-1

Synthesis of Ketone Compound C5

A ketone compound C5 was synthesized by a method described in Japanese Patent Laid-Open Publication No. 2005-239710.

Synthesis Example 1-4-2

Synthesis of Starting material Alcohol 2

A starting material alcohol 2 (crude yield: 98%) was obtained in the same manner as in Synthesis Examples 1-1-2 except that a ketone compound C5 was used instead of a ketone compound C2.

Synthesis Example 1-4-3

Synthesis of Bismethacrylate Compound C6

A bismethacrylate compound C6 (yield: 80%) was obtained in the same manner as in Synthesis Examples 1-1-3 except that an alcohol 2 was used instead of an alcohol 1.

Synthesis Example 1-4-4

Synthesis of Monomer 4

A monomer 4 (yield: 95%) was obtained in the same manner as in Synthesis Examples 1-1-4 except that a bismethacrylate compound C6 was used instead of a bismethacrylate compound C3.

Synthesis Example 1-5

Synthesis of Monomer 5

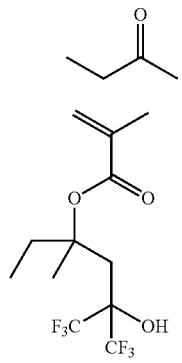

Monomer 5

A monomer 5 (yield after four steps: 52%) was obtained in the same manner as in Synthesis Examples 1-4-1, 1-4-2, 1-4-3, and 1-4-4 except that methyl ethyl ketone C7 was used instead of acetone C4.

Synthesis Example 1-6

Synthesis of Monomer 6

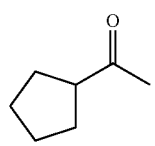

C8

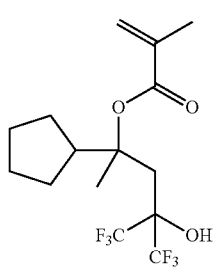

Monomer 6

A monomer 6 (yield after four steps: 56%) was obtained in the same manner as in Synthesis Examples 1-4-1, 1-4-2, 1-4-3, and 1-4-4 except that methyl cyclopentyl ketone C8 was used instead of acetone C4.

Synthesis Example 1-7

Synthesis of Monomer 7

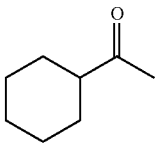

C9

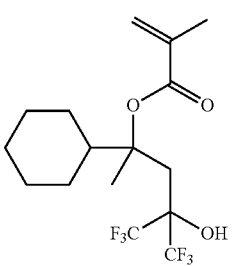

Monomer 7

A monomer 7 (yield after four steps: 55%) was obtained in the same manner as in Synthesis Examples 1-4-1, 1-4-2, 1-4-3, and 1-4-4 except that methyl cyclohexyl ketone C9 was used instead of acetone C4.

Synthesis Example 1-8

Synthesis of Monomer 8

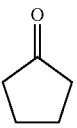

C10

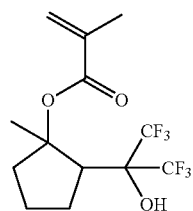

Monomer 8

A monomer 8 (yield after four steps: 51%) was obtained in the same manner as in Synthesis Examples 1-4-1, 1-4-2, 1-4-3, and 1-4-4 except that cyclopentanone C10 was used instead of acetone C4.

Synthesis Example 1-9

Synthesis of Monomer 9

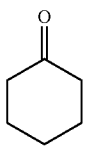

C11

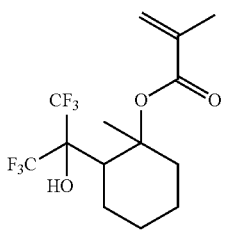

Monomer 9

A monomer 9 (yield after four steps: 52%) was obtained in the same manner as in Synthesis Examples 1-4-1, 1-4-2, 1-4-3, and 1-4-4 except that cyclohexanone C11 was used instead of acetone C4.

Synthesis Example 1-10
Synthesis of Monomer 10
C11
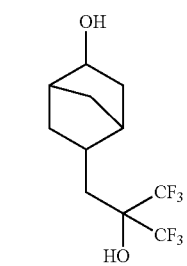
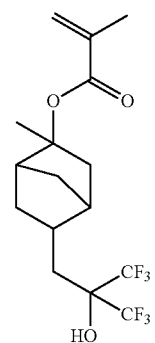
Monomer 10
A monomer 10 (yield after four steps: 55%) was obtained in the same manner as in Synthesis Examples 1-1-1, 1-1-2, 1-1-3, and 1-1-4 except using an alcohol C11 synthesized by the method described in Japanese Patent Laid-Open Publication No. 2005-22992.
Monomer 1
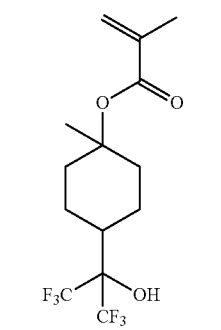
Monomer 2
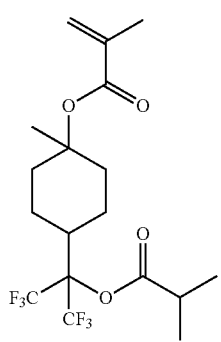
Monomer 3
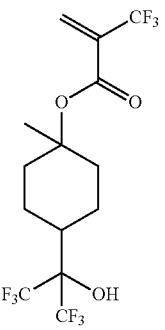
Monomer 4
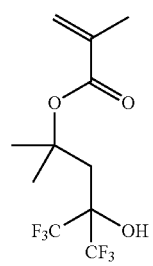
Monomer 5
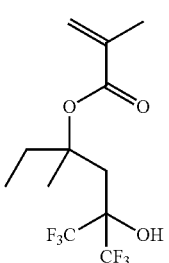
Monomer 6
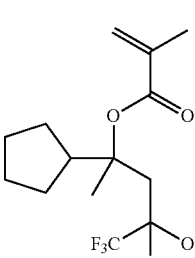
Monomer 7
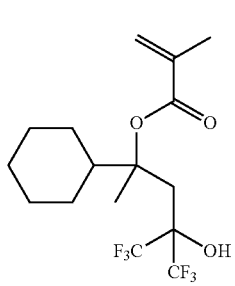
Monomer 8
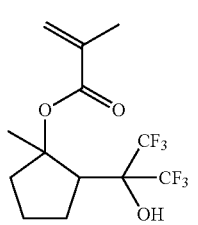

Monomer 9

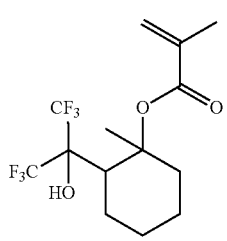

Monomer 10

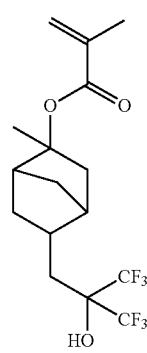

Synthesis Example 2

A polymer of the present invention was synthesized by the following scheme.

Synthesis Example 2-1

Synthesis of Polymer 1

11.75 g of monomer 1, 3.24 g of 4,8-dioxatricyclo[4.2.1.0$^{3,7}$]nonan-5-on-2-yl methacrylate, and 0.60 g of 2,2'-asobisisobutyronitrile were dissolved in 26.25 g of methyl ethyl ketone, and the solution was added dropwise to 8.75 g of methyl ethyl ketone at 80° C. for 4 hours under a nitrogen atmosphere with stirring. The mixture was then stirred at 80° C. for 2 hours. After cooling to room temperature, the mixture was added dropwise to 150 mL of n-hexane with vigorous stirring. The resulting solid material was collected by filtration, and dried under vacuum at 60° C. for 20 hours to obtain a polymer 1 represented by the following formula as a white powder. The yield was 14.0 g, and the yield rate was 90%. Mw represents a weight average molecular weight in terms of polystyrene measured by GPC.

Polymer 1

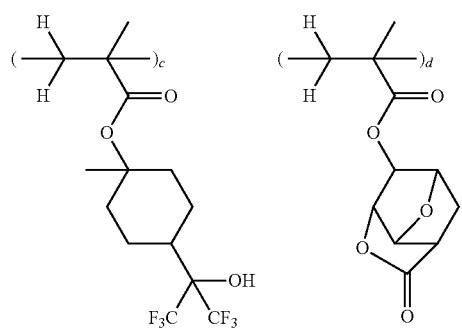

(c = 0.60, d = 0.40, Mw = 12,000)

Synthesis Examples 2-2 to 12 and Comparative Synthesis Examples 1-1 to 5

Synthesis of Polymers 2 to 12 and Comparative Polymers 1 to 5

Polymers 2 to 12 and comparative polymers 1 to 5 for comparative synthesis examples were produced in the same manner as in Synthesis Example 2-1 except that the kind and blending ratio of each monomer were changed. The induced ratio was a molar ratio.

Polymer 2

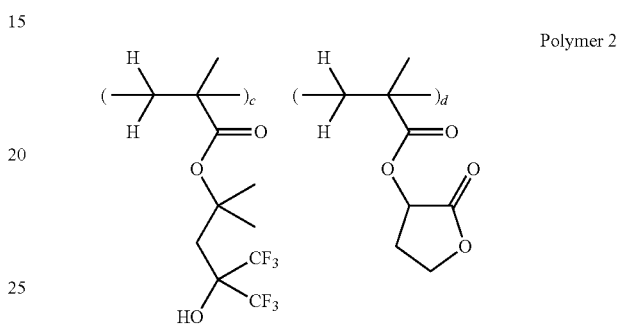

(c = 0.60, d = 0.40, Mw = 9,400)

Polymer 3

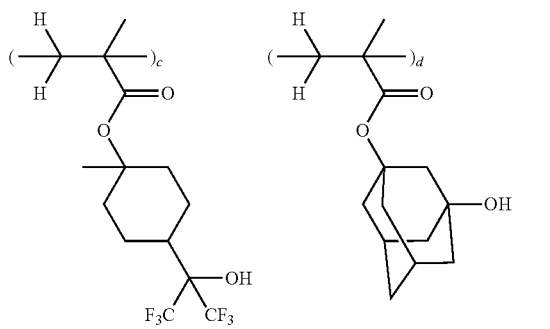

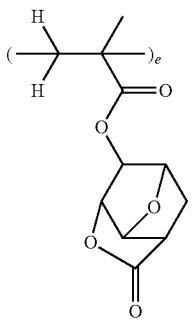

(c = 0.50, d = 0.10, e = 0.40, Mw = 11,600)

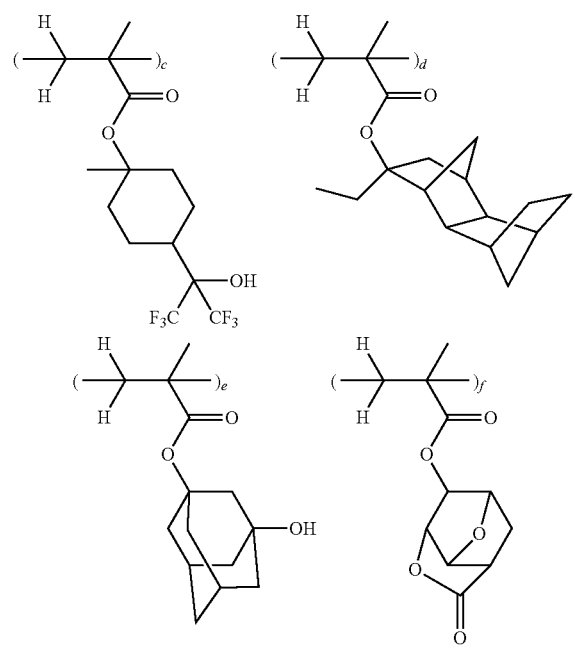
Polymer 4
(c = 0.20, d = 0.30, e = 0.10, f = 0.40, Mw = 9,400)
Polymer 5
(c = 0.20, d = 0.30, e = 0.10, f = 0.40, Mw = 9,000)
Polymer 6
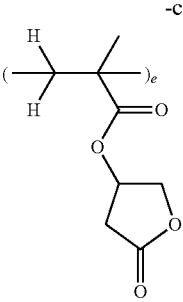
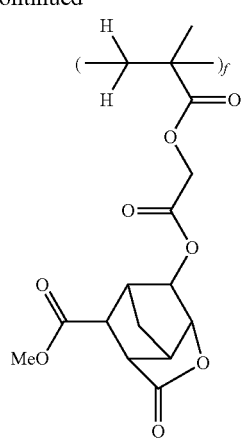
(c = 0.30, d = 0.20, e = 0.30, f = 0.20, Mw = 9,700)
Polymer 7
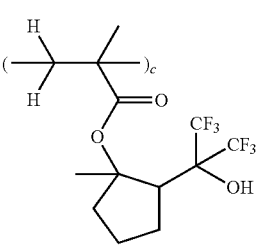
(c = 0.40, d = 0.20, e = 0.10, f = 0.30, Mw = 9,900)
Polymer 8
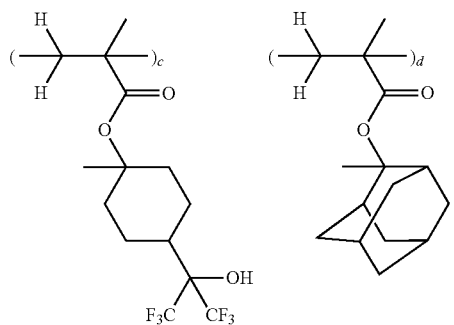

-continued
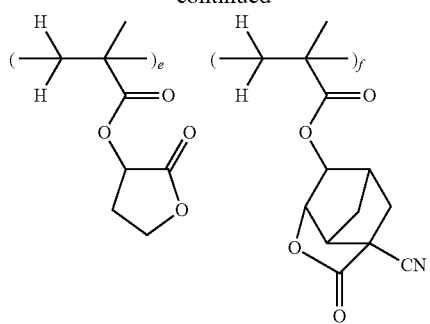
(c = 0.40, d = 0.20, e = 0.20, f = 0.20, Mw = 10,800)
Polymer 9
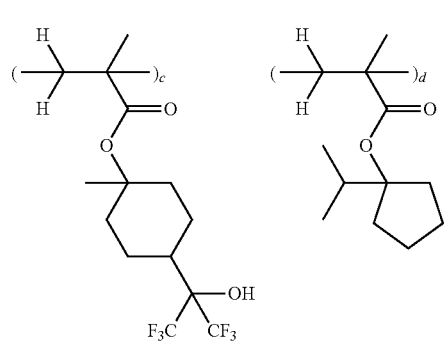
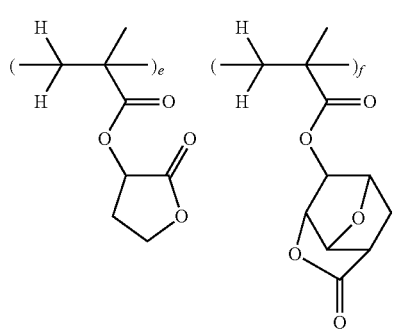
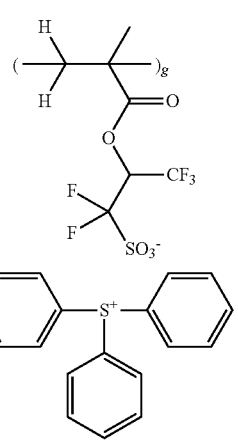
(c = 0.30, d = 0.20, e = 0.25, f = 0.20, g = 0.05, Mw = 8,700)
-continued
Polymer 10
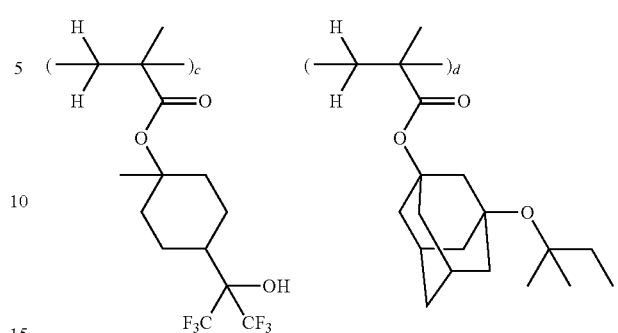
(c = 0.20, d = 0.30, e = 0.10, f = 0.40, Mw = 9,600)
Polymer 11
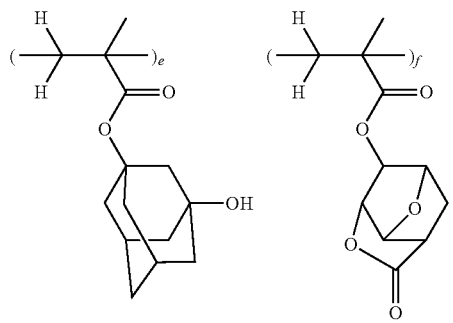
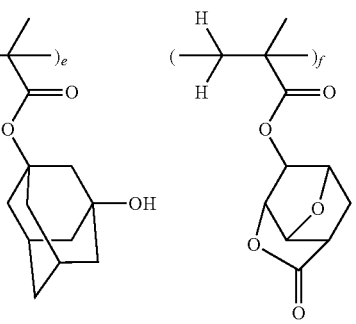
(c = 0.20, d = 0.30, e = 0.10, f = 0.40, Mw = 9,100)

-continued
Polymer 12
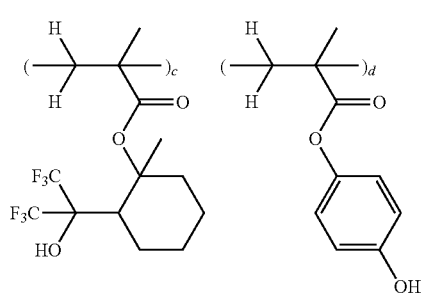
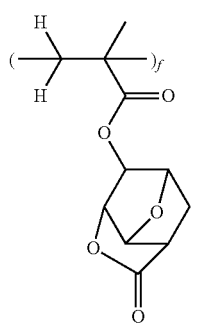
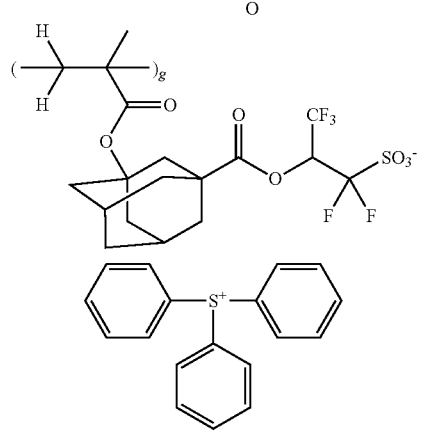
(c = 0.35, d = 0.20, e = 0.35, f = 0.10, Mw = 9,800)
Comparative Polymer 1
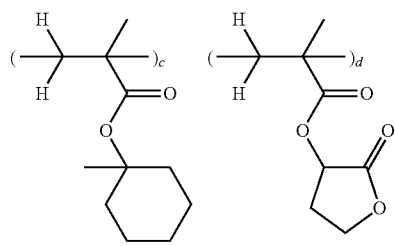
(c = 0.60, d = 0.40, Mw = 7,100)
Comparative Polymer 2
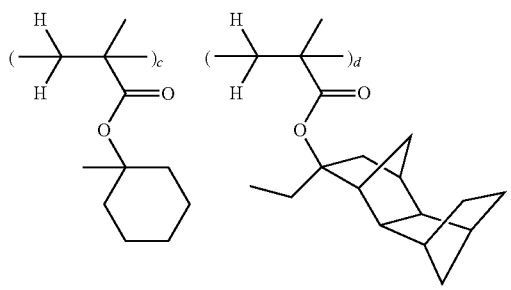
-continued
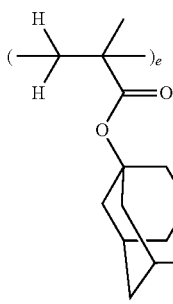
(c = 0.20, d = 0.30, e = 0.10, f = 0.40, Mw = 9,400)
Comparative Polymer 3
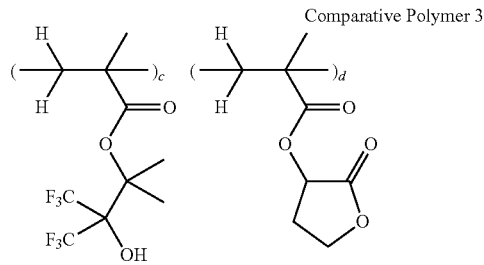
(c = 0.60, d = 0.40, Mw = 7,800)
Comparative Polymer 4
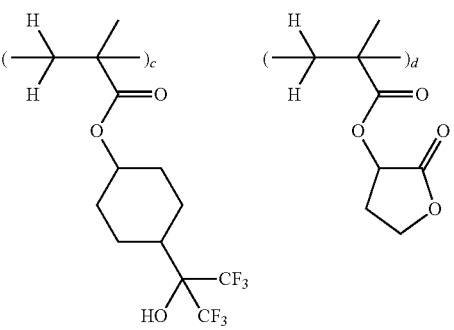
(c = 0.60, d = 0.40, Mw = 7,500)
Comparative Polymer 5
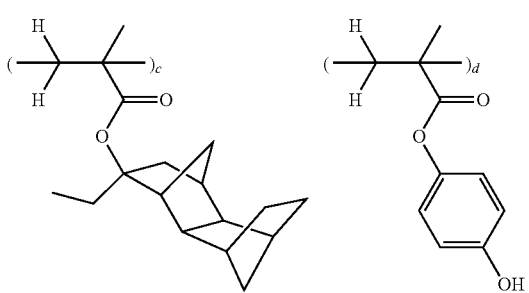
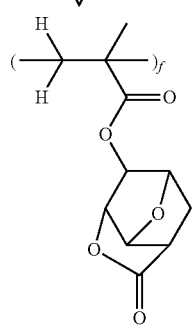

-continued

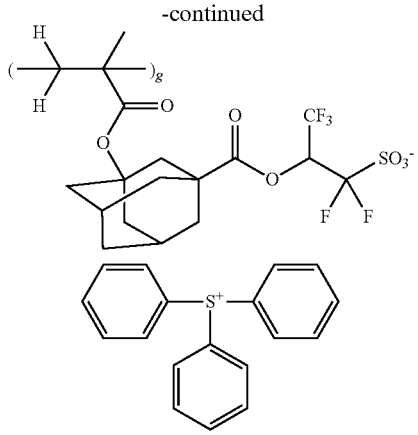

(c = 0.30, d = 0.20, f = 0.40, f = 0.10, Mw = 9,400)

Examples and Comparative Examples

Examples 1-1 to 15 and Comparative Examples 1-1 to 4

Preparation of Resist Composition

The produced resins of the present invention (polymers 1 to 11) and resins for Comparative Examples (comparative polymers 1 to 4) were used as a base resin, and acid generators, basic compounds, and solvents were each added in compositions shown in Table 1. After mixing and dissolution, the respective mixtures were filtered through a Teflon (registered trademark) filter (pore size: 0.2 μm) to obtain resist compositions (R-1-1 to 15) of the present invention and resist compositions (comparative R-1-1 to 4) for Comparative Examples. The solvent contained 0.01% by mass of surfactant KH-20 (available from Asahi Glass Co., Ltd.).

TABLE 1

| | Resist | Resin (part by mass) | Acid generator (part by mass) | Base (part by mass) | Solvent 1 (part by mass) | Solvent 2 (part by mass) |
|---|---|---|---|---|---|---|
| Example 1-1 | R-1-1 | Polymer 1 (80) | PAG-1 (15.0) | Base-1 (4.0) | PGMEA (2,700) | CyHO (300) |
| Example 1-2 | R-1-2 | Polymer 2 (80) | PAG-1 (15.0) | Base-1 (4.0) | PGMEA (2,700) | CyHO (300) |
| Example 1-3 | R-1-3 | Polymer 3 (80) | PAG-1 (15.0) | Base-1 (4.0) | PGMEA (2,700) | CyHO (300) |
| Example 1-4 | R-1-4 | Polymer 4 (80) | PAG-1 (15.0) | Base-1 (4.0) | PGMEA (2,700) | CyHO (300) |
| Example 1-5 | R-1-5 | Polymer 5 (80) | PAG-1 (15.0) | Base-1 (4.0) | PGMEA (2,700) | CyHO (300) |
| Example 1-6 | R-1-6 | Polymer 6 (80) | PAG-1 (15.0) | Base-1 (4.0) | PGMEA (2,700) | CyHO (300) |
| Example 1-7 | R-1-7 | Polymer 7 (80) | PAG-1 (15.0) | Base-1 (4.0) | PGMEA (2,700) | CyHO (300) |
| Example 1-8 | R-1-8 | Polymer 8 (80) | PAG-1 (15.0) | Base-1 (4.0) | PGMEA (2,700) | CyHO (300) |
| Example 1-9 | R-1-9 | Polymer 9 (80) | — | Base-1 (4.0) | PGMEA (2,700) | CyHO (300) |
| Example 1-10 | R-1-10 | Polymer 10 (80) | PAG-1 (15.0) | Base-1 (4.0) | PGMEA (2,700) | CyHO (300) |
| Example 1-11 | R-1-11 | Polymer 11 (80) | PAG-1 (15.0) | Base-1 (4.0) | PGMEA (2,700) | CyHO (300) |
| Example 1-12 | R-1-12 | Polymer 3 (80) | PAG-1 (15.0) | Base-1 (4.0) | PGMEA (2,700) | GBL (300) |
| Example 1-13 | R-1-13 | Polymer 5 (80) | PAG-1 (15.0) | Base-1 (4.0) | PGMEA (2,700) | GBL (300) |
| Example 1-14 | R-1-14 | Polymer 3 (80) | PAG-2 (15.0) | Base-1 (4.0) | PGMEA (2,700) | CyHO (300) |
| Example 1-15 | R-1-15 | Polymer 5 (80) | PAG-2 (15.0) | Base-1 (4.0) | PGMEA (2,700) | CyHO (300) |
| Comparative Example 1-1 | Comparative R-1-1 | Comparative Polymer 1 (80) | PAG-1 (15.0) | Base-1 (4.0) | PGMEA (2,700) | CyHO (300) |
| Comparative Example 1-2 | Comparative R-1-2 | Comparative Polymer 2 (80) | PAG-1 (15.0) | Base-1 (4.0) | PGMEA (2,700) | CyHO (300) |
| Comparative Example 1-3 | Comparative R-1-3 | Comparative Polymer 3 (80) | PAG-1 (15.0) | Base-1 (4.0) | PGMEA (2,700) | CyHO (300) |
| Comparative Example 1-4 | Comparative R-1-4 | Comparative Polymer 4 (80) | PAG-1 (15.0) | Base-1 (4.0) | PGMEA (2,700) | CyHO (300) |

Acid generators, bases, and solvents shown by abbreviations in Tables 1 and 3 are as follows.

PAG-1: triphenylsulfonium 2-(adamantane-1-carbonyloxy)-1,1,3,3,3-pentafluoropropane sulfonate PAG-2: 4-tert-butylphenyl diphenylsulfonium 2-(adamantane-1-carbonyloxy)-1,1,3,3,3-pentafluoropropane sulfonate Base-1: tri(2-methoxymethoxyethyl)amine PGMEA: 1-methoxyisopropyl acetate CyHO: cyclohexanone GBL: γ-butyrolactone

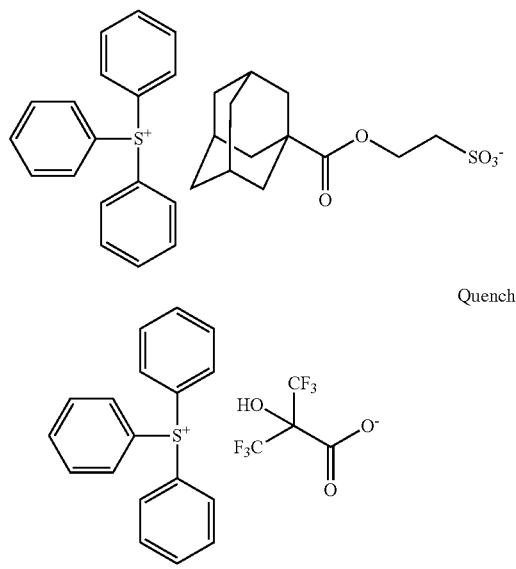

Quencher-1

Quencher-2

Evaluation of ArF Lithography Patterning (1)

A silicon wafer having an antireflective coating (ARC29A, available from Nissan Chemical Industries Ltd., 90 nm) was spin coated with each of the resist compositions (R-1-1 to 15) of the present invention and resist compositions for Comparative Examples (Comparative R-1-1 to 4), shown in Table 1, and baked at 100° C. for 60 seconds to form a resist film having a thickness of 100 nm. The resist film was spin coated with a resist top coat material (SIOC-3, available from Shin-Etsu Chemical Co., Ltd., 50 nm), and baked at 90° C. for 60 seconds. Using an ArF immersion excimer laser stepper (manufactured by Nikon Corporation, NA=1.30), a certain pattern on a 6% halftone phase shift mask was transcribed by exposure. The resist film was baked (PEB) for 60 seconds, and subjected to puddle development for 30 seconds using 2.38% by mass of tetramethylammonium hydroxide aqueous solution to form a line and space pattern. In the PEB, an optimum temperature for each resist composition was used.

A 40-nm 1:1 line and space pattern was observed with a top-down SEM (scanning electron microscope) and exposure dose dependence of pattern line width was examined. In general, when the exposure dose is increased, the line width is decreased, and the pattern is likely to collapse. The minimum line width in which a pattern does not collapse in a high exposure dose direction was determined as a collapse limit size (nm, which is good as the size is smaller). The variation of line width of a line in the 40-nm 1:1 line and space pattern was measured as a line width roughness (LWR) with SEM. As a LWR value is smaller, the pattern has no fluctuation and is good. The results of the evaluation are shown in Table 2.

TABLE 2

| Resist | | PEB Temperature | Collapse Limit Dimension | LWR (3σ) |
|---|---|---|---|---|
| Example 1-1 | R-1-1 | 100° C. | 30 nm | 5.4 nm |
| Example 1-2 | R-1-2 | 90° C. | 30 nm | 5.5 nm |
| Example 1-3 | R-1-3 | 95° C. | 27 nm | 5.3 nm |
| Example 1-4 | R-1-4 | 95° C. | 27 nm | 5.2 nm |
| Example 1-5 | R-1-5 | 95° C. | 28 nm | 5.1 nm |
| Example 1-6 | R-1-6 | 90° C. | 29 nm | 5.3 nm |
| Example 1-7 | R-1-7 | 95° C. | 28 nm | 5.4 nm |
| Example 1-8 | R-1-8 | 95° C. | 27 nm | 5.4 nm |
| Example 1-9 | R-1-9 | 90° C. | 29 nm | 5.4 nm |
| Example 1-10 | R-1-10 | 100° C. | 26 nm | 5.0 nm |
| Example 1-11 | R-1-11 | 90° C. | 27 nm | 5.2 nm |
| Example 1-12 | R-1-12 | 95° C. | 28 nm | 5.1 nm |
| Example 1-13 | R-1-13 | 100° C. | 27 nm | 5.3 nm |
| Example 1-14 | R-1-14 | 95° C. | 26 nm | 5.0 nm |
| Example 1-15 | R-1-15 | 100° C. | 26 nm | 5.2 nm |
| Comparative Example 1-1 | Comparative R-1-1 | 100° C. | 39 nm | 6.6 nm |
| Comparative Example 1-2 | Comparative R-1-2 | 100° C. | 35 nm | 6.3 nm |
| Comparative Example 1-3 | Comparative R-1-3 | 105° C. | No resolution | — |
| Comparative Example 1-4 | Comparative R-1-4 | 105° C. | No resolution | — |

From the results of Table 2, it was confirmed that the resist composition of the present invention (Examples 1-1 to 15) had a high resistance to pattern collapse and LWR was suppressed in immersion lithography by an ArF excimer laser.

Examples 2-1 to 15 and Comparative Examples 2-1 to 5

Evaluation of ArF Lithography Patterning (2)

A substrate for a trilayer process was prepared by forming a spin-on carbon film ODL-50 (available from Shin-Etsu Chemical Co., Ltd., carbon content: 80% by mass) of 200 nm on a silicon wafer and forming a silicon-containing spin-on hard mask SHB-A941 (silicon content: 43% by mass) of 35 nm on the film. The substrate was spin coated with a resist composition prepared in a composition shown in Table 3. The resist composition was baked at 100° C. for 60 seconds on a hot plate to form a resist film with a thickness of 100 nm. The film was spin coated with a composition for formation of a top coat shown in Table 4, and baked at 90° C. for 60 seconds to form a top coat with a thickness of 50 nm. In Examples 2-12 to 14 and Comparative Example 2-4, a top coat was not formed. In Example 2-15, the same resist (R-2-3) as in Example 2-3 was used.

The film was exposed by an ArF excimer laser immersion scanner (manufactured by Nikon Corporation, NSR-610C, NA: 1.30, σ 0.98/0.78, cross pole opening 20°, Azimuthally polarized illumination, 6% halftone phase-shift mask, lattice-liked mask having a pitch of 90 nm and a line width of 30 nm on wafer) while the exposure dose was changed. After the exposure, the film was baked (PEB) for 60 seconds at a temperature shown in Table 5. Buthyl acetate was discharged for 3 seconds from a development nozzle while the film was rotated at 30 rpm. Then, the rotation was stopped and puddle development was performed for 27 seconds. The film was rinsed with diisoamyl ether, spin-dried, and baked at 100° C. for 20 seconds to evaporate the rinsing solvent.

The size of 50 hole patterns formed by image reversal of solvent development was measured with TDSEM (manufactured by Hitachi High-Technologies Corporation, S-9380), and size variation 3σ was determined. The results are shown in Table 5.

TABLE 3

| | Resist | Polymer (part by mass) | Acid Generator (part by mass) | Basic Compound (part by mass) | Additive (part by mass) | Organic Solvent (part by mass) |
|---|---|---|---|---|---|---|
| Example 2-1 | R-2-1 | Polymer 1 (100) | PAG-1 (12.5) | Base-1 (1.50) | — | PGMEA (2,000) CyHO (500) |
| Example 2-2 | R-2-2 | Polymer 2 (100) | PAG-1 (12.5) | Base-1 (1.50) | — | PGMEA (2,000) CyHO (500) |
| Example 2-3 | R-2-3 | Polymer 3 (100) | PAG-1 (12.5) | Base-1 (1.50) | — | PGMEA (2,000) CyHO (500) |
| Example 2-4 | R-2-4 | Polymer 4 (100) | PAG-1 (12.5) | Base-1 (1.50) | — | PGMEA (2,000) CyHO (500) |
| Example 2-5 | R-2-5 | Polymer 5 (100) | PAG-1 (12.5) | Base-1 (1.50) | — | PGMEA (2,000) CyHO (500) |
| Example 2-6 | R-2-6 | Polymer 6 (100) | PAG-1 (12.5) | Base-1 (1.50) | — | PGMEA (2,000) CyHO (500) |
| Example 2-7 | R-2-7 | Polymer 7 (100) | PAG-1 (5.5) | Quencher-1 (4.50) | — | PGMEA (2,000) CyHO (500) |
| Example 2-8 | R-2-8 | Polymer 8 (100) | PAG-1 (5.5) | Quencher-2 (4.50) | — | PGMEA (2,000) CyHO (500) |
| Example 2-9 | R-2-9 | Polymer 9 (100) | — | Base-1 (1.50) | — | PGMEA (2,000) CyHO (500) |
| Example 2-10 | R-2-10 | Polymer 10 (100) | PAG-1 (5.5) | Quencher-1 (4.50) | — | PGMEA (2,000) CyHO (500) |
| Example 2-11 | R-2-11 | Polymer 11 (100) | PAG-1 (5.5) | Quencher-2 (4.50) | — | PGMEA (2,000) CyHO (500) |
| Example 2-12 | R-2-12 | Polymer 3 (100) | PAG-1 (5.5) | Base-1 (1.50) | Water-repellent Polymer 1 (6) | PGMEA (2,000) CyHO (500) |
| Example 2-13 | R-2-13 | Polymer 3 (100) | PAG-1 (12.5) | Base-1 (1.50) | Water-repellent Polymer 2 (6) | PGMEA (2,000) CyHO (500) |
| Example 2-14 | R-2-14 | Polymer 3 (100) | PAG-1 (12.5) | Base-1 (1.50) | Water-repellent Polymer 3 (6) | PGMEA (2,000) CyHO (500) |
| Comparative Example 2-1 | Comparative R-2-1 | Comparative Polymer 1 (100) | PAG-1 (12.5) | Base-1 (1.50) | — | PGMEA (2,000) CyHO (500) |
| Comparative Example 2-2 | Comparative R-2-2 | Comparative Polymer 2 (100) | PAG-1 (12.5) | Base-1 (1.50) | — | PGMEA (2,000) CyHO (500) |
| Comparative Example 2-3 | Comparative R-2-3 | Comparative Polymer 3 (100) | PAG-1 (12.5) | Base-1 (1.50) | — | PGMEA (2,000) CyHO (500) |
| Comparative Example 2-4 | Comparative R-2-4 | Comparative Polymer 2 (100) | PAG-1 (12.5) | Base-1 (1.50) | Water-repellent Polymer 1 (6) | PGMEA (2,000) CyHO (500) |
| Comparative Example 2-5 | Comparative R-2-5 | Comparative Polymer 4 (100) | PAG-1 (12.5) | Base-1 (1.50) | — | PGMEA (2,000) CyHO (500) |

Water-repellent polymers 1 to 3 shown in Table 3 are as follows.
Water-Repellant Polymer 1
Molecular weight (Mw)=7,700
Distribution (Mw/Mn)=1.77

Water-repellent polymers 1

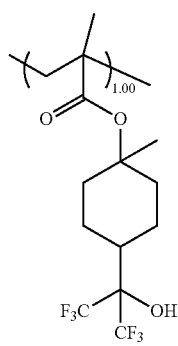

Water-Repellant Polymer 2
Molecular weight (Mw)=8,600
Distribution (Mw/Mn)=1.68

Water-repellent polymers 2

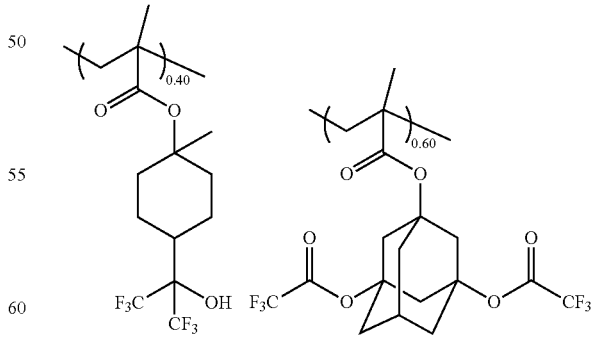

Water-Repellant Polymer 3
Molecular weight (Mw)=9,600
Distribution (Mw/Mn)=1.76

Water-repellent polymers 3

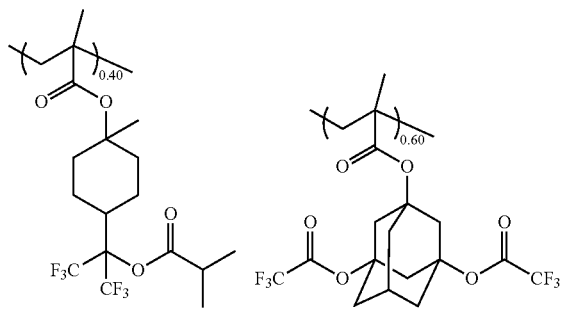

A top coat polymer 1 shown in Table 4 is as follows.
Top Coat Polymer 1
Molecular weight (Mw)=8,800
Distribution (Mw/Mn)=1.69

TABLE 4

| | Polymer (part by mass) | Additive (part by mass) | Organic Solvent (part by mass) |
|---|---|---|---|
| TC-1 | Top Coat Polymer 1 (100) | Tri-n-octylamine (0.5) | Diisoamyl ether (2,700) 2-methyl-1-butanol (270) |
| TC-2 | Top Coat Polymer 1 (100) | — | Diisoamyl ether (2,700) 2-methyl-1-butanol (270) |

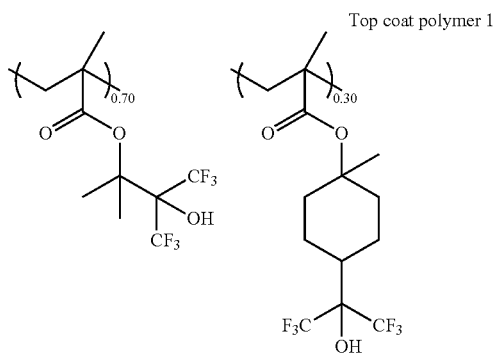

Top coat polymer 1

TABLE 5

| | Resist | Top coat | PEB Temperature (° C.) | Exposure does (mJ/cm$^2$) | Hole size variation 3σ (nm) |
|---|---|---|---|---|---|
| Example 2-1 | R-2-1 | TC-1 | 105 | 48 | 2.0 |
| Example 2-2 | R-2-2 | TC-1 | 95 | 33 | 2.0 |
| Example 2-3 | R-2-3 | TC-1 | 100 | 38 | 1.9 |
| Example 2-4 | R-2-4 | TC-1 | 100 | 38 | 2.1 |
| Example 2-5 | R-2-5 | TC-1 | 95 | 34 | 2.2 |
| Example 2-6 | R-2-6 | TC-1 | 100 | 46 | 2.2 |
| Example 2-7 | R-2-7 | TC-1 | 100 | 38 | 2.2 |
| Example 2-8 | R-2-8 | TC-1 | 110 | 39 | 2.4 |
| Example 2-9 | R-2-9 | TC-1 | 90 | 34 | 2.2 |
| Example 2-10 | R-2-10 | TC-1 | 100 | 30 | 2.1 |
| Example 2-11 | R-2-11 | TC-1 | 90 | 34 | 2.2 |
| Example 2-12 | R-2-12 | — | 95 | 30 | 2.1 |
| Example 2-13 | R-2-13 | — | 95 | 44 | 2.1 |
| Example 2-14 | R-2-14 | — | 95 | 42 | 2.3 |
| Example 2-15 | R-2-3 | TC-2 | 90 | 50 | 3.2 |
| Comparative Example 2-1 | Comparative R-2-1 | TC-1 | 100 | 80 | 5.8 |
| Comparative Example 2-2 | Comparative R-2-2 | TC-1 | 100 | 75 | 5.2 |
| Comparative Example 2-3 | Comparative R-2-3 | TC-1 | 110 | 92 | 6.8 |
| Comparative Example 2-4 | Comparative R-2-4 | — | 110 | 63 | 5.1 |
| Comparative Example 2-5 | Comparative R-2-5 | TC-2 | 90 | 88 | 6.2 |

From the results of Table 5, it was confirmed that the resist compositions of the present invention (Examples 2-1 to 15) had a higher sensitivity and small variation of hole size as compared with conventional cases (Comparative Examples 2-1 to 5) when a top coat is not used or a top coat that does not contain an additive is used.

Example 3-1 and Comparative Example 3-1

Evaluation of Electronic Beam Drawing

A solution obtained by dissolving each of the polymers (polymer 12 and comparative polymer 5) synthesized above in accordance with the compositions shown in Table 6 was filtered through a filter with a size of 0.2 μm to obtain a positive resist composition in evaluation of drawing.

A Si substrate having a diameter of 6 inch primed with hexamethyl disilazane (HMDS) was spin-coated with a positive resist composition by using a Clean Track Mark 5 (manufactured by Tokyo Electron Ltd.). The substrate was then pre-baked on a hot plate at 110° C. for 60 seconds to obtain a resist film with a thickness of 100 nm. On the substrate, a vacuum chamber drawing was performed by using a HL-800D (manufactured by Hitachi, Ltd.) at an HV voltage of 50 keV.

Immediately after the drawing, a post exposure bake (PEB) was performed on a hot plate for 60 seconds by using a Clean Track Mark 5 (manufactured by Tokyo Electron Ltd.), and then puddle-developed in 2.38% by mass of aqueous TMAH solution for 30 seconds to obtain a positive pattern.

The obtained resist pattern was evaluated as follows.

By taking the sensitivity of resist at the exposure amount to resolve a 120-nm line-and-space at 1:1 and the minimum size of the exposure amount at this time as a resolution power, a line width roughness (LWS) of a 120-nm LS was measured with a SEM.

The results of the sensitivity, the degree of resolution, and LWR with regard to the resist composition and the EB exposure are shown in Tables 6 and 7.

TABLE 6

| | Resist | Resin (part by mass) | Acid Generator (part by mass) | Base (part by mass) | Solvent 1 (part by mass) | Solvent 2 (part by mass) |
|---|---|---|---|---|---|---|
| Example 3-1 | R-3-1 | Polymer 12 (80) | — | Base-1 (1.0) | PGMEA (700) | CyHO (2300) |
| Comparative Example 3-1 | Comparative R-3-1 | Comparative Polymer 5 (80) | — | Base-1 (1.0) | PGMEA (700) | CyHO (2300) |

TABLE 7

| | Resist | PEB Temperature (°C.) | Exposure does (mJ/cm$^2$) | Resolution Power (nm) | LWR (nm) |
|---|---|---|---|---|---|
| Example 3-1 | R-3-1 | 105 | 35 | 80 | 2.0 |
| Comparative Example 3-1 | Comparative R-3-1 | 95 | 40 | 90 | 2.8 |

From the results of Table 7, it was confirmed that the resist composition of the present invention (Example 3-1) had a high sensitivity and resolution power and LWR was decreased in the electronic beam drawing.

The present invention is not restricted to the embodiments shown above. The embodiments are merely examples so that any embodiments composed of substantially the same technical concept as disclosed in the claims of the present invention and expressing a similar effect are included in the technical scope of the present invention.

What is claimed is:

1. A polymerizable tertiary ester compound represented by the following general formula (1a) or (1b),

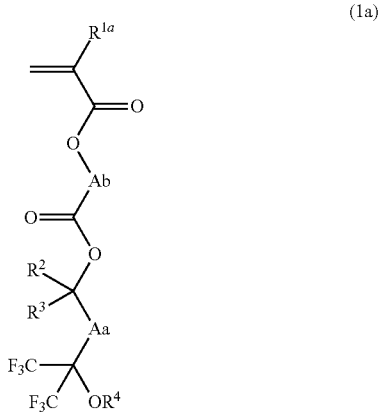

(1a)

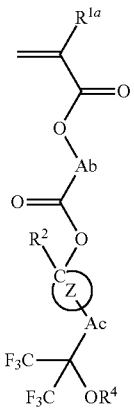

(1b)

wherein $R^{1a}$ represents a hydrogen atom, a fluorine atom, a methyl group, or a trifluoromethyl group; $R^{1b}$ represents a methyl group; each of $R^2$ and $R^3$ independently represents a linear, a branched, or a cyclic monovalent hydrocarbon group having 1 to 15 carbon atoms, or $R^2$ and $R^3$ may combine with each other to form a non-aromatic ring having 3 to 8 carbon atoms together with the carbon atoms to which they are bonded; Z represents a divalent group forming a substituted or an unsubstituted cyclopropane, cyclobutane, cyclopentane, cyclohexane, or norbornane ring together with the carbon atom to which it is bonded; Aa represents a linear, a branched, or a cyclic divalent hydrocarbon group having 1 to 10 carbon atoms; Ab represents a linear, a branched, or a cyclic divalent hydrocarbon group having 1 to 6 carbon atoms; Ac represents a single bond or a linear, a branched, or a cyclic divalent hydrocarbon group having 1 to 10 carbon atoms; $R^4$ represents a hydrogen atom, or a linear, a branched, or a cyclic monovalent hydrocarbon group having 1 to 15 carbon atoms, and when $R^4$ is a monovalent hydrocarbon group, —CH$_2$— may be substituted with —O— or —C(=O)—.

2. The polymerizable tertiary ester compound according to claim 1, wherein in the general formula (1a), any one or more of $R^2$, $R^3$, and Aa has a cyclic structure.

3. A polymer comprising any one or more kinds of repeating units represented by the following general formulae (2a) and (2b),

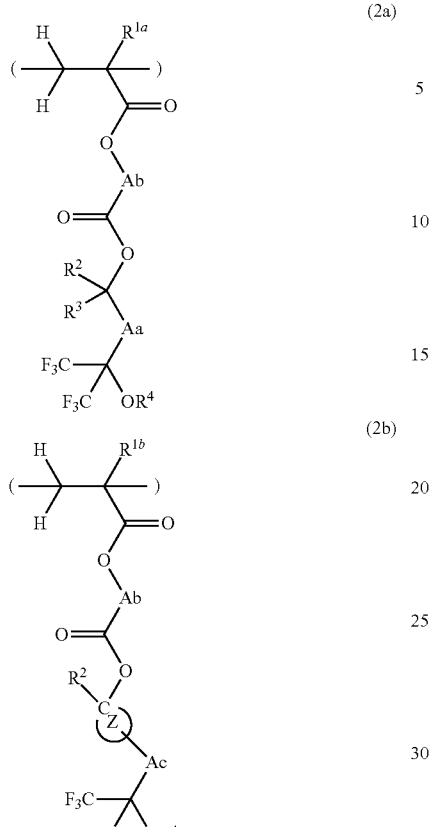

(2a)

(2b)

wherein $R^{1a}$ represents a hydrogen atom, a fluorine atom, a methyl group, or a trifluoromethyl group; $R^{1b}$ represents a methyl group; each of $R^2$ and $R^3$ independently represents a linear, a branched, or a cyclic monovalent hydrocarbon group having 1 to 15 carbon atoms, or $R^2$ and $R^3$ may combine with each other to form a non-aromatic ring having 3 to 8 carbon atoms together with the carbon atoms to which they are bonded; Z represents a divalent group forming a substituted or an unsubstituted cyclopropane, cyclobutane, cyclopentane, cyclohexane, or norbornane ring together with the carbon atom to which it is bonded; Aa represents a linear, a branched, or a cyclic divalent hydrocarbon group having 1 to 10 carbon atoms; Ab represents a linear, a branched, or a cyclic divalent hydrocarbon group having 1 to 6 carbon atoms; Ac represents a single bond or a linear, a branched, or a cyclic divalent hydrocarbon group having 1 to 10 carbon atoms; $R^4$ represents a hydrogen atom, or a linear, a branched, or a cyclic monovalent hydrocarbon group having 1 to 15 carbon atoms, and when $R^4$ is a monovalent hydrocarbon group, —$CH_2$— may be substituted with —O— or —C(=O)—.

4. The polymer according to claim 3, wherein in the general formula (2a), any one or more of $R^2$, $R^3$, and Aa has a cyclic structure.

5. The polymer according to claim 4, further comprising any one or more kinds of repeating units of represented by the following general formulae (3a) to (3d),

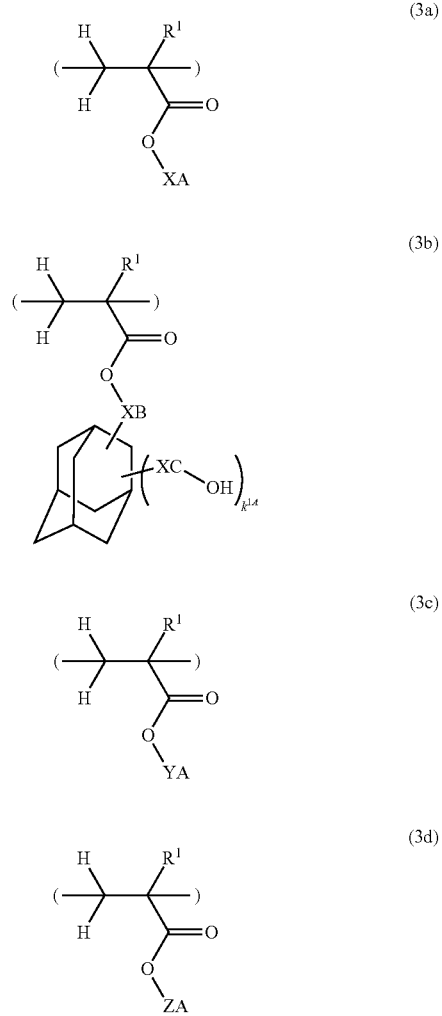

(3a)

(3b)

(3c)

(3d)

wherein $R^1$ is as defined above; XA represents an acid labile group; each of XB and XC independently represents a single bond, or a linear or a branched divalent hydrocarbon group having 1 to 4 carbon atoms; YA represents a substituent having a lactone, sultone, hydroxy, carboxyl, ester, ether, carbonyl, amido, or cyano structure; ZA represents a hydrogen atom, or a fluoroalkyl group having 1 to 15 carbon atoms, or a fluoroalcohol-containing substituent having 1 to 15 carbon atoms; and $k^{1A}$ represents an integer of 1 to 3.

6. The polymer according to claim 5, further comprising any one or more kinds of repeating units of represented by the following general formulae (d1) to (d3),

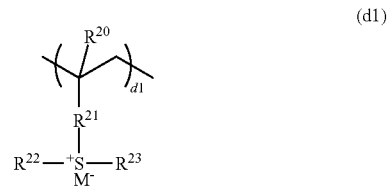

(d1)

-continued (d2)

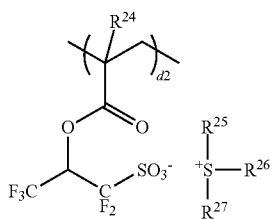

(d3)

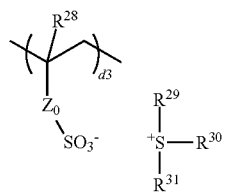

wherein each of $R^{20}$, $R^{24}$, and $R^{28}$ independently represents a hydrogen atom or a methyl group; $R^{21}$ represents a single bond, a phenylene group, —O—$R^{33}$—, or —C(=O)—Y—$R^{33}$—; Y represents an oxygen atom or NH; $R^{33}$ represents a linear, a branched, or a cyclic alkylene group having 1 to 6 carbon atoms, an alkenylene group, or a phenylene group, optionally containing a carbonyl group (—CO—), an ester group (—COO—), an ether group (—O—), or a hydroxy group; $R^{22}$, $R^{23}$, $R^{25}$, $R^{26}$, $R^{27}$, $R^{29}$, $R^{30}$, and $R^{31}$ represent the same or different linear, branched, or cyclic alkyl groups having 1 to 12 carbon atoms, optionally containing a carbonyl group, an ester group, or an ether group, or represent an aryl group having 6 to 12 carbon atoms, an aralkyl group having 7 to 20 carbon atoms, or a thiophenyl group; $Z_0$ represents a single bond, a methylene group, an ethylene group, a phenylene group, a fluorinated phenylene group, —O—$R^{32}$—, or —C(=O)—$Z_1$—$R^{32}$—; $Z_1$ represents an oxygen atom or NH; $R^{32}$ represents a linear, a branched, or a cyclic alkylene group having 1 to 6 carbon atoms, an alkenylene group, or a phenylene group, optionally containing a carbonyl group, an ester group, an ether group, or a hydroxy group; and $M^-$ represents a non-nucleophilic counter ion.

7. The polymer according to claim 4, further comprising any one or more kinds of repeating units of represented by the following general formulae (d1) to (d3), (d1)

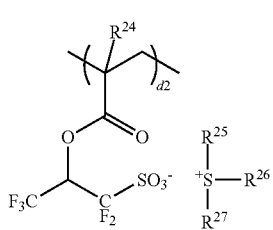

(d2)

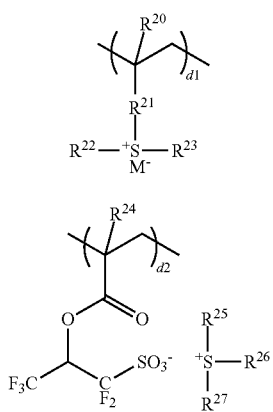

(d3)

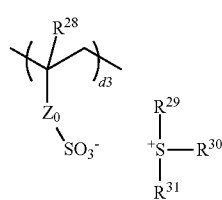

wherein each of $R^{20}$, $R^{24}$, and $R^{28}$ independently represents a hydrogen atom or a methyl group; $R^{21}$ represents a single bond, a phenylene group, —O—$R^{33}$—, or —C(=O)—Y—$R^{33}$—; Y represents an oxygen atom or NH; $R^{33}$ represents a linear, a branched, or a cyclic alkylene group having 1 to 6 carbon atoms, an alkenylene group, or a phenylene group, optionally containing a carbonyl group (—CO—), an ester group (—COO—), an ether group (—O—), or a hydroxy group; $R^{22}$, $R^{23}$, $R^{25}$, $R^{26}$, $R^{27}$, $R^{29}$, $R^{30}$, and $R^{31}$ represent the same or different linear, branched, or cyclic alkyl groups having 1 to 12 carbon atoms, optionally containing a carbonyl group, an ester group, or an ether group, or represent an aryl group having 6 to 12 carbon atoms, an aralkyl group having 7 to 20 carbon atoms, or a thiophenyl group; $Z_0$ represents a single bond, a methylene group, an ethylene group, a phenylene group, a fluorinated phenylene group, —O—$R^{32}$—, or —C(=O)—$Z_1$—$R^{32}$—; $Z_1$ represents an oxygen atom or NH; $R^{32}$ represents a linear, a branched, or a cyclic alkylene group having 1 to 6 carbon atoms, an alkenylene group, or a phenylene group, optionally containing a carbonyl group, an ester group, an ether group, or a hydroxy group; and $M^-$ represents a non-nucleophilic counter ion.

8. The polymer according to claim 3, further comprising any one or more kinds of repeating units of represented by the following general formulae (3a) to (3d), (3a)

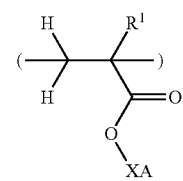

(3b)

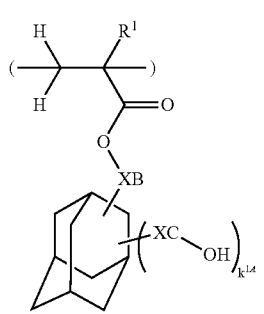

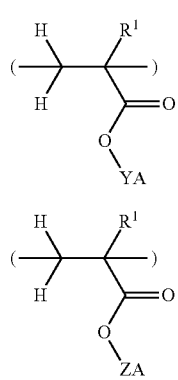

wherein $R^1$ is as defined above; XA represents an acid labile group; each of XB and XC independently represents a single bond, or a linear or a branched divalent hydrocarbon group having 1 to 4 carbon atoms; YA represents a substituent having a lactone, sultone, hydroxy, carboxyl, ester, ether, carbonyl, amido, or cyano structure; ZA represents a hydrogen atom, or a fluoroalkyl group having 1 to 15 carbon atoms, or a fluoroalcohol-containing substituent having 1 to 15 carbon atoms; and $k^{14}$ represents an integer of 1 to 3.

9. The polymer according to claim 7, further comprising any one or more kinds of repeating units of represented by the following general formulae (d1) to (d3),

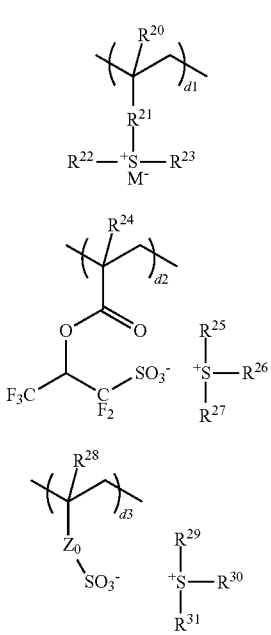

wherein each of $R^{20}$, $R^{24}$, and $R^{28}$ independently represents a hydrogen atom or a methyl group; $R^{21}$ represents a single bond, a phenylene group, —O—$R^{33}$—, or —C(=O)—Y—$R^{33}$—; Y represents an oxygen atom or NH; $R^{33}$ represents a linear, a branched, or a cyclic alkylene group having 1 to 6 carbon atoms, an alkenylene group, or a phenylene group, optionally containing a carbonyl group (—CO—), an ester group (—COO—), an ether group (—O—), or a hydroxy group; $R^{22}$, $R^{23}$, $R^{25}$, $R^{26}$, $R^{27}$, $R^{29}$, $R^{30}$, and $R^{31}$ represent the same or different linear, branched, or cyclic alkyl groups having 1 to 12 carbon atoms, optionally containing a carbonyl group, an ester group, or an ether group, or represent an aryl group having 6 to 12 carbon atoms, an aralkyl group having 7 to 20 carbon atoms, or a thiophenyl group; $Z_0$ represents a single bond, a methylene group, an ethylene group, a phenylene group, a fluorinated phenylene group, —O—$R^{32}$—, or —C(=O)—$Z_1$—$R^{32}$—; $Z_1$ represents an oxygen atom or NH; $R^{32}$ represents a linear, a branched, or a cyclic alkylene group having 1 to 6 carbon atoms, an alkenylene group, or a phenylene group, optionally containing a carbonyl group, an ester group, an ether group, or a hydroxy group; and $M^-$ represents a non-nucleophilic counter ion.

10. The polymer according to claim 3, further comprising any one or more kinds of repeating units of represented by the following general formulae (d1) to (d3),

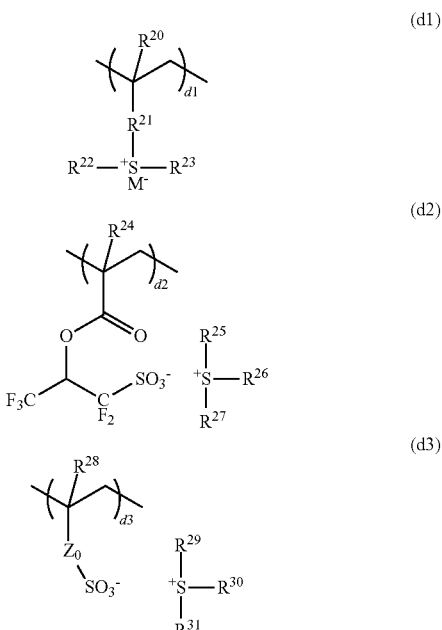

wherein each of $R^{20}$, $R^{24}$, and $R^{28}$ independently represents a hydrogen atom or a methyl group; $R^{21}$ represents a single bond, a phenylene group, —O—$R^{33}$—, or —C(=O)—Y—$R^{33}$—; Y represents an oxygen atom or NH; $R^{33}$ represents a linear, a branched, or a cyclic alkylene group having 1 to 6 carbon atoms, an alkenylene group, or a phenylene group, optionally containing a carbonyl group (—CO—), an ester group (—COO—), an ether group (—O—), or a hydroxy group; $R^{22}$, $R^{23}$, $R^{25}$, $R^{26}$, $R^{27}$, $R^{29}$, $R^{30}$, and $R^{31}$ represent the same or different linear, branched, or cyclic alkyl groups having 1 to 12 carbon atoms, optionally containing a carbonyl group, an ester group, or an ether group, or represent an aryl group having 6 to 12 carbon atoms, an aralkyl group having 7 to 20 carbon atoms, or a thiophenyl group; $Z_0$ represents a single bond, a methylene group, an ethylene group, a phenylene group, a fluorinated phenylene group, —O—$R^{32}$—, or —C(=O)—$Z_1$—$R^{32}$—; $Z_1$ represents an oxygen atom or NH; $R^{32}$ represents a linear, a branched, or acyclic alkylene group having 1 to 6 carbon atoms, an alkenylene group, or a phenylene group, optionally containing a carbonyl group, an ester group, an ether group, or a hydroxy group; and $M^-$ represents a non-nucleophilic counter ion.

11. A resist composition comprising the polymer of claim 3 as a base resin.

12. The resist composition according to claim 11, comprising any one or more of an organic solvent and an acid generator.

13. A patterning process comprising the steps of applying the resist composition of claim 11 to a substrate; performing exposure to a high-energy beam or an electron beam through a photomask after heat treatment; and performing development with a developer.

14. The patterning process according to claim 13, wherein in the development step, a non-exposed area of the resist film is dissolved in a developer containing an organic solvent to form a negative pattern.

15. The patterning process according to claim 13 wherein in the exposure step, a liquid having a high index of refraction of 1.0 or more is placed between the resist film and a projection lens to perform immersion lithography.

16. The patterning process according to claim 15, wherein in the immersion lithography, a top coat is applied to the resist film, and a liquid having a high index of refraction of 1.0 or more is placed between the top coat and the projection lens to perform immersion lithography.

* * * * *